(12) United States Patent
Meikle et al.

(10) Patent No.: US 7,615,224 B2
(45) Date of Patent: Nov. 10, 2009

(54) MULTIPLEX-BEAD COMPLEX FOR DETERMINATION OF LYSOSOMAL STORAGE DISORDERS

(75) Inventors: Peter John Meikle, Redwood Park (AU); John Joseph Hopwood, Stonyfell (AU); Douglas Alexander Brooks, North Cheltenham (AU); Caroline Dean, Christies Beach (AU)

(73) Assignee: Women's and Children's Hospital, North Adelaide (AU)

( * ) Notice: Subject to any disclaimer, the term of this patent is extended or adjusted under 35 U.S.C. 154(b) by 0 days.

(21) Appl. No.: 11/291,621

(22) Filed: Dec. 1, 2005

(65) Prior Publication Data

US 2007/0265432 A1   Nov. 15, 2007

Related U.S. Application Data

(60) Provisional application No. 60/632,610, filed on Dec. 2, 2004.

(51) Int. Cl.
*A61K 39/395* (2006.01)
*C07K 16/00* (2006.01)
*C07K 17/00* (2006.01)

(52) U.S. Cl. .................. 424/178.1; 530/391.1

(58) Field of Classification Search ........................ None
See application file for complete search history.

(56) References Cited

U.S. PATENT DOCUMENTS

2007/0072243 A1*  3/2007  Meikle et al. ................ 435/7.2

FOREIGN PATENT DOCUMENTS

| WO | WO 97/44668 | 11/1997 |
| WO | WO 00/55632 | 9/2000 |
| WO | WO 03/092601 A2 | 4/2003 |
| WO | WO 2004/088322 A1 | 3/2004 |

OTHER PUBLICATIONS

PCT International Search Report and written opinion Dated Feb. 6, 2006.

* cited by examiner

*Primary Examiner*—Ilia Ouspenski
(74) *Attorney, Agent, or Firm*—Jackson Walker L.L.P.

(57) ABSTRACT

Multiplexing bead technology is used for simultaneous screening of multiple LSD and normalizing measured enzyme activity or protein levels against other lysosomal proteins, enzymes, or enzyme activities. Diagnostic compositions include microspheres conjugated to purified antibodies that specifically bind LSD target antigens: saposin, LAMP-1, α-iduronidase, α-glucosidase, β-glucosidase, 2-sulphatase, 4-sulphatase, α-galactosidase, sphingomyelinase, 3-sulphatase or sulphamidase. The target antigens are naturally present in biological fluids or tissues of either LSD or non-LSD patients.

7 Claims, 70 Drawing Sheets

Antibody reagents used in 10-plex assays

| Assay | Bead region | Capture antibody | µg/1.25e6 beads | Reporter antibody | ng/well |
|---|---|---|---|---|---|
| 1. Lamp-1 | 25 | Sheep anti Lamp-1 polyclonal | 9 | Sheep anti Lamp-1 polyclonal | 16 |
| 2. saposin C | 42 | Monoclonal 7B2 | 9 | Monoclonal S13C1 G2 G3 | 32 |
| 3. α-L-iduronidase | 24 | Sheep anti α-iduronidase polyclonal | 36 | Sheep anti α-iduronidase polyclonal | 16 |
| 4. α-glucosidase | 26 | Sheep anti α-glucosidase polyclonal | 5 | Sheep anti α-glucosidase polyclonal | 16 |
| 5. β-glucosidase | 28 | Sheep anti β-glucosidase polyclonal | 9 | Sheep anti β-glucosidase polyclonal | 32 |
| 6. α-galactosidase | 43 | Sheep anti α-galactosidase polyclonal | 9 | Sheep anti α-galactosidase polyclonal | 32 |
| 7. N-acetylgalactosamine-4-sulphatase | 46 | Sheep anti 4-sulphatase polyclonal | 9 | Sheep anti 4-sulphatase polyclonal | 32 |
| 8. Iduronate 2-Sulphatase | 45 | Sheep anti 2-sulphatase polyclonal | 9 | Sheep anti 2-sulphatase polyclonal | 16 |
| 9. 3-Sulphatase | 44 | Sheep anti 3-sulphatase polyclonal | 5 | Sheep anti 3-sulphatase polyclonal | 32 |
| 10. Sphingomyelinase | 22 | Sheep anti-phingomyelinase polyclonal | 36 | Sheep anti sphingomyelinase polyclonal | 32 |

Figure 7

Precision Studies on the 11-Plex Assay

- Repeat assays of 20 x 3mm blood spots (3 adult controls)
- 20 spots divided across 5 plates
- %CV was calculated for each set of 4 repeats
- The %CV estimates obtained from each plate were averaged to indicate the reproducibility WITHIN plates (INTRA-ASSAY precision)
- % CV was calculated using all 20 data points, to indicate the reproducibility BETWEEN plates (INTER-ASSAY precision)

Figure 8

Intra and Inter-assay %CV for 11-Plex

| Protein Marker | INTRA-ASSAY | INTER-ASSAY |
| --- | --- | --- |
| sulphamidase | 8.7% | 12.1% |
| acid sphingomyelinase | 12.0% | 13.6% |
| alpha-iduronidase | 8.9% | 15.6% |
| LAMP-1 | 6.9% | 8.5% |
| alpha-glucosidase | 6.8% | 10.2% |
| beta-glucosidase | 14.0% | 15.8% |
| saposin C | 15.9% | 22.9% |
| alpha-galactosidase | 10.5% | 13.4% |
| arylsulphatase A | 6.7% | 10.1% |
| iduronate-2-sulphatase | 7.7% | 9.4% |
| 4-sulphatase | 6.8% | 11.2% |

Figure 9

Protein markers for LSD screening

| Disorder | Enzyme Deficiency | Australian Prevalence | Therapy |
|---|---|---|---|
| Gaucher disease | β-glucosidase | 1 in 57,000 | ERT |
| Fabry disease | α-galactosidase A | 1 in 117,000 | ERT |
| MPS I | α-L-iduronidase | 1 in 88,000 | ERT |
| Pompe disease | α-glucosidase | 1 in 146,000 | ERT (trials) |
| MPS VI | N-acetylgalactosamine 4-sulphatase | 1 in 235,000 | ERT (trials) |
| MPS II | iduronate-2-sulphatase | 1 in 136,000 | ERT (trials) |
| Krabbe disease | galactocerebrosidase | 1 in 201,000 | BMT |
| MLD | arylsulphatase A | 1 in 92,000 | BMT |
| MPS IVA | galactose 6-sulphatase | 1 in 169,000 | ERT (proposed) |
| Niemann-Pick type A/B | acid sphingomyelinase | 1 in 248,000 | ERT (proposed) |
| MPS IIIA | heparan-N-sulphatase | 1 in 114,000 | Research |
| MPS IIIB | α-N-acetylglucosaminidase | 1 in 211,000 | Research |
| TOTAL (n = 12) | | 1 in 10,500 | |

Figure 10

Validation of Multiplex Newborn Screening Assay

- Samples run in 24 plates over 4 weeks
- Liquid calibrators used
- 3 QC blood spots run with each plate
- Outliers repeated in 5 plates (results averaged)

Figure 17

Assay performance during Validation Studies
(3 x QC blood spots over 29 assays)

| Protein Marker | Mean (ug/L) | %CV QC A | %CV QC B | %CV QC C |
|---|---|---|---|---|
| sulphamidase | 8.8 | 18 | 14 | 13 |
| acid sphingomyelinase | 18.7 | 15 | 21 | 18 |
| alpha-iduronidase | 18.5 | 19 | 17 | 18 |
| LAMP-1 | 127.2 | 15 | 14 | 13 |
| alpha-glucosidase | 30.4 | 17 | 16 | 14 |
| beta-glucosidase | 10.5 | 22 | 21 | 22 |
| saposin C | 18.8 | 22 | 31 | 35 |
| alpha-galactosidase | 65.2 | 25 | 22 | 22 |
| arylsulphatase A | 78.5 | 16 | 13 | 11 |
| iduronate-2-sulphatase | 55.8 | 16 | 15 | 14 |
| 4-sulphatase | 5.2 | 30 | 26 | 27 |

Figure 18

Identification of LSD using single proteins

| Disorder | N= | Identified | % |
| --- | --- | --- | --- |
| Fabry | 8 | 8 | 100 |
| Gaucher | 7 | 0 | 0 |
| MLD | 4 | 4 | 100 |
| MLD (pseudo) | 4 | 4 | 100 |
| ML II/III | 8 | 8 | 100 |
| MPS I | 4 | 4 | 100 |
| MPS II | 15 | 15 | 100* |
| MPS IIIA | 11 | 11 | 100 |
| MPS VI | 2 | 2 | 100 |
| MSD | 1 | 1 | 100 |
| Niemann-Pick A/B | 5 | 5 | 100 |
| Pompe | 27 | 24 | 89 |
| Total | 96 | 86 | 90 |

Figure 44

Identification of LSD using protein ratios

| Disorder | N= | Number identified | % identified |
|---|---|---|---|
| Fabry | 8 | 8 | 100 |
| Gaucher | 7 | 2 | 29 |
| MLD | 4 | 4 | 100 |
| MLD (pseudo) | 4 | 4 | 100 |
| ML II/III | 8 | 8 | 100 |
| MPS I | 4 | 4 | 100 |
| MPS II | 15 | 15 | 100 |
| MPS IIIA | 11 | 11 | 100 |
| MPS VI | 2 | 2 | 100 |
| MSD | 1 | 1 | 100 |
| Niemann-Pick A/B | 5 | 5 | 100 |
| Pompe | 27 | 27 | 100 |
| Total | 96 | 91 | 95 |

Figure 50

Total Identification of LSD

| Disorder | N= | Identified (from Newborn) | % |
|---|---|---|---|
| Fabry | 11 | 11 | 100 |
| Gaucher | 12 | 6 | 50 |
| MLD | 4 | 4 | 100 |
| MLD (pseudo) | 4 | 4 | 100 |
| ML II/III | 10 | 10 | 100 |
| MPS I | 4 | 4 | 100 |
| MPS II | 19 | 19 | 100 |
| MPS IIIA | 13 | 13 | 100 |
| MPS VI | 2 | 2 | 100 |
| MSD | 1 | 1 | 100 |
| Niemann-Pick A/B | 5 | 5 | 100 |
| Pompe | 30 | 30 | 100 |
| Total | 115 | 109 | 95 |

Figure 60

Identification of LSD using single proteins

| Disorder | N= | Identified | % |
|---|---|---|---|
| Fabry | 8 | 8 | 100 |
| Gaucher | 7 | 0 | 0 |
| MLD | 4 | 4 | 100 |
| MLD (pseudo) | 4 | 4 | 100 |
| ML II/III | 8 | 8 | 100 |
| MPS I | 4 | 4 | 100 |
| MPS II | 15 | 15 | 100* |
| MPS IIIA | 11 | 11 | 100 |
| MPS VI | 2 | 2 | 100 |
| MSD | 1 | 1 | 100 |
| Niemann-Pick A/B | 5 | 5 | 100 |
| Pompe | 27 | 24 | 89 |
| Total | 96 | 86 | 90 |

Figure 61

Identification of retrospective LSD affected newborns

| Disorder | N= | Identified (from Newborn) | % |
|---|---|---|---|
| Fabry | 3 | 3 | 100 |
| Gaucher | 5 | 4 | 80 |
| MLD | 0 | | |
| MLD (pseudo) | 0 | | |
| ML II/III | 2 | 2 | 100 |
| MPS I | 0 | | |
| MPS II | 4 | 4 | 100 |
| MPS IIIA | 2 | 2 | 100 |
| MPS VI | 0 | | |
| MSD | 0 | | |
| Niemann-Pick A/B | 0 | | |
| Pompe | 3 | 3 | 100 |
| Total | 18 | 17 | 94 |

Figure 62

Table 1. Proposed structures of MPS II oligosaccharides derived from dermatan sulfate.

| Proposed Structure/ Composition | No. sulfate groups | charge states observed | Elution volume (mL) |
|---|---|---|---|
| Series 1 | | | |
| UA-HNAc | 1-2 | -1 | 210 |
| UA-HNAc-UA-HNAc | 2-4 | -2, -3 | 180 |
| UA-HNAc-[UA-HNAc]$_2$ | 1-6 | -2, -3, -4 | 153 |
| UA-HNAc-[UA-HNAc]$_3$ | 2-8 | -3, -4, -5 | 132 |
| UA-HNAc-[UA-HNAc]$_4$ | 3-9 | -3, -4, -5, -6 | 120 |
| UA-HNAc-[UA-HNAc]$_5$ | 4-10 | -4, -5, -6 | 111 |
| UA-HNAc-[UA-HNAc]$_6$ | 6-12 | -6, -7 | 105 |
| UA-HNAc-[UA-HNAc]$_7$ | 7-13 | -6, -7, -8 | 99 |
| Series 2 | | | |
| UA-HNAc-UA | 1 | -1, -2 | 201 |
| UA-[HNAc-UA]$_2$ | 1-5 | -2, -3, -4 | 156 |
| UA-[HNAc-UA]$_3$ | 3-7 | -3, -4, -5 | 132 |

[a] UA, uronic acid; HNAc, N-acetylhexosamine;

Figure 64

Table 2. Proposed structures of MPS II oligosaccharides derived from heparan sulfate.

| Proposed Structure/Composition[a] | No. sulfate groups | charge states observed | Elution volume |
|---|---|---|---|
| Series 1 | | | |
| UA-HN-UA | 1-2 | -1, -2 | 201 |
| UA-HN-UA-HNAc-UA | 2-5 | -2, -3, -4 | 168 |
| UA-HN-UA-HNAc-UA-HNAc-UA | 1-4 | -2, -3 | 138 |
| Series 2 | | | |
| UA-HN-UA-HN-UA | 3-5 | -2, -3, -4 | 177 |
| UA-HN-UA-HN-UA-HNAc-UA | 3-7 | -3, -4 | 147 |
| UA-HN-UA-HN-[UA-HNAc]$_2$-UA | 3-7 | -3, -4 | 126 |
| UA-HN-UA-HN-[UA-HNAc]$_3$-UA | 3-6 | -3, -4 | 114 |
| UA-HN-UA-HN-[UA-HNAc]$_4$-UA | 3-6 | -4, -5 | 105 |
| UA-HN-UA-HN-[UA-HNAc]$_5$-UA | 3-6 | -4, -5 | 99 |
| Series 3 | | | |
| UA-HN-[UA-HN]$_2$-UA-HNAc-UA | 5-10 | -3, -4, -5 | 132 |
| Series 4 | | | |
| UA-HN-UA-HNAc | 2-4 | -2, -3, -4 | 186 |
| UA-HN-[UA-HNAc]$_2$ | 2-4 | -2, -3 | 141 |
| UA-HN-[UA-HNAc]$_3$ | 1-5 | -3, -4 | 132 |
| UA-HN-[UA-HNAc]$_4$ | 3-5 | -3, -4 | 120 |

[a] UA, uronic acid; HN, hexosamine; HNAc, N-acetylhexosamine;

Figure 65

SEQUENCE LISTING

```
<160> NUMBER OF SEQ ID NOS: 10

<210> SEQ ID NO 1
<211> LENGTH: 524
<212> TYPE: PRT
<213> ORGANISM: artificial sequence
<220> FEATURE:
<223> OTHER INFORMATION: Amino acid sequence for Saposin.

<400> SEQUENCE: 1

Met Tyr Ala Leu Phe Leu Leu Ala Ser Leu Leu Gly Ala Ala Leu Ala
1               5                   10                  15

Gly Pro Val Leu Gly Leu Lys Glu Cys Thr Arg Gly Ser Ala Val Trp
            20                  25                  30

Cys Gln Asn Val Lys Thr Ala Ser Asp Cys Gly Ala Val Lys His Cys
        35                  40                  45

Leu Gln Thr Val Trp Asn Lys Pro Thr Val Lys Ser Leu Pro Cys Asp
    50                  55                  60

Ile Cys Lys Asp Val Val Thr Ala Ala Gly Asp Met Leu Lys Asp Asn
65                  70                  75                  80

Ala Thr Glu Glu Glu Ile Leu Val Tyr Leu Glu Lys Thr Cys Asp Trp
                85                  90                  95

Leu Pro Lys Pro Asn Met Ser Ala Ser Cys Lys Glu Ile Val Asp Ser
            100                 105                 110

Tyr Leu Pro Val Ile Leu Asp Ile Ile Lys Gly Glu Met Ser Arg Pro
        115                 120                 125

Gly Glu Val Cys Ser Ala Leu Asn Leu Cys Glu Ser Leu Gln Lys His
    130                 135                 140

Leu Ala Glu Leu Asn His Gln Lys Gln Leu Glu Ser Asn Lys Ile Pro
145                 150                 155                 160

Glu Leu Asp Met Thr Glu Val Val Ala Pro Phe Met Ala Asn Ile Pro
                165                 170                 175

Leu Leu Leu Tyr Pro Gln Asp Gly Pro Arg Ser Lys Pro Gln Pro Lys
            180                 185                 190

Asp Asn Gly Asp Val Cys Gln Asp Cys Ile Gln Met Val Thr Asp Ile
        195                 200                 205

Gln Thr Ala Val Arg Thr Asn Ser Thr Phe Val Gln Ala Leu Val Glu
    210                 215                 220

His Val Lys Glu Glu Cys Asp Arg Leu Gly Pro Gly Met Ala Asp Ile
225                 230                 235                 240

Cys Lys Asn Tyr Ile Ser Gln Tyr Ser Glu Ile Ala Ile Gln Met Met
                245                 250                 255

Met His Met Gln Pro Lys Glu Ile Cys Ala Leu Val Gly Phe Cys Asp
            260                 265                 270

Glu Val Lys Glu Met Pro Met Gln Thr Leu Val Pro Ala Lys Val Ala
        275                 280                 285
```

```
Ser Lys Asn Val Ile Pro Ala Leu Glu Leu Val Glu Pro Ile Lys Lys
    290                 295                 300

His Glu Val Pro Ala Lys Ser Asp Val Tyr Cys Glu Val Cys Glu Phe
305                 310                 315                 320

Leu Val Lys Glu Val Thr Lys Leu Ile Asp Asn Asn Lys Thr Glu Lys
                325                 330                 335

Glu Ile Leu Asp Ala Phe Asp Lys Met Cys Ser Lys Leu Pro Lys Ser
            340                 345                 350

Leu Ser Glu Glu Cys Gln Glu Val Val Asp Thr Tyr Gly Ser Ser Ile
        355                 360                 365

Leu Ser Ile Leu Leu Glu Glu Val Ser Pro Glu Leu Val Cys Ser Met
    370                 375                 380

Leu His Leu Cys Ser Gly Thr Arg Leu Pro Ala Leu Thr Val His Val
385                 390                 395                 400

Thr Gln Pro Lys Asp Gly Gly Phe Cys Glu Val Cys Lys Lys Leu Val
                405                 410                 415

Gly Tyr Leu Asp Arg Asn Leu Glu Lys Asn Ser Thr Lys Gln Glu Ile
            420                 425                 430

Leu Ala Ala Leu Glu Lys Gly Cys Ser Phe Leu Pro Asp Pro Tyr Gln
        435                 440                 445

Lys Gln Cys Asp Gln Phe Val Ala Glu Tyr Glu Pro Val Leu Ile Glu
    450                 455                 460

Ile Leu Val Glu Val Met Asp Pro Ser Phe Val Cys Leu Lys Ile Gly
465                 470                 475                 480

Ala Cys Pro Ser Ala His Lys Pro Leu Leu Gly Thr Glu Lys Cys Ile
                485                 490                 495

Trp Gly Pro Ser Tyr Trp Cys Gln Asn Thr Glu Thr Ala Ala Gln Cys
            500                 505                 510

Asn Ala Val Glu His Cys Lys Arg His Val Trp Asn
        515                 520

<210> SEQ ID NO 2
<211> LENGTH: 416
<212> TYPE: PRT
<213> ORGANISM: artificial sequence
<220> FEATURE:
<223> OTHER INFORMATION: Amino acid sequence of LAMP-1.

<400> SEQUENCE: 2

Met Ala Pro Arg Ser Ala Arg Arg Pro Leu Leu Leu Leu Leu Pro Val
1               5                   10                  15

Ala Ala Ala Arg Pro His Ala Leu Ser Ser Ala Ala Met Phe Met Val
            20                  25                  30

Lys Asn Gly Asn Gly Thr Ala Cys Ile Met Ala Asn Phe Ser Ala Ala
        35                  40                  45

Phe Ser Val Asn Tyr Asp Thr Lys Ser Gly Pro Lys Asn Met Thr Phe
    50                  55                  60

Asp Leu Pro Ser Asp Ala Thr Val Val Leu Asn Arg Ser Ser Cys Gly
65                  70                  75                  80

Lys Glu Asn Thr Ser Asp Pro Ser Leu Val Ile Ala Phe Gly Arg Gly
                85                  90                  95

His Thr Leu Thr Leu Asn Phe Thr Arg Asn Ala Thr Arg Tyr Ser Val
            100                 105                 110

Gln Leu Met Ser Phe Val Tyr Asn Leu Ser Asp Thr His Leu Phe Pro
        115                 120                 125
```

```
Asn Ala Ser Ser Lys Glu Ile Lys Thr Val Glu Ser Ile Thr Asp Ile
    130                 135                 140

Arg Ala Asp Ile Asp Lys Lys Tyr Arg Cys Val Ser Gly Thr Gln Val
145                 150                 155                 160

His Met Asn Asn Val Thr Val Thr Leu His Asp Ala Thr Ile Gln Ala
                165                 170                 175

Tyr Leu Ser Asn Ser Ser Phe Ser Arg Gly Glu Thr Arg Cys Glu Gln
            180                 185                 190

Asp Arg Pro Ser Pro Thr Thr Ala Pro Pro Ala Pro Ser Pro Ser
        195                 200                 205

Pro Ser Pro Val Pro Lys Ser Pro Ser Val Asp Lys Tyr Asn Val Ser
    210                 215                 220

Gly Thr Asn Gly Thr Cys Leu Leu Ala Ser Met Gly Leu Gln Leu Asn
225                 230                 235                 240

Leu Thr Tyr Glu Arg Lys Asp Asn Thr Thr Val Thr Arg Leu Leu Asn
                245                 250                 255

Ile Asn Pro Asn Lys Thr Ser Ala Ser Gly Ser Cys Gly Ala His Leu
            260                 265                 270

Val Thr Leu Glu Leu His Ser Glu Gly Thr Thr Val Leu Leu Phe Gln
        275                 280                 285

Phe Gly Met Asn Ala Ser Ser Ser Arg Phe Phe Leu Gln Gly Ile Gln
    290                 295                 300

Leu Asn Thr Ile Leu Pro Asp Ala Arg Asp Pro Ala Phe Lys Ala Ala
305                 310                 315                 320

Asn Gly Ser Leu Arg Ala Leu Gln Ala Thr Val Gly Asn Ser Tyr Lys
                325                 330                 335

Cys Asn Ala Glu Glu His Val Arg Val Thr Lys Ala Phe Ser Val Asn
            340                 345                 350

Ile Phe Lys Val Trp Val Gln Ala Phe Lys Val Glu Gly Gly Gln Phe
        355                 360                 365

Gly Ser Val Glu Glu Cys Leu Leu Asp Glu Asn Ser Thr Leu Ile Pro
    370                 375                 380

Ile Ala Val Gly Gly Ala Leu Ala Gly Leu Val Leu Ile Val Leu Ile
385                 390                 395                 400

Ala Tyr Leu Val Gly Arg Lys Arg Ser His Ala Gly Tyr Gln Thr Ile
                405                 410                 415

<210> SEQ ID NO 3
<211> LENGTH: 653
<212> TYPE: PRT
<213> ORGANISM: artificial sequence
<220> FEATURE:
<223> OTHER INFORMATION: Amino acid sequence for alphaiduronidase.

<400> SEQUENCE: 3

Met Arg Pro Leu Arg Pro Arg Ala Ala Leu Leu Ala Leu Leu Ala Ser
1               5                   10                  15

Leu Leu Ala Ala Pro Pro Val Ala Pro Ala Glu Ala Pro His Leu Val
            20                  25                  30

Gln Val Asp Ala Ala Arg Ala Leu Trp Pro Leu Arg Arg Phe Trp Arg
        35                  40                  45

Ser Thr Gly Phe Cys Pro Pro Leu Pro His Ser Gln Ala Asp Gln Tyr
    50                  55                  60

Val Leu Ser Trp Asp Gln Gln Leu Asn Leu Ala Tyr Val Gly Ala Val
65                  70                  75                  80
```

-continued

```
Pro His Arg Gly Ile Lys Gln Val Arg Thr His Trp Leu Leu Glu Leu
                 85                  90                  95
Val Thr Thr Arg Gly Ser Thr Gly Arg Gly Leu Ser Tyr Asn Phe Thr
            100                 105                 110
His Leu Asp Gly Tyr Leu Asp Leu Leu Arg Glu Asn Gln Leu Leu Pro
        115                 120                 125
Gly Phe Glu Leu Met Gly Ser Ala Ser Gly His Phe Thr Asp Phe Glu
    130                 135                 140
Asp Lys Gln Gln Val Phe Glu Trp Lys Asp Leu Val Ser Ser Leu Ala
145                 150                 155                 160
Arg Arg Tyr Ile Gly Arg Tyr Gly Leu Ala His Val Ser Lys Trp Asn
                165                 170                 175
Phe Glu Thr Trp Asn Glu Pro Asp His His Asp Phe Asp Asn Val Ser
            180                 185                 190
Met Thr Met Gln Gly Phe Leu Asn Tyr Tyr Asp Ala Cys Ser Glu Gly
        195                 200                 205
Leu Arg Ala Ala Ser Pro Ala Leu Arg Leu Gly Gly Pro Gly Asp Ser
    210                 215                 220
Phe His Thr Pro Pro Arg Ser Pro Leu Ser Trp Gly Leu Leu Arg His
225                 230                 235                 240
Cys His Asp Gly Thr Asn Phe Phe Thr Gly Glu Ala Gly Val Arg Leu
                245                 250                 255
Asp Tyr Ile Ser Leu His Arg Lys Gly Ala Arg Ser Ser Ile Ser Ile
            260                 265                 270
Leu Glu Gln Glu Lys Val Val Ala Gln Gln Ile Arg Gln Leu Phe Pro
        275                 280                 285
Lys Phe Ala Asp Thr Pro Ile Tyr Asn Asp Glu Ala Asp Pro Leu Val
    290                 295                 300
Gly Trp Ser Leu Pro Gln Pro Trp Arg Ala Asp Val Thr Tyr Ala Ala
305                 310                 315                 320
Met Val Val Lys Val Ile Ala Gln His Gln Asn Leu Leu Leu Ala Asn
                325                 330                 335
Thr Thr Ser Ala Phe Pro Tyr Ala Leu Leu Ser Asn Asp Asn Ala Phe
            340                 345                 350
Leu Ser Tyr His Pro His Pro Phe Ala Gln Arg Thr Leu Thr Ala Arg
        355                 360                 365
Phe Gln Val Asn Asn Thr Arg Pro Pro His Val Gln Leu Leu Arg Lys
    370                 375                 380
Pro Val Leu Thr Ala Met Gly Leu Leu Ala Leu Leu Asp Glu Glu Gln
385                 390                 395                 400
Leu Trp Ala Glu Val Ser Gln Ala Gly Thr Val Leu Asp Ser Asn His
                405                 410                 415
Thr Val Gly Val Leu Ala Ser Ala His Arg Pro Gln Gly Pro Ala Asp
            420                 425                 430
Ala Trp Arg Ala Ala Val Leu Ile Tyr Ala Ser Asp Asp Thr Arg Ala
        435                 440                 445
His Pro Asn Arg Ser Val Ala Val Thr Leu Arg Leu Arg Gly Val Pro
    450                 455                 460
Pro Gly Pro Gly Leu Val Tyr Val Thr Arg Tyr Leu Asp Asn Gly Leu
465                 470                 475                 480
Cys Ser Pro Asp Gly Glu Trp Arg Arg Leu Gly Arg Pro Val Phe Pro
                485                 490                 495
```

```
Thr Ala Glu Gln Phe Arg Arg Met Arg Ala Ala Glu Asp Pro Val Ala
            500                 505                 510

Ala Ala Pro Arg Pro Leu Pro Ala Gly Gly Arg Leu Thr Leu Arg Pro
        515                 520                 525

Ala Leu Arg Leu Pro Ser Leu Leu Val His Val Cys Ala Arg Pro
    530                 535                 540

Glu Lys Pro Pro Gly Gln Val Thr Arg Leu Arg Ala Leu Pro Leu Thr
545                 550                 555                 560

Gln Gly Gln Leu Val Leu Val Trp Ser Asp Glu His Val Gly Ser Lys
                565                 570                 575

Cys Leu Trp Thr Tyr Glu Ile Gln Phe Ser Gln Asp Gly Lys Ala Tyr
            580                 585                 590

Thr Pro Val Ser Arg Lys Pro Ser Thr Phe Asn Leu Phe Val Phe Ser
        595                 600                 605

Pro Asp Thr Gly Ala Val Ser Gly Ser Tyr Arg Val Arg Ala Leu Asp
    610                 615                 620

Tyr Trp Ala Arg Pro Gly Pro Phe Ser Asp Pro Val Pro Tyr Leu Glu
625                 630                 635                 640

Val Pro Val Pro Arg Gly Pro Pro Ser Pro Gly Asn Pro
                645                 650
```

```
<210> SEQ ID NO 4
<211> LENGTH: 952
<212> TYPE: PRT
<213> ORGANISM: artificial sequence
<220> FEATURE:
<223> OTHER INFORMATION: Amino acid sequence for alpha-glucosidase.

<400> SEQUENCE: 4

Met Gly Val Arg His Pro Pro Cys Ser His Arg Leu Leu Ala Val Cys
1               5                   10                  15

Ala Leu Val Ser Leu Ala Thr Ala Ala Leu Leu Gly His Ile Leu Leu
            20                  25                  30

His Asp Phe Leu Leu Val Pro Arg Glu Leu Ser Gly Ser Ser Pro Val
        35                  40                  45

Leu Glu Glu Thr His Pro Ala His Gln Gln Gly Ala Ser Arg Pro Gly
    50                  55                  60

Pro Arg Asp Ala Gln Ala His Pro Gly Arg Pro Arg Ala Val Pro Thr
65                  70                  75                  80

Gln Cys Asp Val Pro Pro Asn Ser Arg Phe Asp Cys Ala Pro Asp Lys
                85                  90                  95

Ala Ile Thr Gln Glu Gln Cys Glu Ala Arg Gly Cys Cys Tyr Ile Pro
            100                 105                 110

Ala Lys Gln Gly Leu Gln Gly Ala Gln Met Gly Gln Pro Trp Cys Phe
        115                 120                 125

Phe Pro Pro Ser Tyr Pro Ser Tyr Lys Leu Glu Asn Leu Ser Ser Ser
    130                 135                 140

Glu Met Gly Tyr Thr Ala Thr Leu Thr Arg Thr Thr Pro Thr Phe Phe
145                 150                 155                 160

Pro Lys Asp Ile Leu Thr Leu Arg Leu Asp Val Met Met Glu Thr Glu
                165                 170                 175

Asn Arg Leu His Phe Thr Ile Lys Asp Pro Ala Asn Arg Arg Tyr Glu
            180                 185                 190

Val Pro Leu Glu Thr Pro Arg Val His Ser Arg Ala Pro Ser Pro Leu
        195                 200                 205
```

-continued

Tyr Ser Val Glu Phe Ser Glu Pro Phe Gly Val Ile Val His Arg
210                 215                 220

Gln Leu Asp Gly Arg Val Leu Leu Asn Thr Thr Val Ala Pro Leu Phe
225                 230                 235                 240

Phe Ala Asp Gln Phe Leu Gln Leu Ser Thr Ser Leu Pro Ser Gln Tyr
                245                 250                 255

Ile Thr Gly Leu Ala Glu His Leu Ser Pro Leu Met Leu Ser Thr Ser
            260                 265                 270

Trp Thr Arg Ile Thr Leu Trp Asn Arg Asp Leu Ala Pro Thr Pro Gly
        275                 280                 285

Ala Asn Leu Tyr Gly Ser His Pro Phe Tyr Leu Ala Leu Glu Asp Gly
290                 295                 300

Gly Ser Ala His Gly Val Phe Leu Leu Asn Ser Asn Ala Met Asp Val
305                 310                 315                 320

Val Leu Gln Pro Ser Pro Ala Leu Ser Trp Arg Ser Thr Gly Gly Ile
                325                 330                 335

Leu Asp Val Tyr Ile Phe Leu Gly Pro Glu Pro Lys Ser Val Val Gln
            340                 345                 350

Gln Tyr Leu Asp Val Val Gly Tyr Pro Phe Met Pro Pro Tyr Trp Gly
        355                 360                 365

Leu Gly Phe His Leu Cys Arg Trp Gly Tyr Ser Ser Thr Ala Ile Thr
370                 375                 380

Arg Gln Val Val Glu Asn Met Thr Arg Ala His Phe Pro Leu Asp Val
385                 390                 395                 400

Gln Trp Asn Asp Leu Asp Tyr Met Asp Ser Arg Arg Asp Phe Thr Phe
                405                 410                 415

Asn Lys Asp Gly Phe Arg Asp Phe Pro Ala Met Val Gln Glu Leu His
            420                 425                 430

Gln Gly Gly Arg Arg Tyr Met Met Ile Val Asp Pro Ala Ile Ser Ser
        435                 440                 445

Ser Gly Pro Ala Gly Ser Tyr Arg Pro Tyr Asp Glu Gly Leu Arg Arg
450                 455                 460

Gly Val Phe Ile Thr Asn Glu Thr Gly Gln Pro Leu Ile Gly Lys Val
465                 470                 475                 480

Trp Pro Gly Ser Thr Ala Phe Pro Asp Phe Thr Asn Pro Thr Ala Leu
                485                 490                 495

Ala Trp Trp Glu Asp Met Val Ala Glu Phe His Asp Gln Val Pro Phe
            500                 505                 510

Asp Gly Met Trp Ile Asp Met Asn Glu Pro Ser Asn Phe Ile Arg Gly
        515                 520                 525

Ser Glu Asp Gly Cys Pro Asn Asn Glu Leu Glu Asn Pro Pro Tyr Val
530                 535                 540

Pro Gly Val Val Gly Gly Thr Leu Gln Ala Ala Thr Ile Cys Ala Ser
545                 550                 555                 560

Ser His Gln Phe Leu Ser Thr His Tyr Asn Leu His Asn Leu Tyr Gly
                565                 570                 575

Leu Thr Glu Ala Ile Ala Ser His Arg Ala Leu Val Lys Ala Arg Gly
            580                 585                 590

Thr Arg Pro Phe Val Ile Ser Arg Ser Thr Phe Ala Gly His Gly Arg
        595                 600                 605

Tyr Ala Gly His Trp Thr Gly Asp Val Trp Ser Ser Trp Glu Gln Leu
610                 615                 620

Ala Ser Ser Val Pro Glu Ile Leu Gln Phe Asn Leu Leu Gly Val Pro

```
                625                 630                 635                 640
Leu Val Gly Ala Asp Val Cys Gly Phe Leu Gly Asn Thr Ser Glu Glu
                645                 650                 655

Leu Cys Val Arg Trp Thr Gln Leu Gly Ala Phe Tyr Pro Phe Met Arg
                660                 665                 670

Asn His Asn Ser Leu Leu Ser Leu Pro Gln Glu Pro Tyr Ser Phe Ser
                675                 680                 685

Glu Pro Ala Gln Gln Ala Met Arg Lys Ala Leu Thr Leu Arg Tyr Ala
                690                 695                 700

Leu Leu Pro His Leu Tyr Thr Leu Phe His Gln Ala His Val Ala Gly
705                 710                 715                 720

Glu Thr Val Ala Arg Pro Leu Phe Leu Glu Phe Pro Lys Asp Ser Ser
                725                 730                 735

Thr Trp Thr Val Asp His Gln Leu Leu Trp Gly Glu Ala Leu Leu Ile
                740                 745                 750

Thr Pro Val Leu Gln Ala Gly Lys Ala Glu Val Thr Gly Tyr Phe Pro
                755                 760                 765

Leu Gly Thr Trp Tyr Asp Leu Gln Thr Val Pro Ile Glu Ala Leu Gly
                770                 775                 780

Ser Leu Pro Pro Pro Ala Ala Pro Arg Glu Pro Ala Ile His Ser
785                 790                 795                 800

Glu Gly Gln Trp Val Thr Leu Pro Ala Pro Leu Asp Thr Ile Asn Val
                805                 810                 815

His Leu Arg Ala Gly Tyr Ile Ile Pro Leu Gln Gly Pro Gly Leu Thr
                820                 825                 830

Thr Thr Glu Ser Arg Gln Gln Pro Met Ala Leu Ala Val Ala Leu Thr
                835                 840                 845

Lys Gly Gly Glu Ala Arg Gly Glu Leu Phe Trp Asp Asp Gly Glu Ser
                850                 855                 860

Leu Glu Val Leu Glu Arg Gly Ala Tyr Thr Gln Val Ile Phe Leu Ala
865                 870                 875                 880

Arg Asn Asn Thr Ile Val Asn Glu Leu Val Arg Val Thr Ser Glu Gly
                885                 890                 895

Ala Gly Leu Gln Leu Gln Lys Val Thr Val Leu Gly Val Ala Thr Ala
                900                 905                 910

Pro Gln Gln Val Leu Ser Asn Gly Val Pro Val Ser Asn Phe Thr Tyr
                915                 920                 925

Ser Pro Asp Thr Lys Val Leu Asp Ile Cys Val Ser Leu Leu Met Gly
                930                 935                 940

Glu Gln Phe Leu Val Ser Trp Cys
945                 950
```

<210> SEQ ID NO 5
<211> LENGTH: 536
<212> TYPE: PRT
<213> ORGANISM: artificial sequence
<220> FEATURE:
<223> OTHER INFORMATION: Amino acid sequence for beta-glucosidase.

<400> SEQUENCE: 5

```
Met Glu Phe Ser Ser Pro Ser Arg Glu Glu Cys Pro Lys Pro Leu Ser
1               5                   10                  15

Arg Val Ser Ile Met Ala Gly Ser Leu Thr Gly Leu Leu Leu Leu Gln
                20                  25                  30

Ala Val Ser Trp Ala Ser Gly Ala Arg Pro Cys Ile Pro Lys Ser Phe
```

-continued

```
                35                  40                  45
Gly Tyr Ser Ser Val Val Cys Val Cys Asn Ala Thr Tyr Cys Asp Ser
 50                  55                  60

Phe Asp Pro Pro Thr Phe Pro Ala Leu Gly Thr Phe Ser Arg Tyr Glu
65                  70                  75                  80

Ser Thr Arg Ser Gly Arg Met Glu Leu Ser Met Gly Pro Ile Gln
             85                  90                  95

Ala Asn His Thr Gly Thr Gly Leu Leu Leu Thr Leu Gln Pro Glu Gln
             100                 105                 110

Lys Phe Gln Lys Val Lys Gly Phe Gly Gly Ala Met Thr Asp Ala Ala
             115                 120                 125

Ala Leu Asn Ile Leu Ala Leu Ser Pro Pro Ala Gln Asn Leu Leu Leu
130                 135                 140

Lys Ser Tyr Phe Ser Glu Glu Gly Ile Gly Tyr Asn Ile Ile Arg Val
145                 150                 155                 160

Pro Met Ala Ser Cys Asp Phe Ser Ile Arg Thr Tyr Thr Tyr Ala Asp
                 165                 170                 175

Thr Pro Asp Asp Phe Gln Leu His Asn Phe Ser Leu Pro Glu Glu Asp
                 180                 185                 190

Thr Lys Leu Lys Ile Pro Leu Ile His Arg Ala Leu Gln Leu Ala Gln
                 195                 200                 205

Arg Pro Val Ser Leu Leu Ala Ser Pro Trp Thr Ser Pro Thr Trp Leu
             210                 215                 220

Lys Thr Asn Gly Ala Val Asn Gly Lys Gly Ser Leu Lys Gly Gln Pro
225                 230                 235                 240

Gly Asp Ile Tyr His Gln Thr Trp Ala Arg Tyr Phe Val Lys Phe Leu
                 245                 250                 255

Asp Ala Tyr Ala Glu His Lys Leu Gln Phe Trp Ala Val Thr Ala Glu
                 260                 265                 270

Asn Glu Pro Ser Ala Gly Leu Leu Ser Gly Tyr Pro Phe Gln Cys Leu
                 275                 280                 285

Gly Phe Thr Pro Glu His Gln Arg Asp Phe Ile Ala Arg Asp Leu Gly
                 290                 295                 300

Pro Thr Leu Ala Asn Ser Thr His His Asn Val Arg Leu Leu Met Leu
305                 310                 315                 320

Asp Asp Gln Arg Leu Leu Leu Pro His Trp Ala Lys Val Val Leu Thr
                 325                 330                 335

Asp Pro Glu Ala Ala Lys Tyr Val His Gly Ile Ala Val His Trp Tyr
                 340                 345                 350

Leu Asp Phe Leu Ala Pro Ala Lys Ala Thr Leu Gly Glu Thr His Arg
                 355                 360                 365

Leu Phe Pro Asn Thr Met Leu Phe Ala Ser Glu Ala Cys Val Gly Ser
                 370                 375                 380

Lys Phe Trp Glu Gln Ser Val Arg Leu Gly Ser Trp Asp Arg Gly Met
385                 390                 395                 400

Gln Tyr Ser His Ser Ile Ile Thr Asn Leu Leu Tyr His Val Val Gly
                 405                 410                 415

Trp Thr Asp Trp Asn Leu Ala Leu Asn Pro Glu Gly Gly Pro Asn Trp
                 420                 425                 430

Val Arg Asn Phe Val Asp Ser Pro Ile Ile Val Asp Ile Thr Lys Asp
                 435                 440                 445

Thr Phe Tyr Lys Gln Pro Met Phe Tyr His Leu Gly His Phe Ser Lys
450                 455                 460
```

```
Phe Ile Pro Glu Gly Ser Gln Arg Val Gly Leu Val Ala Ser Gln Lys
465                 470                 475                 480

Asn Asp Leu Asp Ala Val Ala Leu Met His Pro Asp Gly Ser Ala Val
            485                 490                 495

Val Val Val Leu Asn Arg Ser Ser Lys Asp Val Pro Leu Thr Ile Lys
            500                 505                 510

Asp Pro Ala Val Gly Phe Leu Glu Thr Ile Ser Pro Gly Tyr Ser Ile
            515                 520                 525

His Thr Tyr Leu Trp His Arg Gln
    530                 535

<210> SEQ ID NO 6
<211> LENGTH: 550
<212> TYPE: PRT
<213> ORGANISM: artificial sequence
<220> FEATURE:
<223> OTHER INFORMATION: Amino acid sequence for 2-sulphatase.

<400> SEQUENCE: 6

Met Pro Pro Pro Arg Thr Gly Arg Gly Leu Leu Trp Leu Gly Leu Val
1               5                   10                  15

Leu Ser Ser Val Cys Val Ala Leu Gly Ser Glu Thr Gln Ala Asn Ser
            20                  25                  30

Thr Thr Asp Ala Leu Asn Val Leu Ile Ile Val Asp Asp Leu Arg
        35                  40                  45

Pro Ser Leu Gly Cys Tyr Gly Asp Lys Leu Val Arg Ser Pro Asn Ile
    50                  55                  60

Asp Gln Leu Ala Ser His Ser Leu Leu Phe Gln Asn Ala Phe Ala Gln
65                  70                  75                  80

Gln Ala Val Cys Ala Pro Ser Arg Val Ser Phe Leu Thr Gly Arg Arg
                85                  90                  95

Pro Asp Thr Thr Arg Leu Tyr Asp Phe Asn Ser Tyr Trp Arg Val His
            100                 105                 110

Ala Gly Asn Phe Ser Thr Ile Pro Gln Tyr Phe Lys Glu Asn Gly Tyr
        115                 120                 125

Val Thr Met Ser Val Gly Lys Val Phe His Pro Gly Ile Ser Ser Asn
    130                 135                 140

His Thr Asp Asp Ser Pro Tyr Ser Trp Ser Phe Pro Pro Tyr His Pro
145                 150                 155                 160

Ser Ser Glu Lys Tyr Glu Asn Thr Lys Thr Cys Arg Gly Pro Asp Gly
                165                 170                 175

Glu Leu His Ala Asn Leu Leu Cys Pro Val Asp Val Leu Asp Val Pro
            180                 185                 190

Glu Gly Thr Leu Pro Asp Lys Gln Ser Thr Glu Gln Ala Ile Gln Leu
        195                 200                 205

Leu Glu Lys Met Lys Thr Ser Ala Ser Pro Phe Phe Leu Ala Val Gly
    210                 215                 220

Tyr His Lys Pro His Ile Pro Phe Arg Tyr Pro Lys Glu Phe Gln Lys
225                 230                 235                 240

Leu Tyr Pro Leu Glu Asn Ile Thr Leu Ala Pro Asp Pro Glu Val Pro
                245                 250                 255

Asp Gly Leu Pro Pro Val Ala Tyr Asn Pro Trp Met Asp Ile Arg Gln
            260                 265                 270

Arg Glu Asp Val Gln Ala Leu Asn Ile Ser Val Pro Tyr Gly Pro Ile
        275                 280                 285
```

-continued

```
Pro Val Asp Phe Gln Arg Lys Ile Arg Gln Ser Tyr Phe Ala Ser Val
    290                 295                 300

Ser Tyr Leu Asp Thr Gln Val Gly Arg Leu Leu Ser Ala Leu Asp Asp
305                 310                 315                 320

Leu Gln Leu Ala Asn Ser Thr Ile Ile Ala Phe Thr Ser Asp His Gly
                325                 330                 335

Trp Ala Leu Gly Glu His Gly Glu Trp Ala Lys Tyr Ser Asn Phe Asp
                340                 345                 350

Val Ala Thr His Val Pro Leu Ile Phe Tyr Val Pro Gly Arg Thr Ala
            355                 360                 365

Ser Leu Pro Glu Ala Gly Glu Lys Leu Phe Pro Tyr Leu Asp Pro Phe
    370                 375                 380

Asp Ser Ala Ser Gln Leu Met Glu Pro Gly Arg Gln Ser Met Asp Leu
385                 390                 395                 400

Val Glu Leu Val Ser Leu Phe Pro Thr Leu Ala Gly Leu Ala Gly Leu
                405                 410                 415

Gln Val Pro Pro Arg Cys Pro Val Pro Ser Phe His Val Glu Leu Cys
            420                 425                 430

Arg Glu Gly Lys Asn Leu Leu Lys His Phe Arg Phe Arg Asp Leu Glu
    435                 440                 445

Glu Asp Pro Tyr Leu Pro Gly Asn Pro Arg Glu Leu Ile Ala Tyr Ser
    450                 455                 460

Gln Tyr Pro Arg Pro Ser Asp Ile Pro Gln Trp Asn Ser Asp Lys Pro
465                 470                 475                 480

Ser Leu Lys Asp Ile Lys Ile Met Gly Tyr Ser Ile Arg Thr Ile Asp
                485                 490                 495

Tyr Arg Tyr Thr Val Trp Val Gly Phe Asn Pro Asp Glu Phe Leu Ala
            500                 505                 510

Asn Phe Ser Asp Ile His Ala Gly Glu Leu Tyr Phe Val Asp Ser Asp
    515                 520                 525

Pro Leu Gln Asp His Asn Met Tyr Asn Asp Ser Gln Gly Gly Asp Leu
    530                 535                 540

Phe Gln Leu Leu Met Pro
545                 550

<210> SEQ ID NO 7
<211> LENGTH: 533
<212> TYPE: PRT
<213> ORGANISM: artificial sequence
<220> FEATURE:
<223> OTHER INFORMATION: 4-Sulphatase

<400> SEQUENCE: 7

Met Gly Pro Arg Gly Ala Ala Ser Leu Pro Arg Gly Pro Gly Pro Arg
1               5                   10                  15

Arg Leu Leu Leu Pro Val Val Leu Pro Leu Leu Leu Leu Leu Leu Leu
                20                  25                  30

Ala Pro Pro Gly Ser Gly Ala Gly Ala Ser Arg Pro Pro His Leu Val
            35                  40                  45

Phe Leu Leu Ala Asp Asp Leu Gly Trp Asn Asp Val Gly Phe His Gly
    50                  55                  60

Ser Arg Ile Arg Thr Pro His Leu Asp Ala Leu Ala Ala Gly Gly Val
65                  70                  75                  80

Leu Leu Asp Asn Tyr Tyr Thr Gln Pro Leu Cys Thr Pro Ser Arg Ser
                85                  90                  95
```

```
Gln Leu Leu Thr Gly Arg Tyr Gln Ile Arg Thr Gly Leu Gln His Gln
            100                 105                 110

Ile Ile Trp Pro Cys Gln Pro Ser Cys Val Pro Leu Asp Glu Lys Leu
            115                 120                 125

Leu Pro Gln Leu Leu Lys Glu Ala Gly Tyr Thr Thr His Met Val Gly
            130                 135                 140

Lys Trp His Leu Gly Met Tyr Arg Lys Glu Cys Leu Pro Thr Arg Arg
145                 150                 155                 160

Gly Phe Asp Thr Tyr Phe Gly Tyr Leu Leu Gly Ser Glu Asp Tyr Tyr
                165                 170                 175

Ser His Glu Arg Cys Thr Leu Ile Asp Ala Leu Asn Val Thr Arg Cys
            180                 185                 190

Ala Leu Asp Phe Arg Asp Gly Glu Val Ala Thr Gly Tyr Lys Asn
            195                 200                 205

Met Tyr Ser Thr Asn Ile Phe Thr Lys Arg Ala Ile Ala Leu Ile Thr
            210                 215                 220

Asn His Pro Pro Glu Lys Pro Leu Phe Leu Tyr Leu Ala Leu Gln Ser
225                 230                 235                 240

Val His Glu Pro Leu Gln Val Pro Glu Glu Tyr Leu Lys Pro Tyr Asp
                245                 250                 255

Phe Ile Gln Asp Lys Asn Arg His His Tyr Ala Gly Met Val Ser Leu
            260                 265                 270

Met Asp Glu Ala Val Gly Asn Val Thr Ala Ala Leu Lys Ser Ser Gly
            275                 280                 285

Leu Trp Asn Asn Thr Val Phe Ile Phe Ser Thr Asp Asn Gly Gly Gln
            290                 295                 300

Thr Leu Ala Gly Gly Asn Asn Trp Pro Leu Arg Gly Arg Lys Trp Ser
305                 310                 315                 320

Leu Trp Glu Gly Gly Val Arg Gly Val Gly Phe Val Ala Ser Pro Leu
                325                 330                 335

Leu Lys Gln Lys Gly Val Lys Asn Arg Glu Leu Ile His Ile Ser Asp
            340                 345                 350

Trp Leu Pro Thr Leu Val Lys Leu Ala Arg Gly His Thr Asn Gly Thr
            355                 360                 365

Lys Pro Leu Asp Gly Phe Asp Val Trp Lys Thr Ile Ser Glu Gly Ser
            370                 375                 380

Pro Ser Pro Arg Ile Glu Leu Leu His Asn Ile Asp Pro Asn Phe Val
385                 390                 395                 400

Asp Ser Ser Pro Cys Pro Arg Asn Ser Met Ala Pro Ala Lys Asp Asp
                405                 410                 415

Ser Ser Leu Pro Glu Tyr Ser Ala Phe Asn Thr Ser Val His Ala Ala
            420                 425                 430

Ile Arg His Gly Asn Trp Lys Leu Leu Thr Gly Tyr Pro Gly Cys Gly
            435                 440                 445

Tyr Trp Phe Pro Pro Ser Gln Tyr Asn Val Ser Glu Ile Pro Ser
450                 455                 460

Ser Asp Pro Pro Thr Lys Thr Leu Trp Leu Phe Asp Ile Asp Arg Asp
465                 470                 475                 480

Pro Glu Glu Arg His Asp Leu Ser Arg Glu Tyr Pro His Ile Val Thr
                485                 490                 495

Lys Leu Leu Ser Arg Leu Gln Phe Tyr His Lys His Ser Val Pro Val
            500                 505                 510
```

Tyr Phe Pro Ala Gln Asp Pro Arg Cys Asp Pro Lys Ala Thr Gly Val
            515                 520                 525

Trp Gly Pro Trp Met
    530

<210> SEQ ID NO 8
<211> LENGTH: 429
<212> TYPE: PRT
<213> ORGANISM: artificial sequence
<220> FEATURE:
<223> OTHER INFORMATION: Amino Acid sequence for alpha-galactosidase.

<400> SEQUENCE: 8

Met Gln Leu Arg Asn Pro Glu Leu His Leu Gly Cys Ala Leu Ala Leu
1               5                   10                  15

Arg Phe Leu Ala Leu Val Ser Trp Asp Ile Pro Gly Ala Arg Ala Leu
            20                  25                  30

Asp Asn Gly Leu Ala Arg Thr Pro Thr Met Gly Trp Leu His Trp Glu
        35                  40                  45

Arg Phe Met Cys Asn Leu Asp Cys Gln Glu Glu Pro Asp Ser Cys Ile
    50                  55                  60

Ser Glu Lys Leu Phe Met Glu Met Ala Glu Leu Met Val Ser Glu Gly
65                  70                  75                  80

Trp Lys Asp Ala Gly Tyr Glu Tyr Leu Cys Ile Asp Asp Cys Trp Met
                85                  90                  95

Ala Pro Gln Arg Asp Ser Glu Gly Arg Leu Gln Ala Asp Pro Gln Arg
            100                 105                 110

Phe Pro His Gly Ile Arg Gln Leu Ala Asn Tyr Val His Ser Lys Gly
        115                 120                 125

Leu Lys Leu Gly Ile Tyr Ala Asp Val Gly Asn Lys Thr Cys Ala Gly
    130                 135                 140

Phe Pro Gly Ser Phe Gly Tyr Tyr Asp Ile Asp Ala Gln Thr Phe Ala
145                 150                 155                 160

Asp Trp Gly Val Asp Leu Leu Lys Phe Asp Gly Cys Tyr Cys Asp Ser
                165                 170                 175

Leu Glu Asn Leu Ala Asp Gly Tyr Lys His Met Ser Leu Ala Leu Asn
            180                 185                 190

Arg Thr Gly Arg Ser Ile Val Tyr Ser Cys Glu Trp Pro Leu Tyr Met
        195                 200                 205

Trp Pro Phe Gln Lys Pro Asn Tyr Thr Glu Ile Arg Gln Tyr Cys Asn
    210                 215                 220

His Trp Arg Asn Phe Ala Asp Ile Asp Asp Ser Trp Lys Ser Ile Lys
225                 230                 235                 240

Ser Ile Leu Asp Trp Thr Ser Phe Asn Gln Glu Arg Ile Val Asp Val
                245                 250                 255

Ala Gly Pro Gly Gly Trp Asn Asp Pro Asp Met Leu Val Ile Gly Asn
            260                 265                 270

Phe Gly Leu Ser Trp Asn Gln Gln Val Thr Gln Met Ala Leu Trp Ala
        275                 280                 285

Ile Met Ala Ala Pro Leu Phe Met Ser Asn Asp Leu Arg His Ile Ser
    290                 295                 300

Pro Gln Ala Lys Ala Leu Leu Gln Asp Lys Asp Val Ile Ala Ile Asn
305                 310                 315                 320

Gln Asp Pro Leu Gly Lys Gln Gly Tyr Gln Leu Arg Gln Gly Asp Asn
                325                 330                 335

```
Phe Glu Val Trp Glu Arg Pro Leu Ser Gly Leu Ala Trp Ala Val Ala
                340                 345                 350

Met Ile Asn Arg Gln Glu Ile Gly Gly Pro Arg Ser Tyr Thr Ile Ala
            355                 360                 365

Val Ala Ser Leu Gly Lys Gly Val Ala Cys Asn Pro Ala Cys Phe Ile
        370                 375                 380

Thr Gln Leu Leu Pro Val Lys Arg Lys Leu Gly Phe Tyr Glu Trp Thr
385                 390                 395                 400

Ser Arg Leu Arg Ser His Ile Asn Pro Thr Gly Thr Val Leu Leu Gln
                405                 410                 415

Leu Glu Asn Thr Met Gln Met Ser Leu Lys Asp Leu Leu
                420                 425

<210> SEQ ID NO 9
<211> LENGTH: 629
<212> TYPE: PRT
<213> ORGANISM: artificial sequence
<220> FEATURE:
<223> OTHER INFORMATION: Amino Acid sequence for sphingomyelinase.

<400> SEQUENCE: 9

Met Pro Arg Tyr Gly Ala Ser Leu Arg Gln Ser Cys Pro Arg Ser Gly
1               5                   10                  15

Arg Glu Gln Gly Gln Asp Gly Thr Ala Gly Ala Pro Gly Leu Leu Trp
                20                  25                  30

Met Gly Leu Val Leu Ala Leu Ala Leu Ala Leu Ala Leu Ala Leu Ser
            35                  40                  45

Asp Ser Arg Val Leu Trp Ala Pro Ala Glu Ala His Pro Leu Ser Pro
        50                  55                  60

Gln Gly His Pro Ala Arg Leu His Arg Ile Val Pro Arg Leu Arg Asp
65                  70                  75                  80

Val Phe Gly Trp Gly Asn Leu Thr Cys Pro Ile Cys Lys Gly Leu Phe
                85                  90                  95

Thr Ala Ile Asn Leu Gly Leu Lys Lys Glu Pro Asn Val Ala Arg Val
            100                 105                 110

Gly Ser Val Ala Ile Lys Leu Cys Asn Leu Leu Lys Ile Ala Pro Pro
        115                 120                 125

Ala Val Cys Gln Ser Ile Val His Leu Phe Glu Asp Asp Met Val Glu
    130                 135                 140

Val Trp Arg Arg Ser Val Leu Ser Pro Ser Glu Ala Cys Gly Leu Leu
145                 150                 155                 160

Leu Gly Ser Thr Cys Gly His Trp Asp Ile Phe Ser Ser Trp Asn Ile
                165                 170                 175

Ser Leu Pro Thr Val Pro Lys Pro Pro Lys Pro Ser Pro Pro
            180                 185                 190

Ala Pro Gly Ala Pro Val Ser Arg Ile Leu Phe Leu Thr Asp Leu His
        195                 200                 205

Trp Asp His Asp Tyr Leu Glu Gly Thr Asp Pro Asp Cys Ala Asp Pro
    210                 215                 220

Leu Cys Cys Arg Arg Gly Ser Gly Leu Pro Pro Ala Ser Arg Pro Gly
225                 230                 235                 240

Ala Gly Tyr Trp Gly Glu Tyr Ser Lys Cys Asp Leu Pro Leu Arg Thr
                245                 250                 255

Leu Glu Ser Leu Leu Ser Gly Leu Gly Pro Ala Gly Pro Phe Asp Met
            260                 265                 270
```

```
Val Tyr Trp Thr Gly Asp Ile Pro Ala His Asp Val Trp His Gln Thr
        275                 280                 285

Arg Gln Asp Gln Leu Arg Ala Leu Thr Thr Val Thr Ala Leu Val Arg
        290                 295                 300

Lys Phe Leu Gly Pro Val Pro Val Tyr Pro Ala Val Gly Asn His Glu
305                 310                 315                 320

Ser Thr Pro Val Asn Ser Phe Pro Pro Phe Ile Glu Gly Asn His
                325                 330                 335

Ser Ser Arg Trp Leu Tyr Glu Ala Met Ala Lys Ala Trp Glu Pro Trp
        340                 345                 350

Leu Pro Ala Glu Ala Leu Arg Thr Leu Arg Ile Gly Phe Tyr Ala
        355                 360                 365

Leu Ser Pro Tyr Pro Gly Leu Arg Leu Ile Ser Leu Asn Met Asn Phe
        370                 375                 380

Cys Ser Arg Glu Asn Phe Trp Leu Leu Ile Asn Ser Thr Asp Pro Ala
385                 390                 395                 400

Gly Gln Leu Gln Trp Leu Val Gly Glu Leu Gln Ala Ala Glu Asp Arg
        405                 410                 415

Gly Asp Lys Val His Ile Ile Gly His Ile Pro Pro Gly His Cys Leu
        420                 425                 430

Lys Ser Trp Ser Trp Asn Tyr Tyr Arg Ile Val Ala Arg Tyr Glu Asn
        435                 440                 445

Thr Leu Ala Ala Gln Phe Phe Gly His Thr His Val Asp Glu Phe Glu
        450                 455                 460

Val Phe Tyr Asp Glu Glu Thr Leu Ser Arg Pro Leu Ala Val Ala Phe
465                 470                 475                 480

Leu Ala Pro Ser Ala Thr Thr Tyr Ile Gly Leu Asn Pro Gly Tyr Arg
        485                 490                 495

Val Tyr Gln Ile Asp Gly Asn Tyr Ser Arg Ser Ser His Val Val Leu
                500                 505                 510

Asp His Glu Thr Tyr Ile Leu Asn Leu Thr Gln Ala Asn Ile Pro Gly
        515                 520                 525

Ala Ile Pro His Trp Gln Leu Leu Tyr Arg Ala Arg Glu Thr Tyr Gly
        530                 535                 540

Leu Pro Asn Thr Leu Pro Thr Ala Trp His Asn Leu Val Tyr Arg Met
545                 550                 555                 560

Arg Gly Asp Met Gln Leu Phe Gln Thr Phe Trp Phe Leu Tyr His Lys
                565                 570                 575

Gly His Pro Pro Ser Glu Pro Cys Gly Thr Pro Cys Arg Leu Ala Thr
        580                 585                 590

Leu Cys Ala Gln Leu Ser Ala Arg Ala Asp Ser Pro Ala Leu Cys Arg
        595                 600                 605

His Leu Met Pro Asp Gly Ser Leu Pro Glu Ala Gln Ser Leu Trp Pro
        610                 615                 620

Arg Pro Leu Phe Cys
625

<210> SEQ ID NO 10
<211> LENGTH: 507
<212> TYPE: PRT
<213> ORGANISM: artificial sequence
<220> FEATURE:
<223> OTHER INFORMATION: Amino Acid sequence for 3-Sulphatase.

<400> SEQUENCE: 10
```

-continued

```
Met Gly Ala Pro Arg Ser Leu Leu Ala Leu Ala Ala Gly Leu Ala
 1               5                  10                  15

Val Ala Arg Pro Pro Asn Ile Val Leu Ile Phe Ala Asp Asp Leu Gly
             20                  25                  30

Tyr Gly Asp Leu Gly Cys Tyr Gly His Pro Ser Ser Thr Thr Pro Asn
         35                  40                  45

Leu Asp Gln Leu Ala Ala Gly Leu Arg Phe Thr Asp Phe Tyr Val
     50                  55                  60

Pro Val Ser Leu Cys Thr Pro Ser Arg Ala Ala Leu Leu Thr Gly Arg
 65                  70                  75                  80

Leu Pro Val Arg Met Gly Met Tyr Pro Gly Val Leu Val Pro Ser Ser
                 85                  90                  95

Arg Gly Gly Leu Pro Leu Glu Glu Val Thr Val Ala Glu Val Leu Ala
                100                 105                 110

Ala Arg Gly Tyr Leu Thr Gly Met Ala Gly Lys Trp His Leu Gly Val
             115                 120                 125

Gly Pro Glu Gly Ala Phe Leu Pro Pro His Gln Gly Phe His Arg Phe
         130                 135                 140

Leu Gly Ile Pro Tyr Ser His Asp Gln Gly Pro Cys Gln Asn Leu Thr
145                 150                 155                 160

Cys Phe Pro Pro Ala Thr Pro Cys Asp Gly Cys Asp Gln Gly Leu
                 165                 170                 175

Val Pro Ile Pro Leu Leu Ala Asn Leu Ser Val Glu Ala Gln Pro Pro
             180                 185                 190

Trp Leu Pro Gly Leu Glu Ala Arg Tyr Met Ala Phe Ala His Asp Leu
         195                 200                 205

Met Ala Asp Ala Gln Arg Gln Asp Arg Pro Phe Phe Leu Tyr Tyr Ala
    210                 215                 220

Ser His His Thr His Tyr Pro Gln Phe Ser Gly Gln Ser Phe Ala Glu
225                 230                 235                 240

Arg Ser Gly Arg Gly Pro Phe Gly Asp Ser Leu Met Glu Leu Asp Ala
                245                 250                 255

Ala Val Gly Thr Leu Met Thr Ala Ile Gly Asp Leu Gly Leu Leu Glu
            260                 265                 270

Glu Thr Leu Val Ile Phe Thr Ala Asp Asn Gly Pro Glu Thr Met Arg
        275                 280                 285

Met Ser Arg Gly Gly Cys Ser Gly Leu Leu Arg Cys Gly Lys Gly Thr
    290                 295                 300

Thr Tyr Glu Gly Gly Val Arg Glu Pro Ala Leu Ala Phe Trp Pro Gly
305                 310                 315                 320

His Ile Ala Pro Gly Val Thr His Glu Leu Ala Ser Ser Leu Asp Leu
                325                 330                 335

Leu Pro Thr Leu Ala Ala Leu Ala Gly Ala Pro Leu Pro Asn Val Thr
            340                 345                 350

Leu Asp Gly Phe Asp Leu Ser Pro Leu Leu Leu Gly Thr Gly Lys Ser
        355                 360                 365

Pro Arg Gln Ser Leu Phe Phe Tyr Pro Ser Tyr Pro Asp Glu Val Arg
    370                 375                 380

Gly Val Phe Ala Val Arg Thr Gly Lys Tyr Lys Ala His Phe Phe Thr
385                 390                 395                 400

Gln Gly Ser Ala His Ser Asp Thr Thr Ala Asp Pro Ala Cys His Ala
                405                 410                 415

Ser Ser Ser Leu Thr Ala His Glu Pro Pro Leu Leu Tyr Asp Leu Ser
```

-continued

```
                    420                 425                 430
Lys Asp Pro Gly Glu Asn Tyr Asn Leu Leu Gly Val Ala Gly Ala
        435                 440                 445

Thr Pro Glu Val Leu Gln Ala Leu Lys Gln Leu Gln Leu Leu Lys Ala
    450                 455                 460

Gln Leu Asp Ala Ala Val Thr Phe Gly Pro Ser Gln Val Ala Arg Gly
465                 470                 475                 480

Glu Asp Pro Ala Leu Gln Ile Cys Cys His Pro Gly Cys Thr Pro Arg
                485                 490                 495

Pro Ala Cys Cys His Cys Pro Asp Pro His Ala
            500                 505
```

MULTIPLEX-BEAD COMPLEX FOR DETERMINATION OF LYSOSOMAL STORAGE DISORDERS

RELATED APPLICATIONS

This application claims priority to U.S. Provisional Patent Application, Ser. No. 60/632,610, entitled "Multiplex-Bead Complex for Determination of Lysosomal Storage Disorders," filed on Dec. 2, 2004, having Meikle et al., listed as the inventor(s), the entire content of which is hereby incorporated by reference.

BACKGROUND

The present invention generally pertains to a process of population screening that leads to the detection of Lysosomal Storage Disorders ("LSDs") and related diseases in a subject. More particularly, this invention pertains to compounds, reagents, and methods for identifying and quantifying the levels and ratios of multiple target antigens that are used to identify individuals likely to be affect with an LSD. The target antigens are naturally present in biological fluids or tissues of either LSD or non-LSD patients.

LSDs represent a group of over 40 distinct genetic diseases that generally affect young children. Individuals that are affected with a LSD present a wide range of clinical symptoms that depend upon the specific disorder or a particular genotype involved. The clinical symptoms associated with LSD's can have a devastating impact on both the child and the family of affected individuals. For example, central nervous system dysfunction, behavioral problems, and severe mental retardation are characteristic of many LSDs. Other clinical symptoms may include skeletal abnormalities, organomegaly, corneal clouding and dysmorphic features (Neufeld and Muenzer, 1995). Patients are usually born without the visible features of a LSD, but early stage symptoms can quickly develop into a progressive clinical concern. In severe cases, the affected children require constant medical management but still often die before adolescence.

The significance of LSDs to health care becomes obvious when comparing the group incidence rate for a LSD (1:5,000 births) to the group incidence rate of other with well-known and intensively studied genetic disorders, such as phenylketonuria (1:14,000) and cystic fibrosis (1:2,500), wherein these figures reflect incidence rates for Caucasian populations.

Once an individual begins to present the symptoms of a LSD, the actual clinical diagnosis of the disease is still a complex process. A clinical diagnosis of a LSD often requires multiple visits to a range of specialists, which can take months or even years. This long process is extremely stressful on the patient and family. Fortunately, there has been considerable progress in the diagnosis of LSDs over the past 20 years. For example, the development and introduction of chromatographic-based urine screens for a specific group of LSDs called mucopolysaccharidoses ("MPS") and oligosaccharidoses has facilitated screening of clinically selected patients for these disorders. Following a clinical index of suspicion for the disorders, the next stage of diagnosis involves a urine screen, wherein a "positive" urine screen is then followed by specific enzymatic analysis. Although the chromatographic-based screening methods are simple to perform, they are relatively labor-intensive and often require experience to accurately interpret results. One example includes a method of identifying and quantitating biochemical markers ("biomarkers") that are present in biological fluids or tissues of a patient having a MPS or related disorders comprises determining a target quantity of a target MPS biomarker oligosaccharide from a target biological sample taken from the target animal, and then comparing the target quantity to a reference quantity of a reference MPS biomarker oligosaccharide for the diagnosis, characterization, monitoring, and clinical management of MPS and related disease, as described in PCT Application AU03/00731 entitled "Identification of Oligosaccharides and their Use in the Diagnosis and Evaluation of Mucopolysaccharidoses and Other Related Disorders," filed on Jun. 13, 2003 with Hopwood et al., listed as inventors (the entire content of PCT Application AU03/00731 is hereby incorporated by reference). Consequently, chromatographic-based screening tests for LSDs are not used in some centers. Furthermore, these chromatographic-based screens are not readily amenable to automation, which has further limited their utilization in screening strategies for newborns.

The production of specific substrates and antibody capture assays has made the enzymatic analyses for LSDs more accurate. Although not wanting to be bound by theory, the majority of LSDs result from a reduction in levels of a particular enzyme(s) involved in a specific LSD, and the identification of the specific enzyme(s) steady state in normal individuals will help identify the particular form of LSD in the affected individual. The ability to quickly and accurately determine the levels of the more than 40 enzymes known to be involved with LSDs will assist in the development of better and more economical screening assays. Unfortunately, many of the chromatographic-based screens and enzyme assays mentioned above are time-consuming, invasive, complex, and require cultured cells, or tissue biopsies, which tends to make such assays inconvenient and expensive. As a result, testing for a LSD is often not a first line strategy for an affected child with early stage symptoms. Newborn screening for LSDs promises to provide early detection of the LSD, but all newborns must be screened in order to detect the disease early. Patients having a family history of LSDs may have a justifiable reason to perform an early screen for a LSD. However, the cost of an early screen of the LSD in individuals not having a family history may not be justified economically. Therefore, it would be beneficial that any LSD screening process be capable of economically screening large numbers of newborns.

One common feature of LSDs is the accumulation and storage of materials within lysosomes. It is generally recognized that the accumulation and storage of material in LSD affected individuals results in an increase in the number and the size of lysosomes within a cell from approximately 1% to as much as 50% of total cellular volume. In non-affected individuals, such materials are typically degraded into degradation products within the lysosome and then transported across the lysosomal membrane. Certain lysosomal proteins are present at elevated levels in the lysosomes of affected individuals (Meikle et al., 1997; Hua et al., 1998). These identified proteins are useful biomarkers for an early diagnosis of all LSDs. For example, sensitive immunoquantification assays have been developed to monitor the level of useful biomarkers such as the lysosome-associated membrane proteins ("LAMPs"), saposins, and α-glucosidase. Although the determination of either LAMP-1 or LAMP-2 levels alone in an 'at-increased-risk' group will identify up to 65% of LSD affected individuals, the combination of a LAMP with one of the saposins increase identification of LSD affected individuals to approximately 85%. Therefore, a method to identify two or more biomarkers simultaneously would increase the accuracy of diagnosing a specific LSD as compared to any single assay. An automated multiplex assay that could perform a simultaneous screen on each of the known LSD deficient enzymes would reduce time and cost for accurate LSD diagnosis.

Multiplexing Bead Technology is built around 3 core technologies. The first is the family of fluorescently dyed microspheres having specific biomolecules bound to the surface of the microsphere. The second is a flow cytometer with 2 lasers and associated optics to measure biochemical reactions that occur on the surface of the microspheres, and the third is a high-speed digital signal processor to efficiently manage the fluorescent output. This type of system has been described in, for example: U.S. Pat. Nos. 6,449,562; 6,524,793 and U.S. patent application Ser. No. 09/956,857. U.S. Pat. No. 6,449,562 ("the '562 Patent") entitled "Multiplexed Analysis of Clinical Specimens Apparatus and Method," having Chandler et al. listed as inventors was issued on Sep. 10, 2002. The '562 Patent discloses a method for the multiplexed diagnostic and genetic analysis of enzymes, DNA fragments, antibodies, and other biomolecules comprising the steps of constructing an appropriately labeled beadset, exposing the beadset to a clinical sample, and analyzing the combined sample/beadset by flow cytometry. Flow cytometric measurements are used to classify, in real-time, beads within an exposed beadset and textual explanations, based on the accumulated data obtained during real-time analysis, are generated for the user. The inventive technology of the '562 Patent enables the simultaneous, and automated, detection and interpretation of multiple biomolecules or DNA sequences in real-time while also reducing the cost of performing diagnostic and genetic assays. However, the '562 Patent does not describe how to utilize the technology for diagnosing LSD's.

U.S. Pat. No. 6,524,793 ("the '793 Patent") entitled "Multiplexed Analysis of Clinical Specimens Apparatus and Method," having Chandler et al. listed as inventors, was issued on Feb. 25, 2003. The '793 Patent discloses a method for the multiplexed diagnostic and genetic analysis of enzymes, DNA fragments, antibodies, and other biomolecules comprising the steps of constructing an appropriately labeled beadset, exposing the beadset to a clinical sample, and analyzing the combined sample/beadset by flow cytometry. Flow cytometric measurements are used to classify, in realtime, beads within an exposed beadset and textual explanations, based on the accumulated data obtained during realtime analysis, are generated for the user. The '793 Patent enables the simultaneous, and automated, detection and interpretation of multiple biomolecules or DNA sequences in realtime while also reducing the cost of performing diagnostic and genetic assays. However, the '793 Patent does not describe how to utilize the technology for diagnosing LSD's.

U.S. patent application Ser. No. 09/956,857 ("the '857 Application") entitled "Multiple Reporter Read-out for Bioassays" was published on Mar. 20, 2003. The '857 Application describes a method for detecting a plurality of reactive sites on an analyte, comprising allowing reactants on an addressable microsphere and the reactive sites to react, forming reactant-reactive site pairs distinguishable by fluorescence intensity. The '857 Application also provides a method for detecting a plurality of analytes in a sample using addressable microspheres in combination with one or more reporter reagents. Also provided is a method for determining allele zygosity of a genetic locus having two alleles or more alleles using microparticles, and a method for detecting a plurality of SNPs in nucleic acid molecules. The '857 Application also provides a composition comprising an addressable microsphere carrying at least two fluorescent reactants capable of forming reactant-analyte pairs distinguishable by their fluorescence intensity, and kits comprising the inventive composition and a plurality of reporter reagents. However, the '857 Application does not describe how to utilize the technology for diagnosing LSD's. The entirety of each of the applications or patents listed above is hereby specifically incorporated by reference.

Accordingly, there is a need for the development of a fast, accurate and economical screen for early diagnosis of LSDs, which is amenable to automation. The ability to identify specific LSD enzymes in an automated multiplex assay will have a significant impact on the development of a newborn screening programs, as well as the ability to address a number of other issues associated with the early diagnosis and treatment of LSDs. The present invention provides compounds, reagents, and methods for a LSD diagnostic multiplex assay.

FIGURES

FIG. 7 shows the antibodies and bead regions used for the 10-plex assay;

FIG. 8 shows a list of the precision studies that were conducted on the 11-plex;

FIG. 9 shows the Intra and Inter assay percentage CV for the 11-plex;

FIG. 10 shows protein markers for LSD screening using multiplex assays for LSD;

FIG. 17 shows Validation of the Multiplex Newborn Screening Assay;

FIG. 18 shows Assay performance during validation studies;

Figure 19:
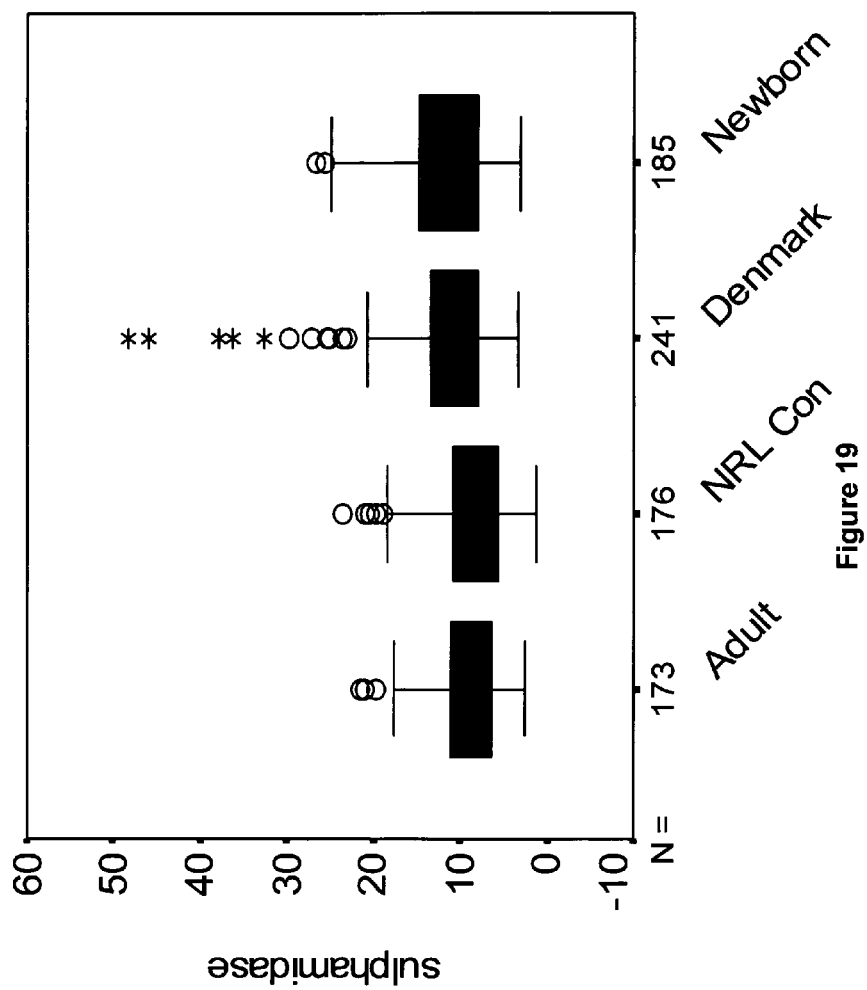
Figure 20:
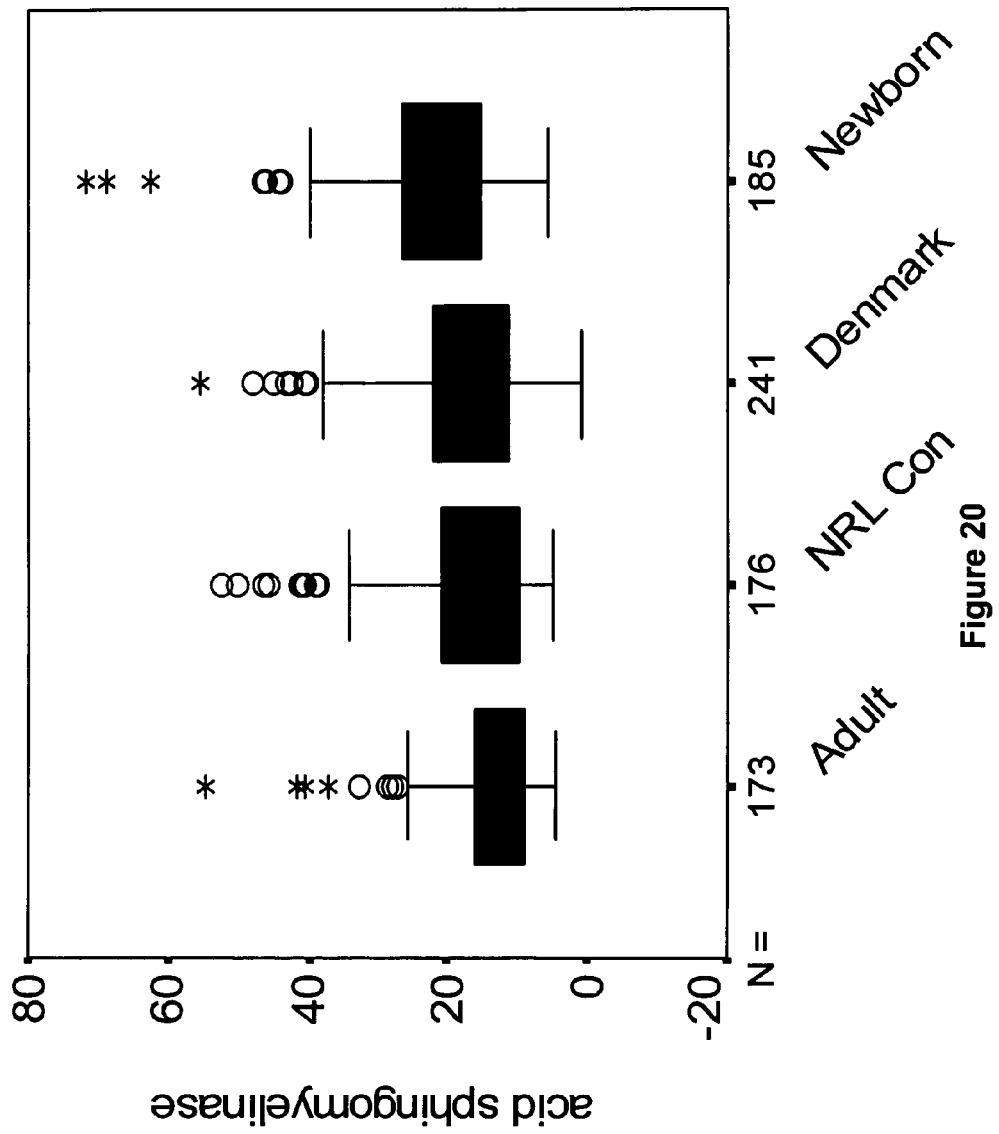
Figure 21:
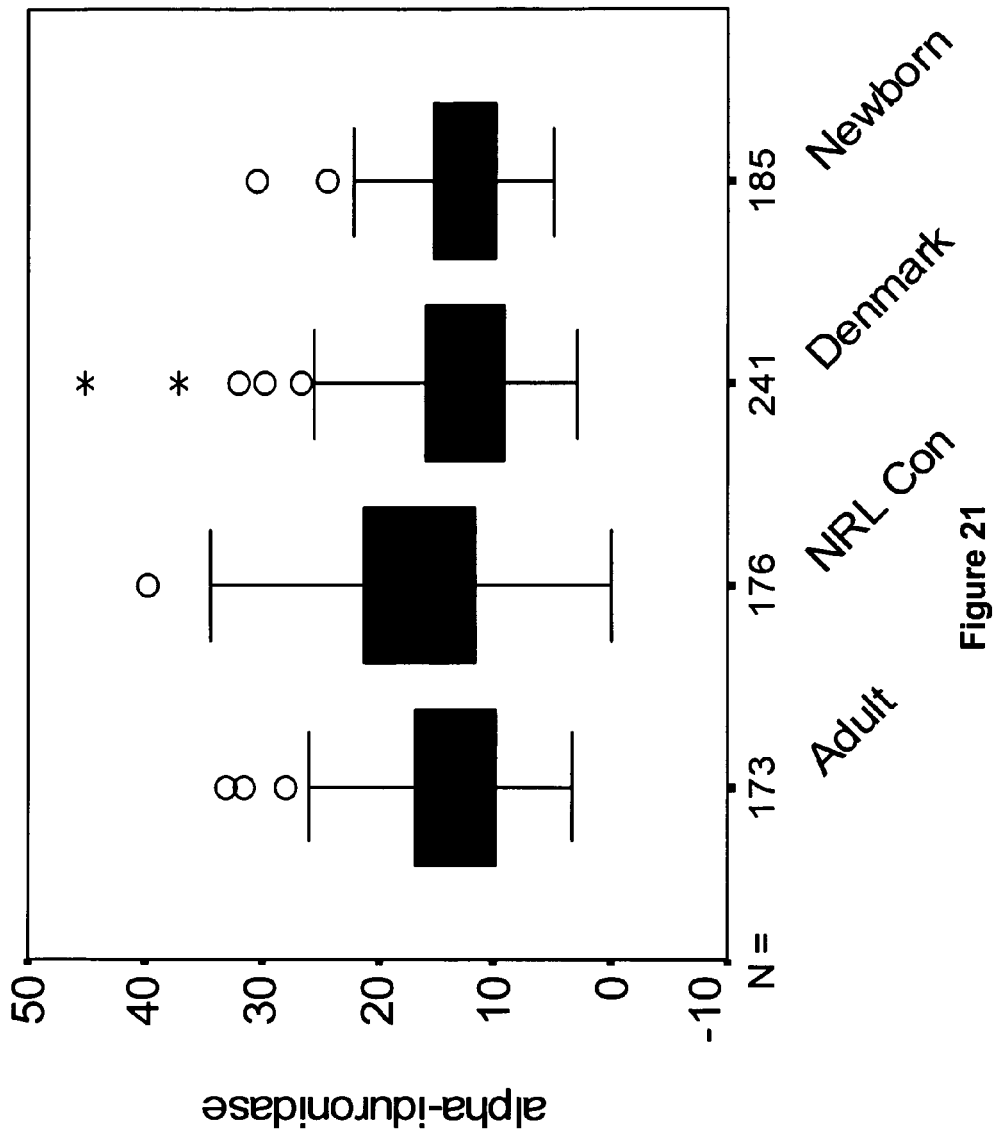
Figure 22:
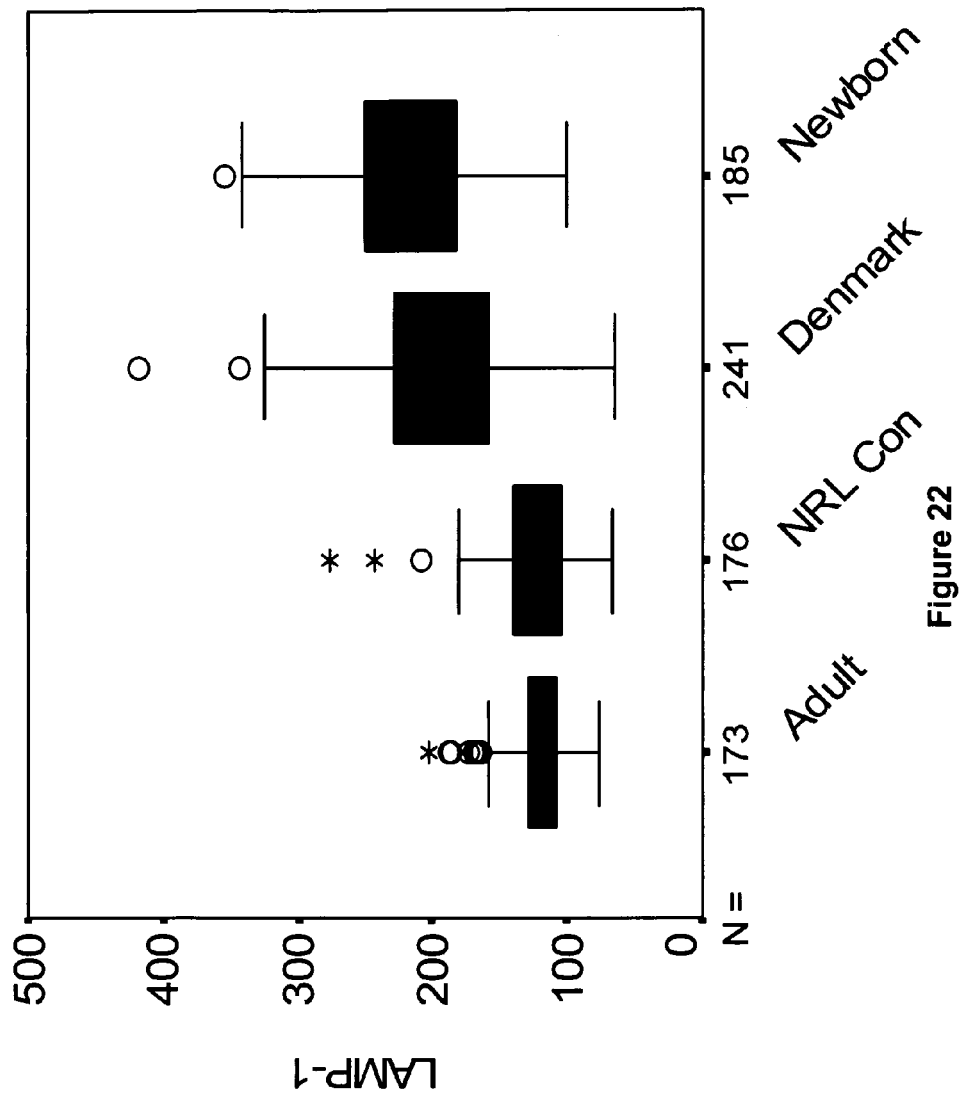
Figure 23:
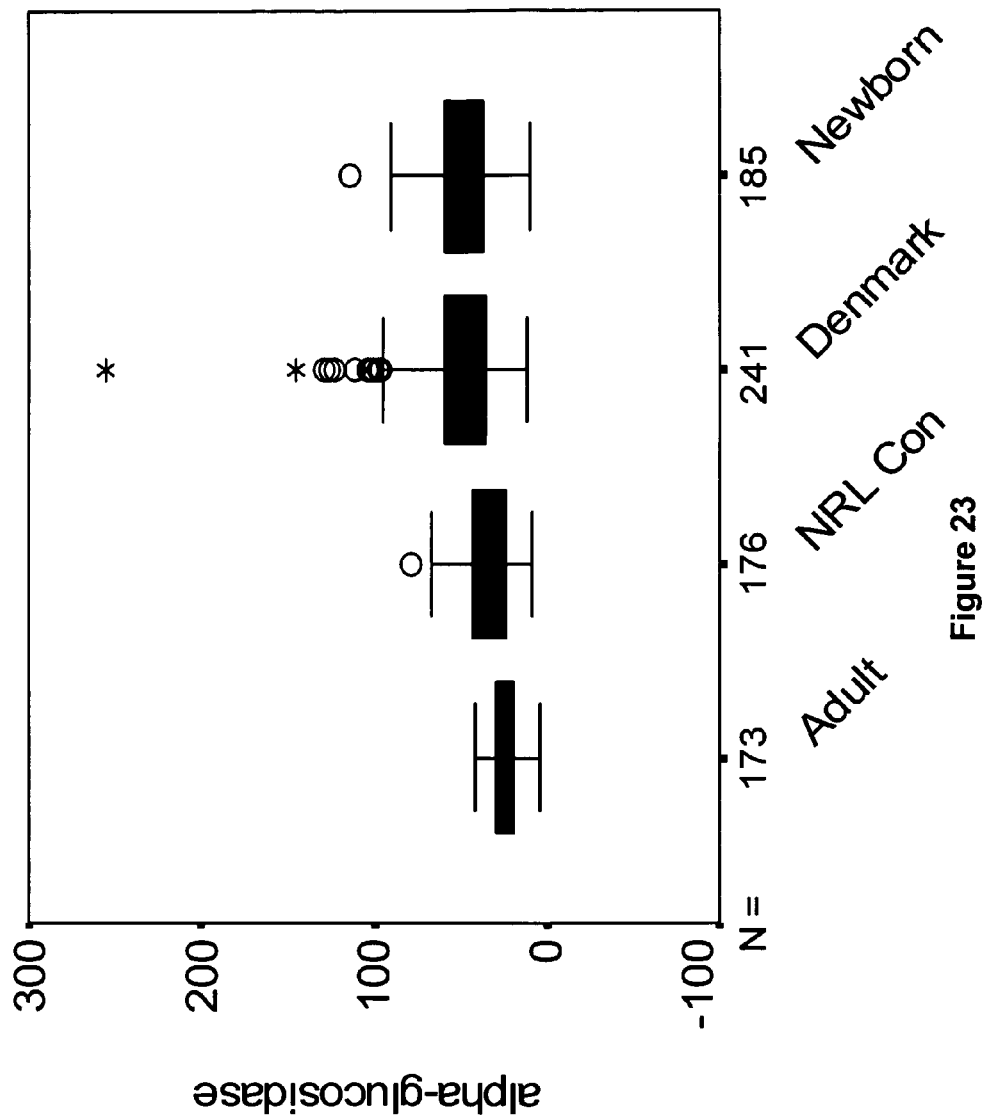
Figure 24:
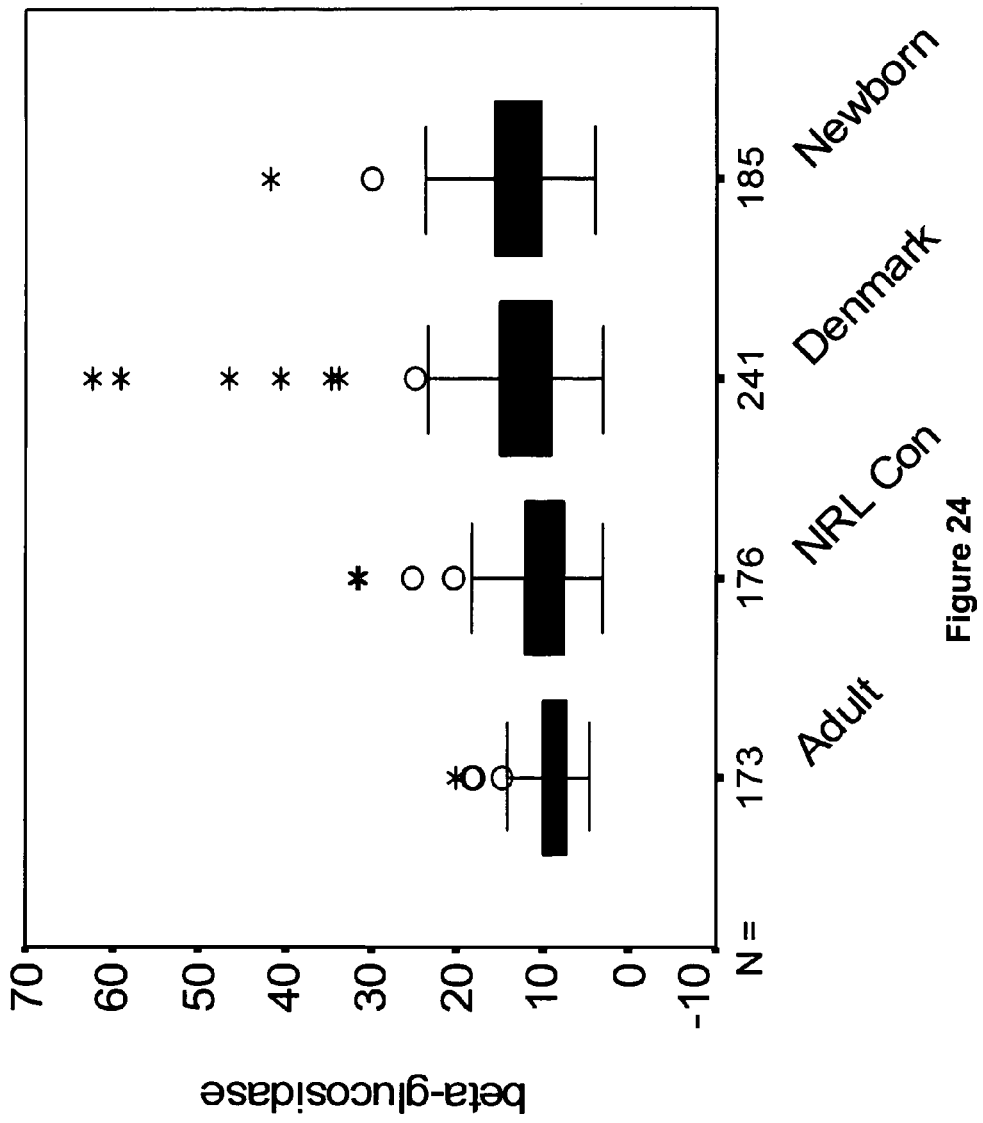
Figure 25:
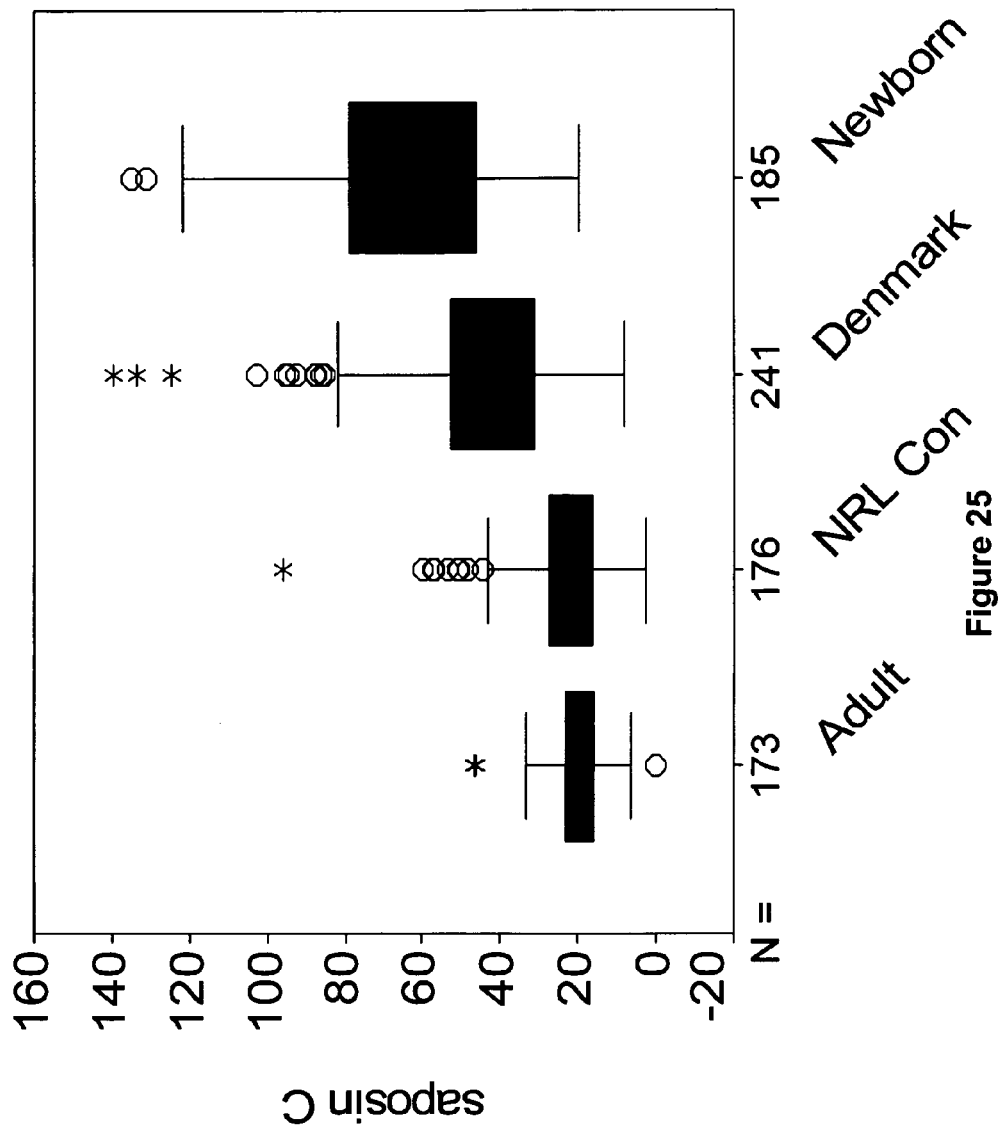
Figure 26:
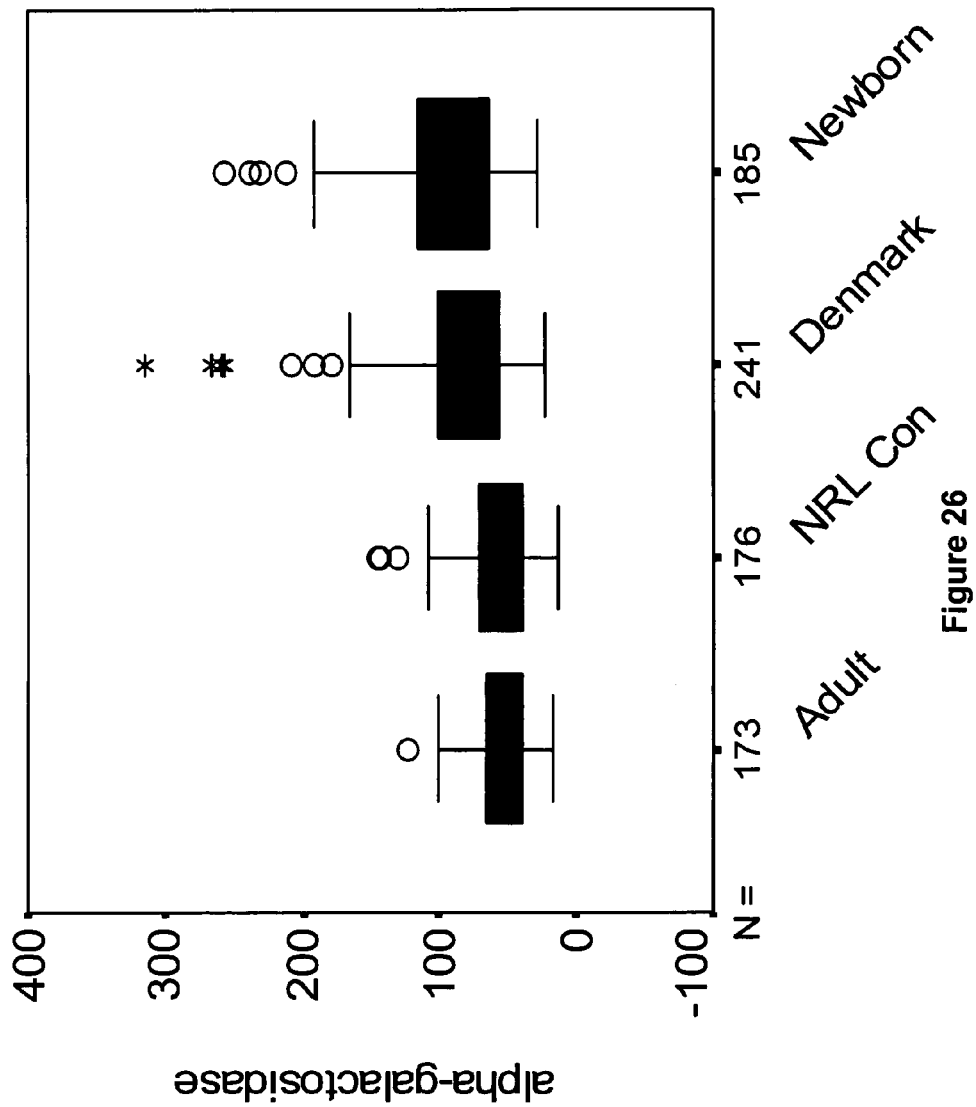
Figure 27:
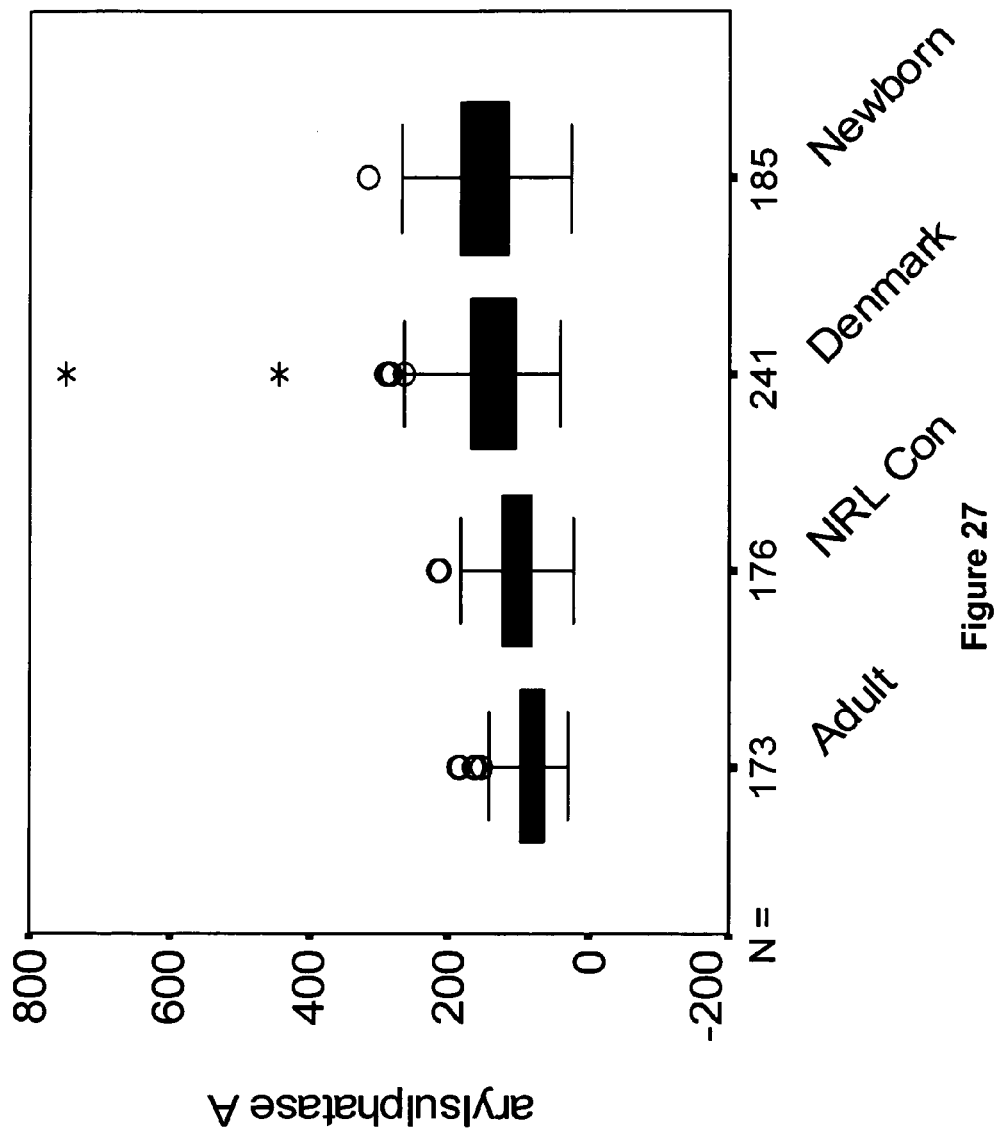
Figure 28:
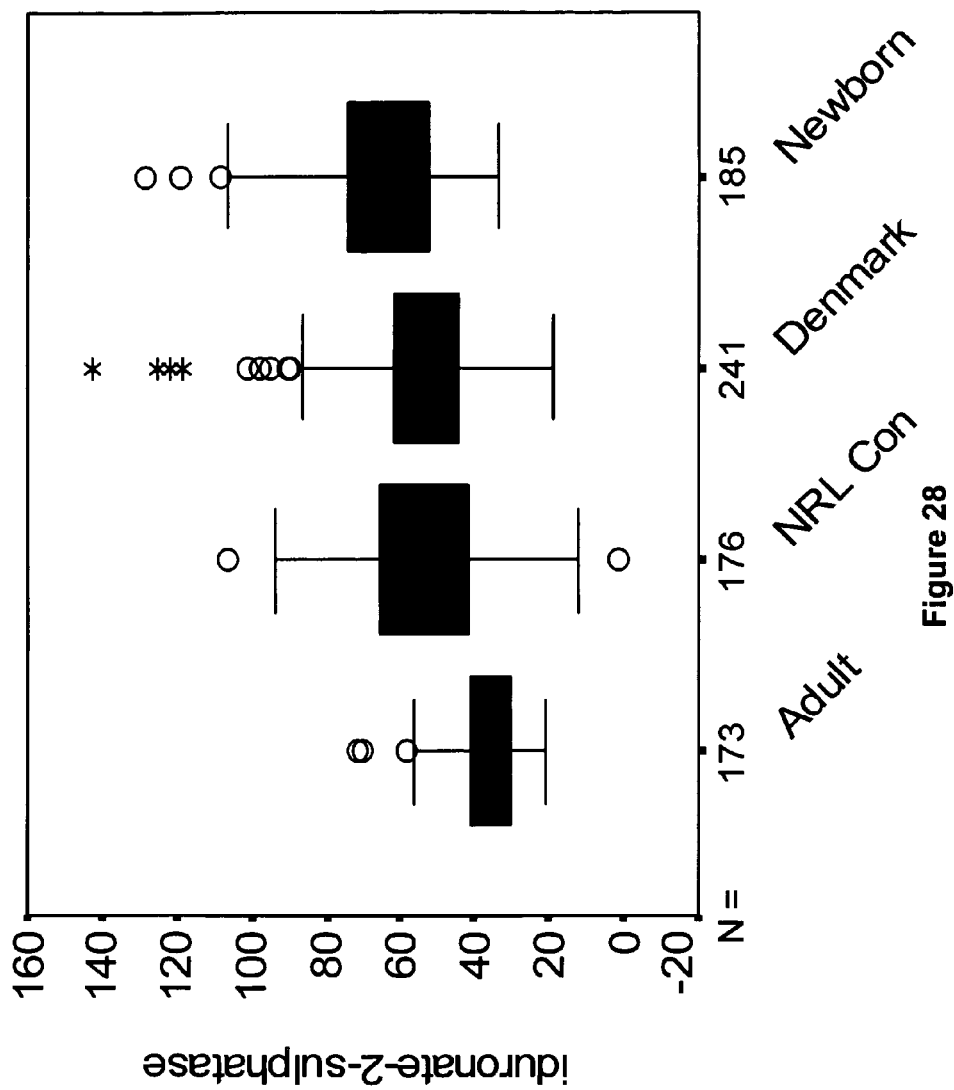
Figure 29:
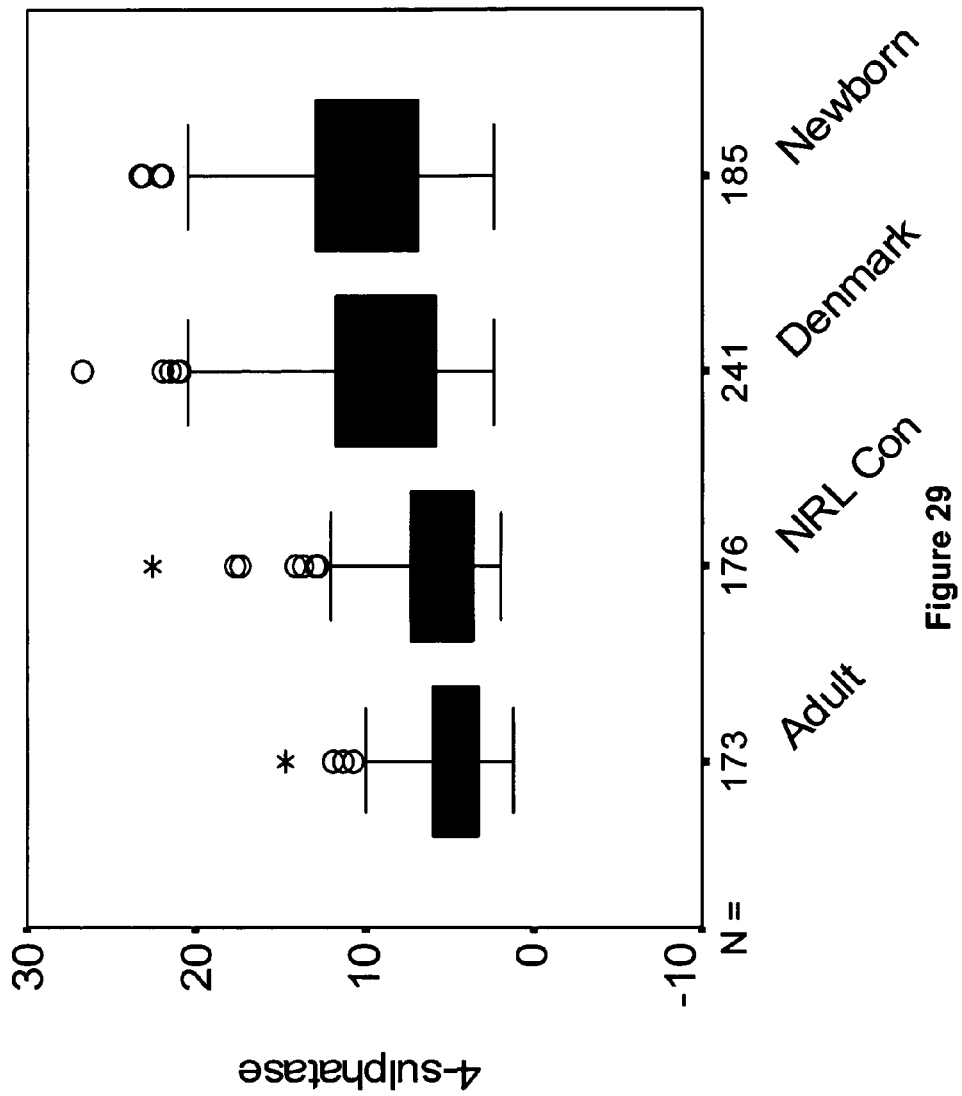
Figure 30:
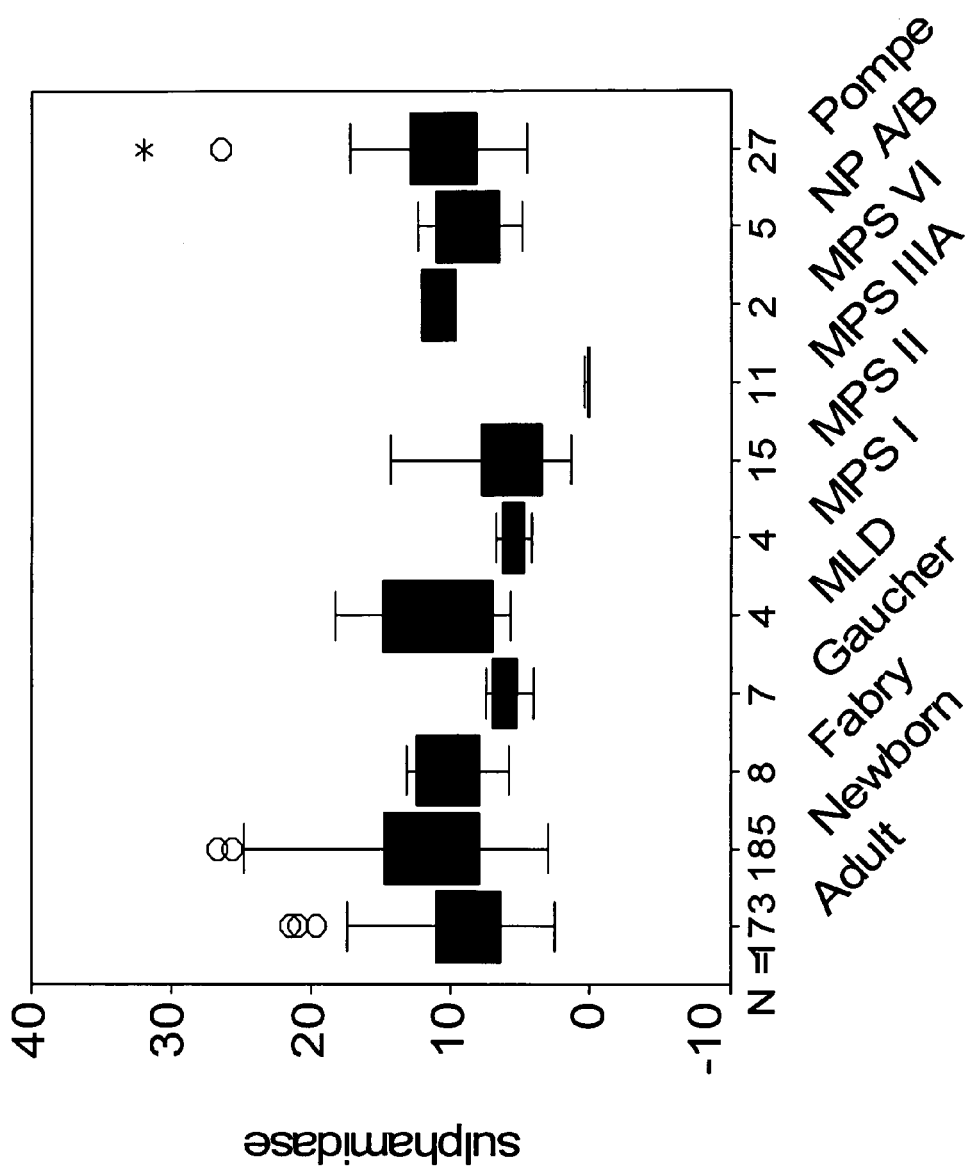
Figure 31:
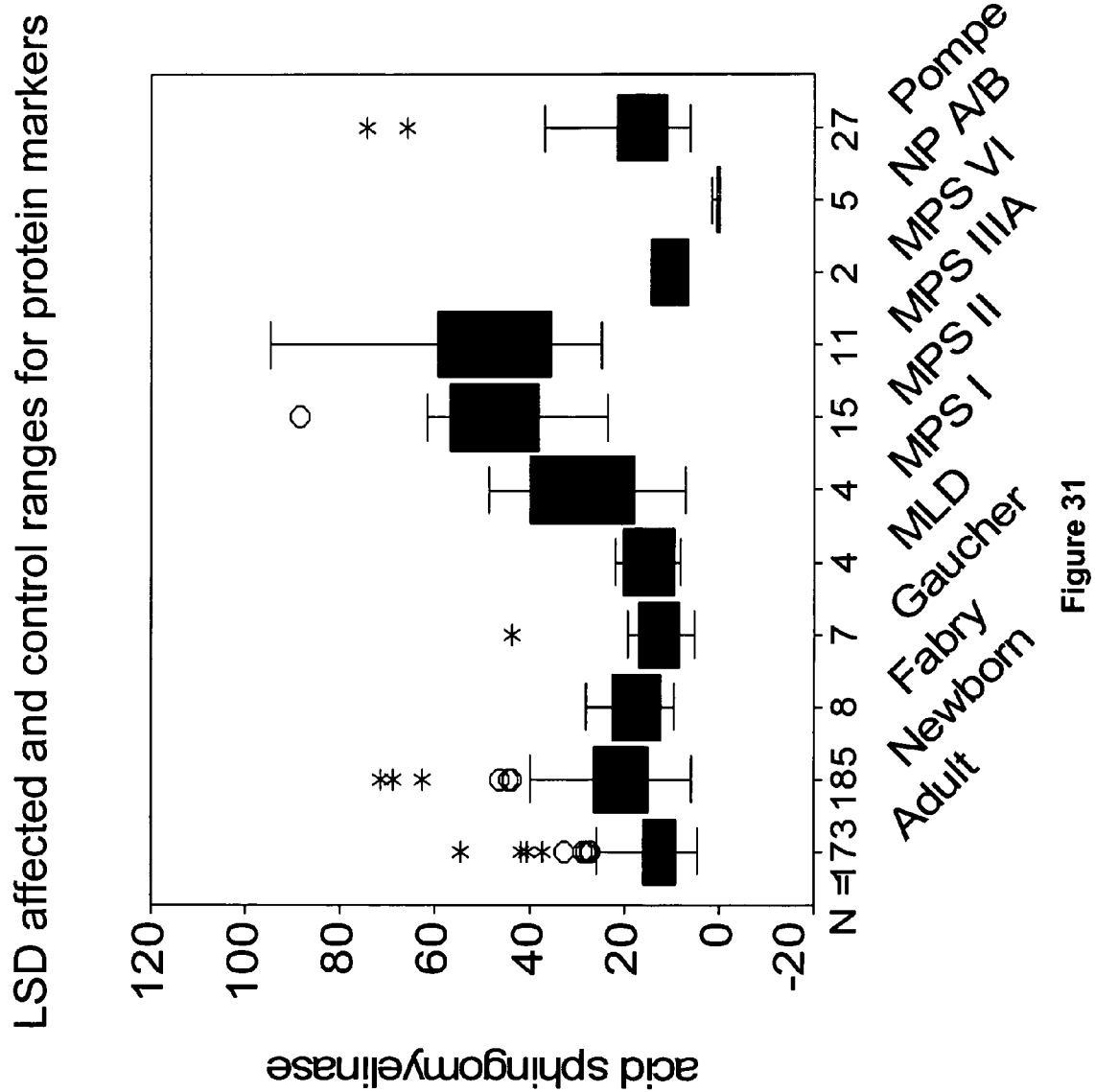
Figure 32:
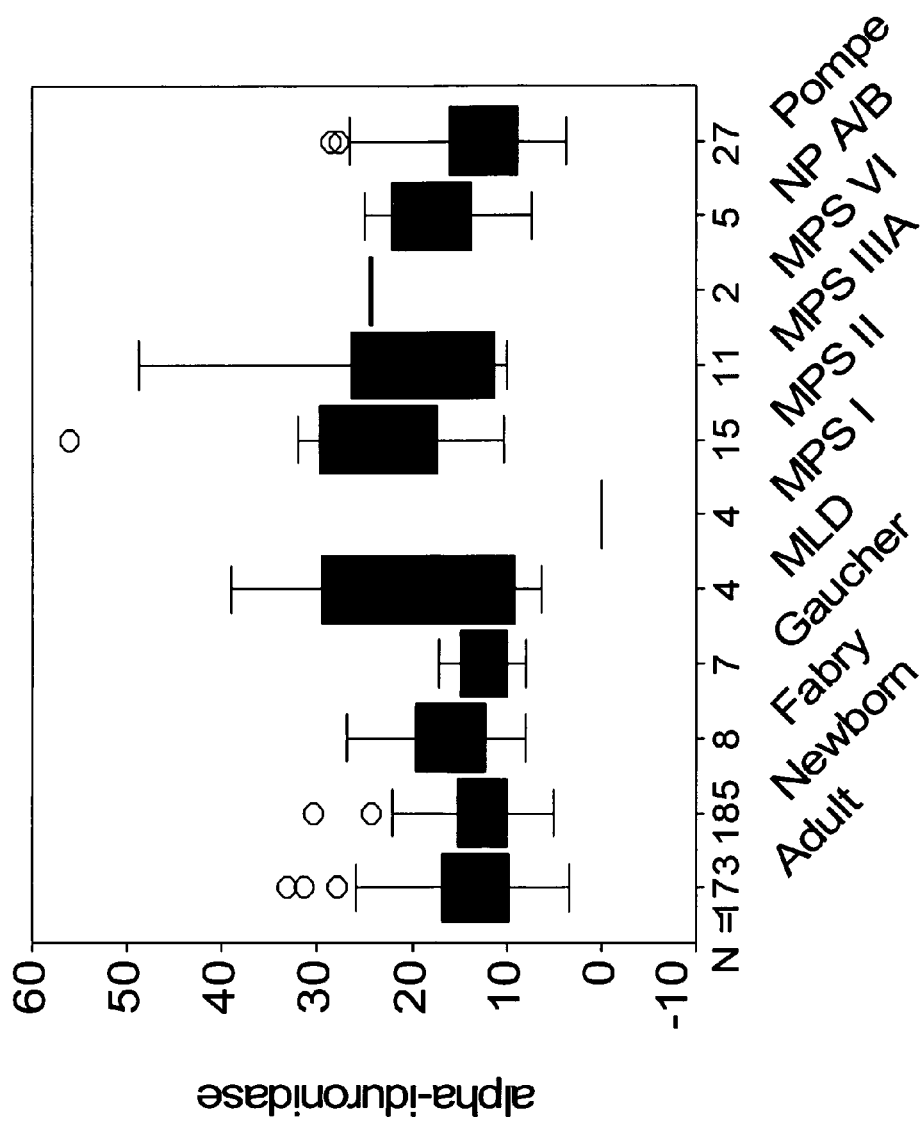
Figure 33:
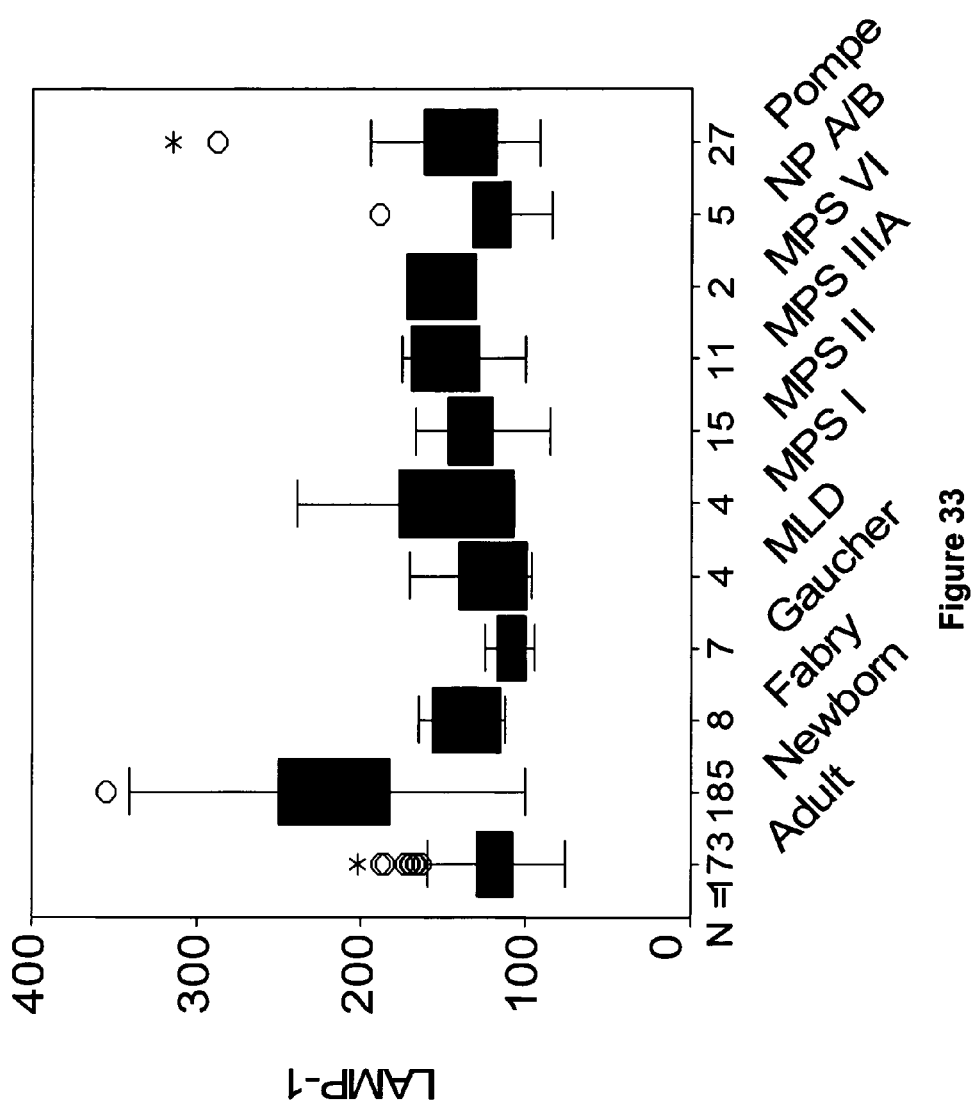
Figure 34:
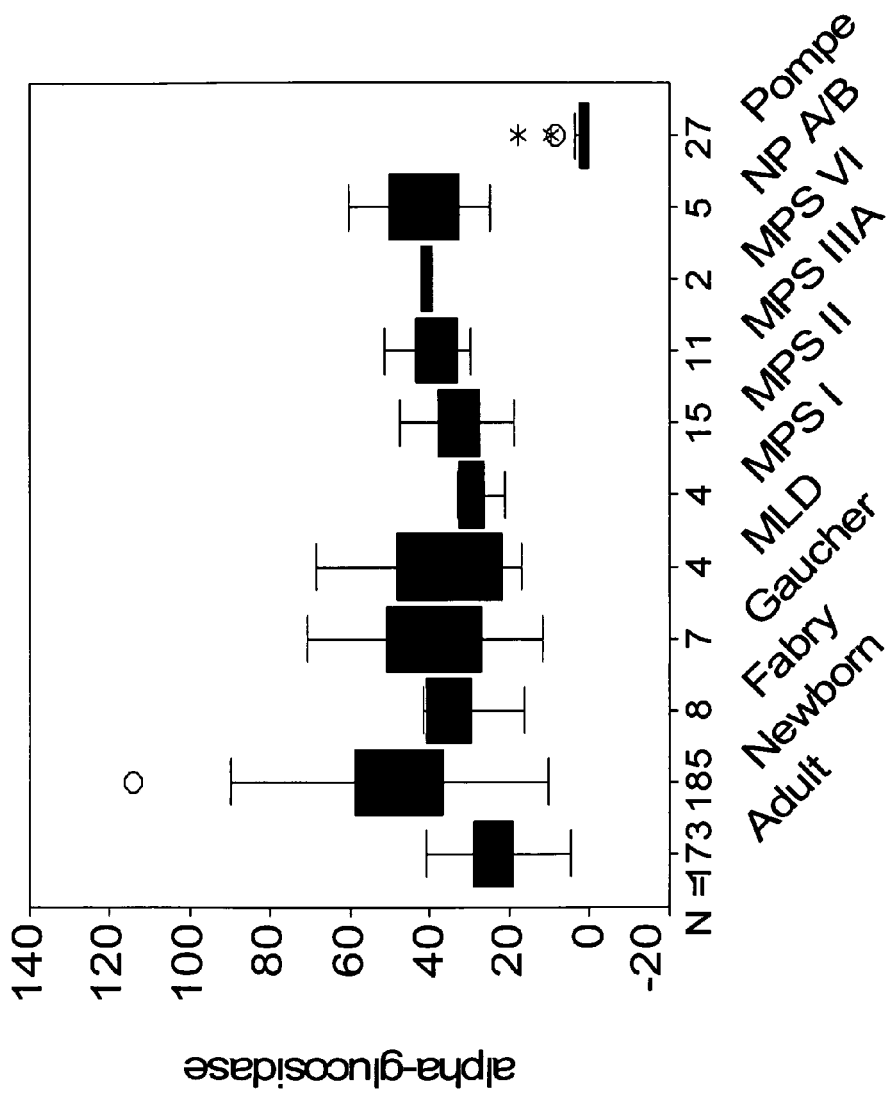
Figure 35:
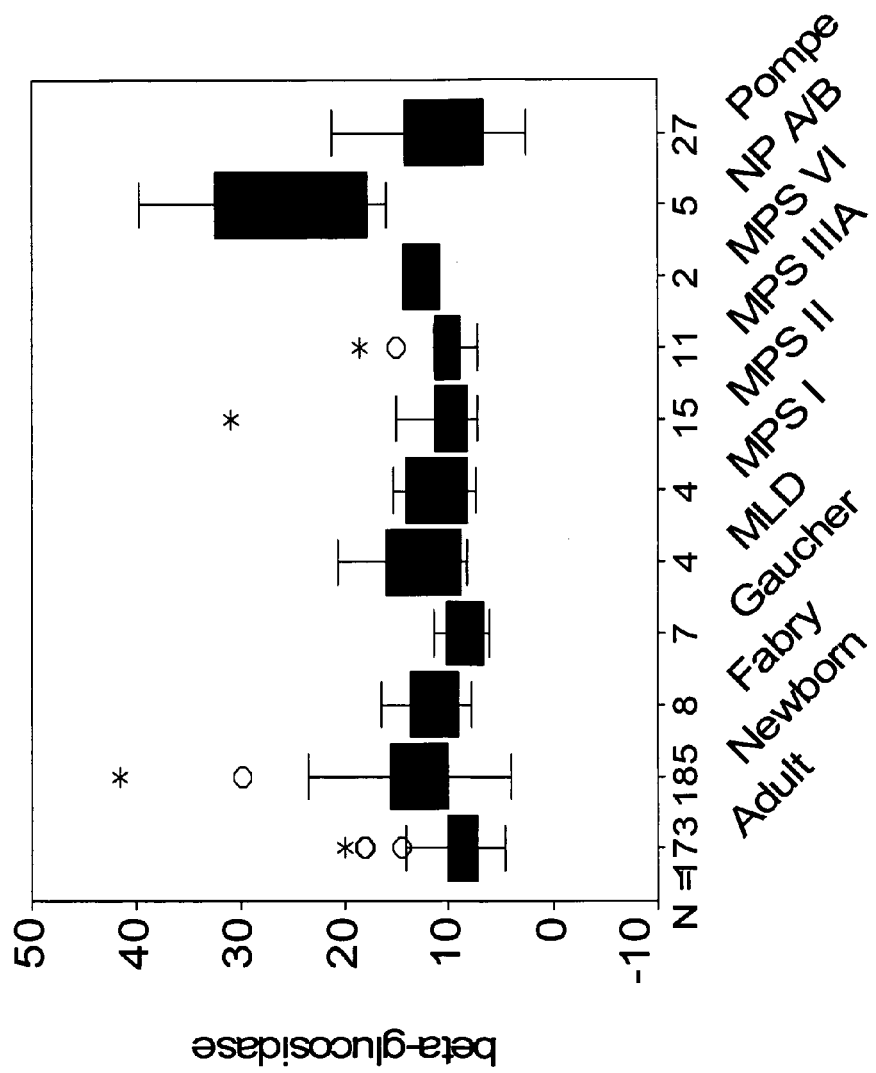
Figure 36:
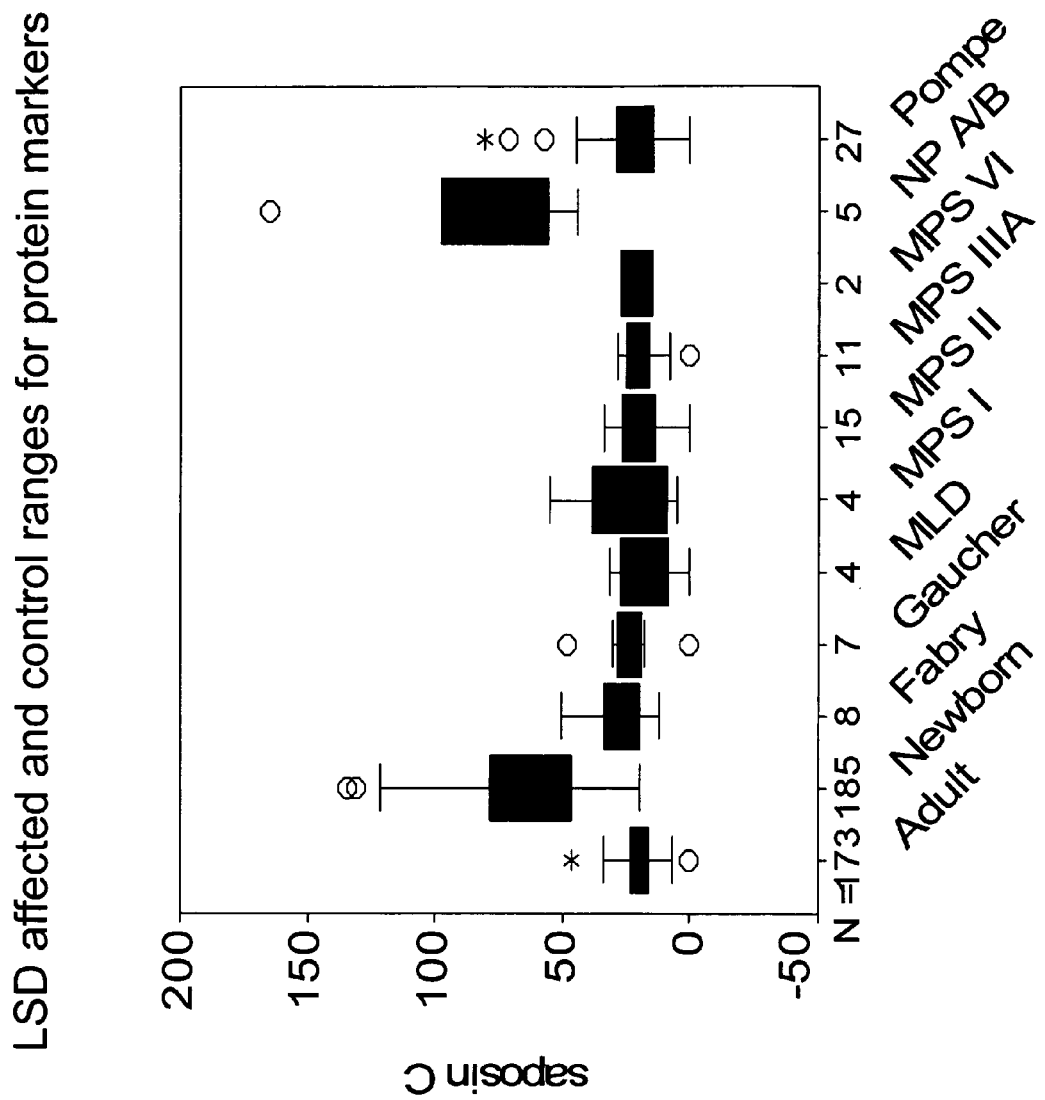
Figure 37:
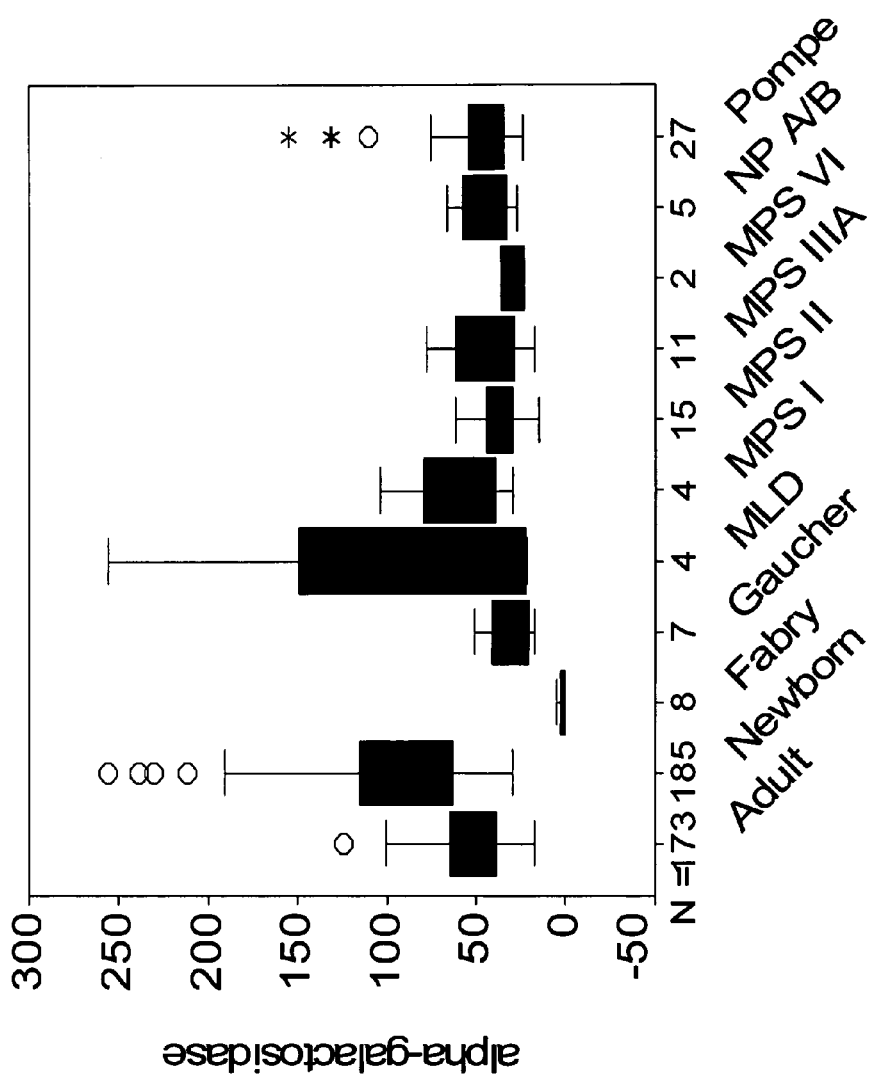
Figure 38:
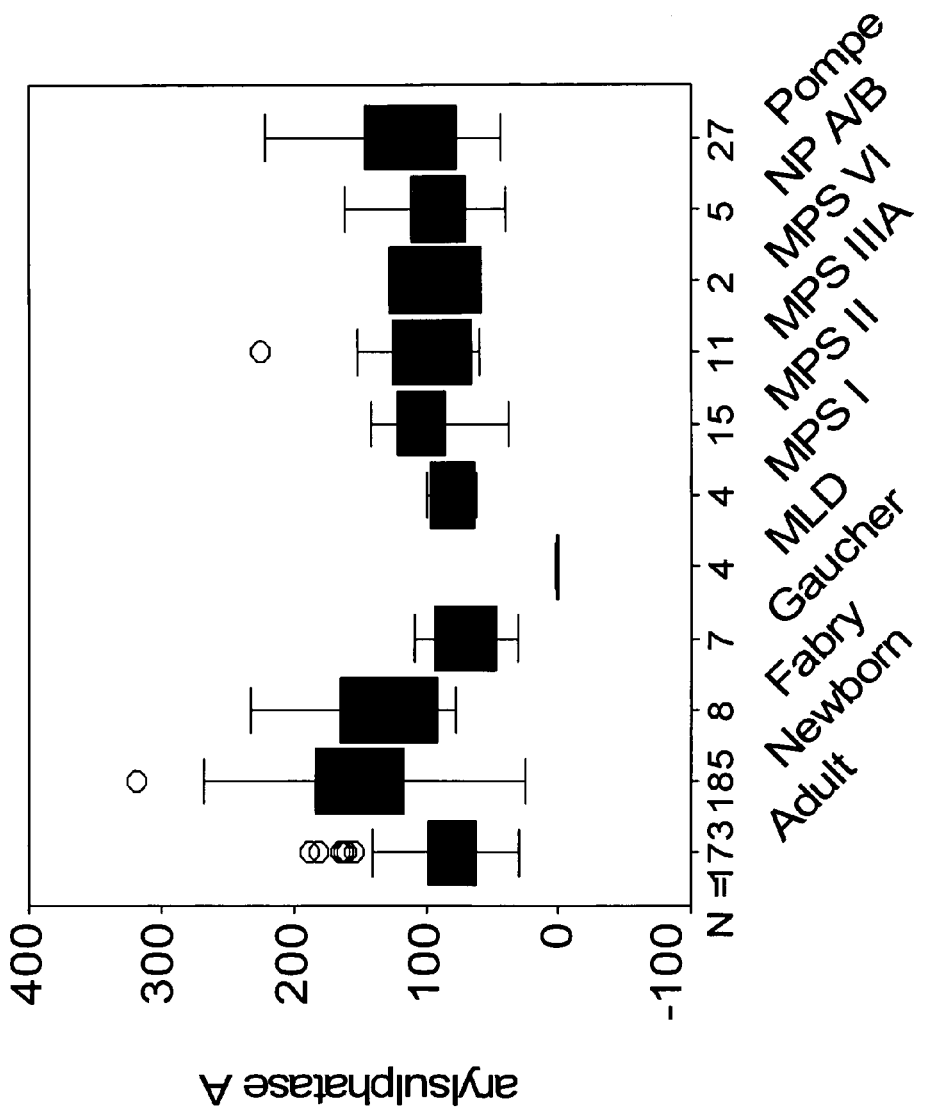
Figure 39:
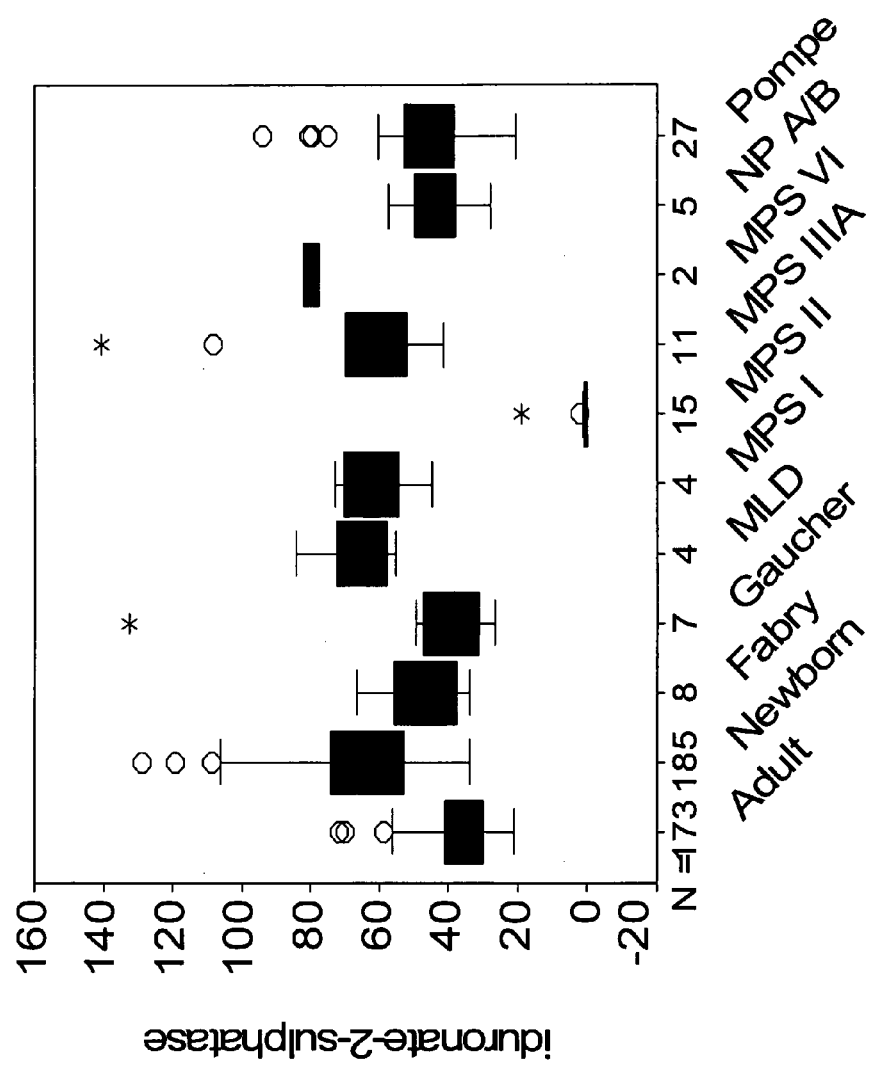
Figure 40:
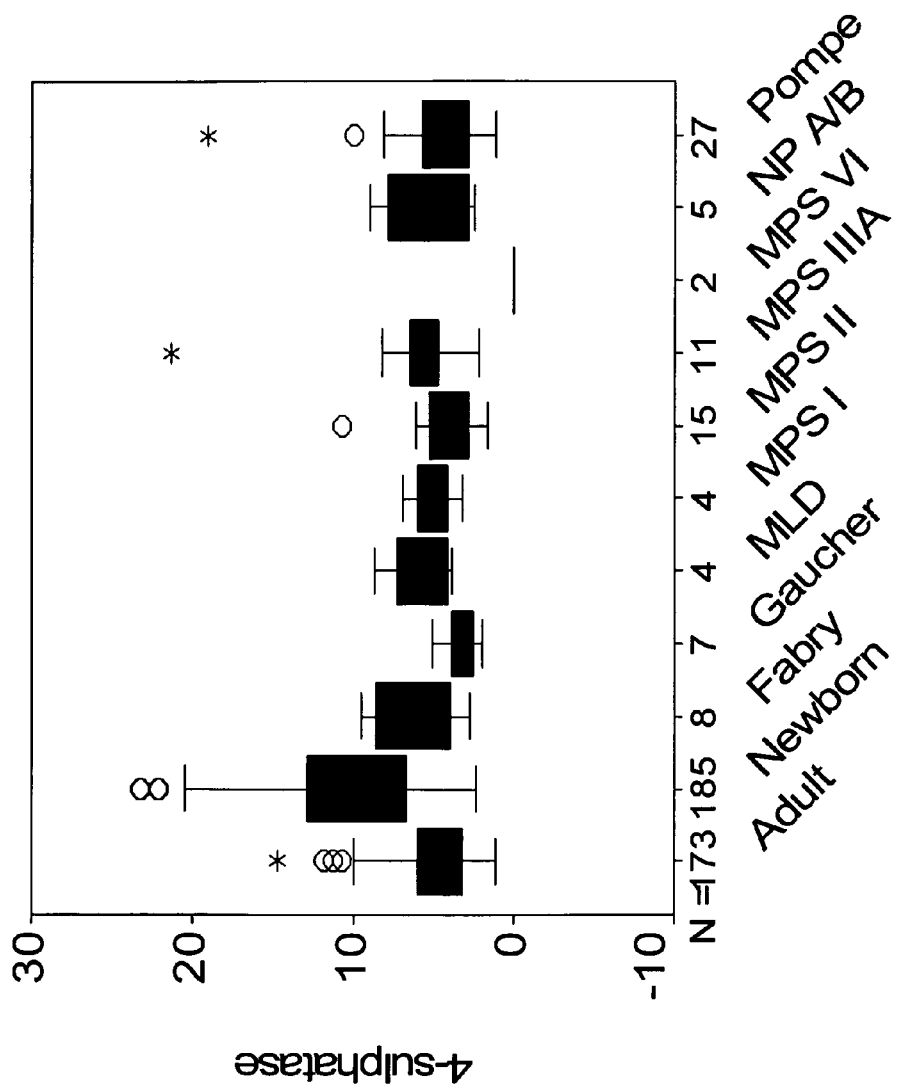
Figure 41:
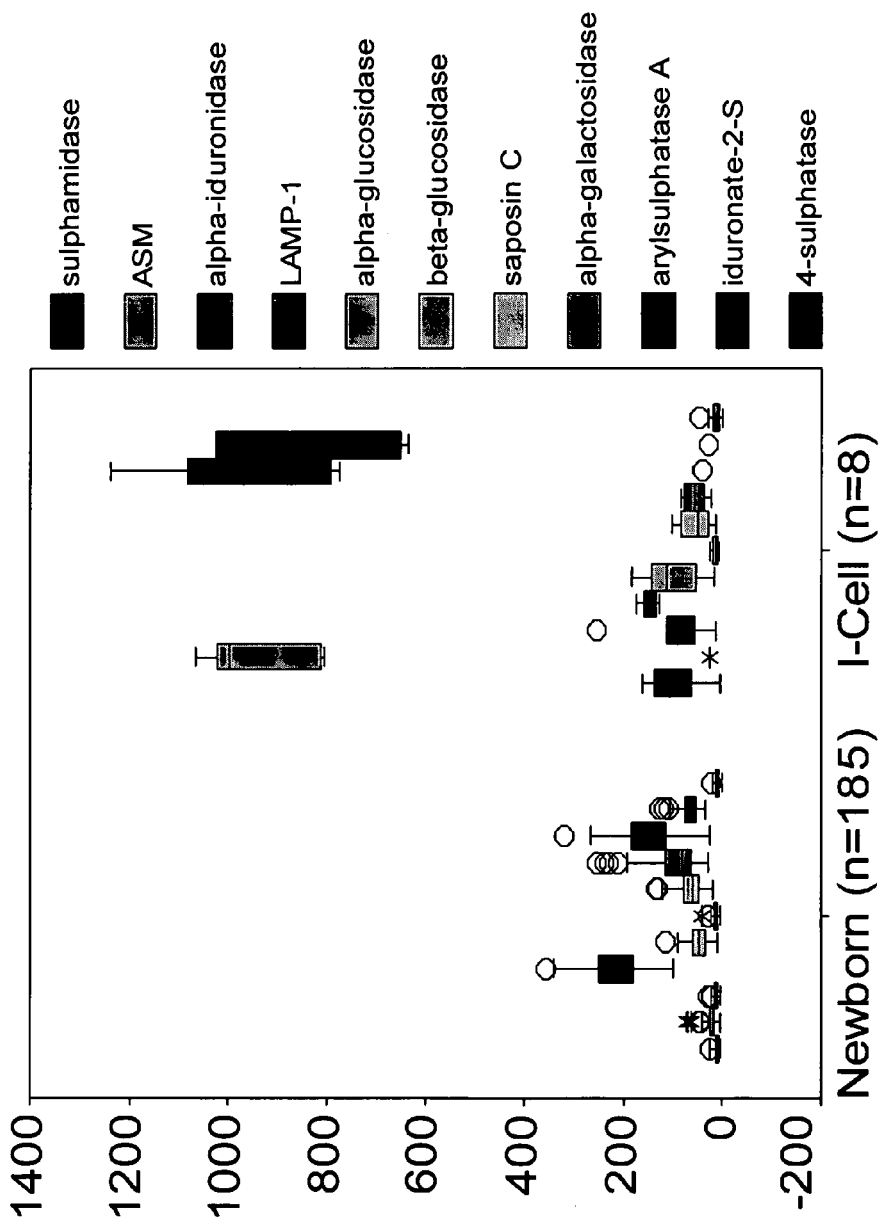
Figure 42:
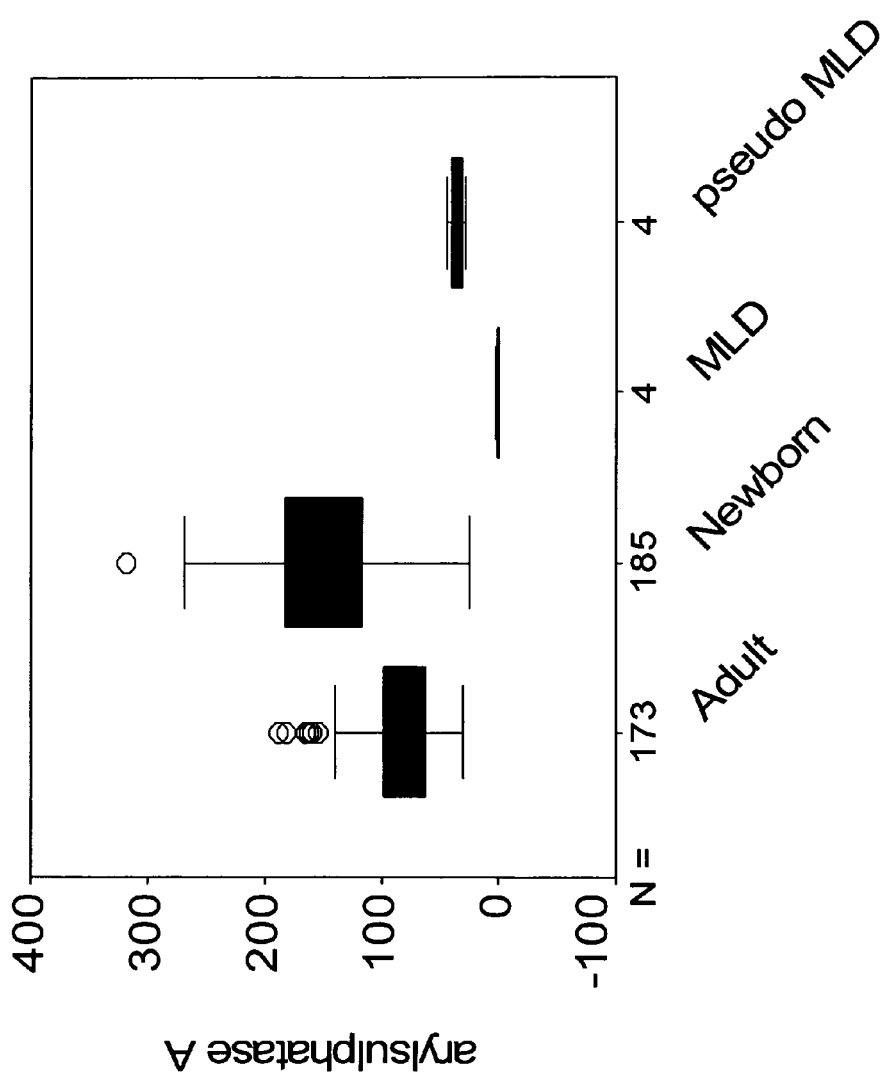
Figure 43:
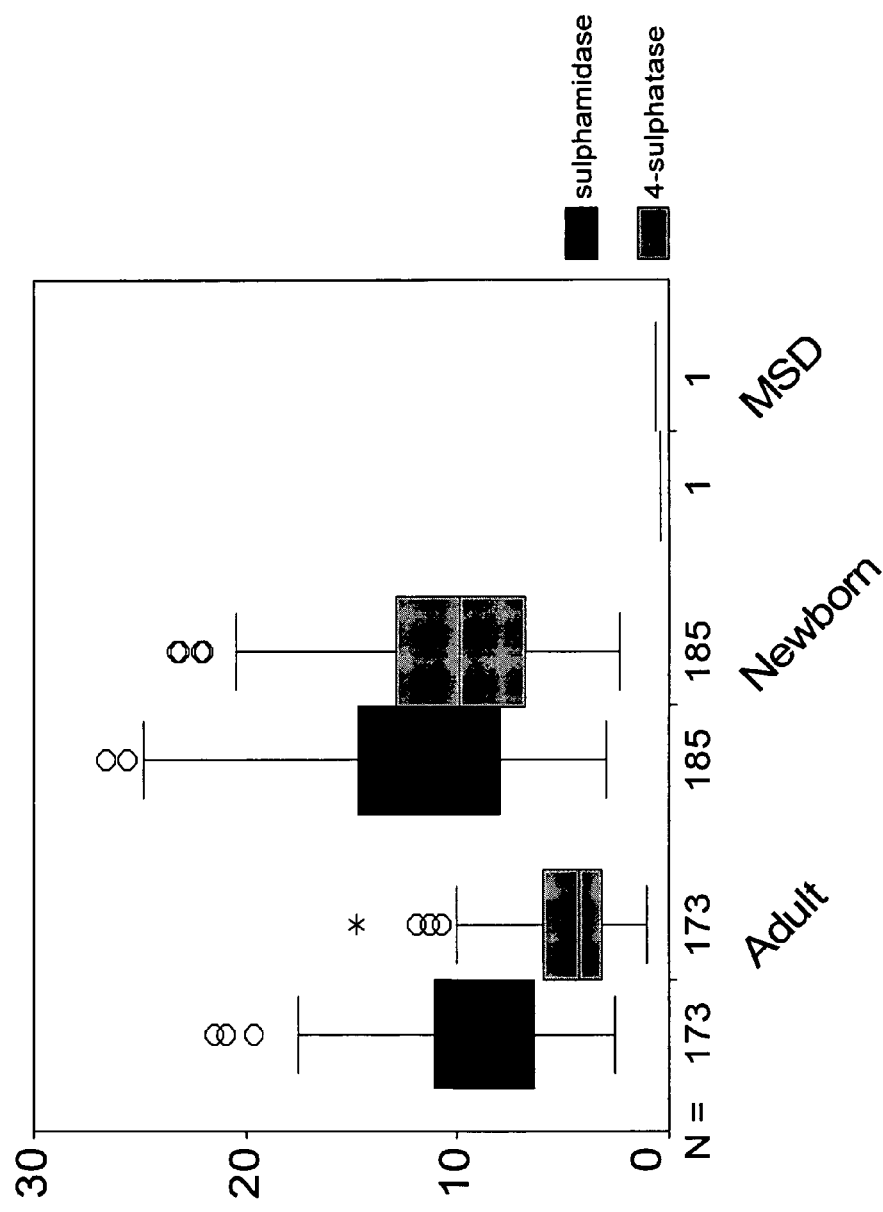
Figure 45:
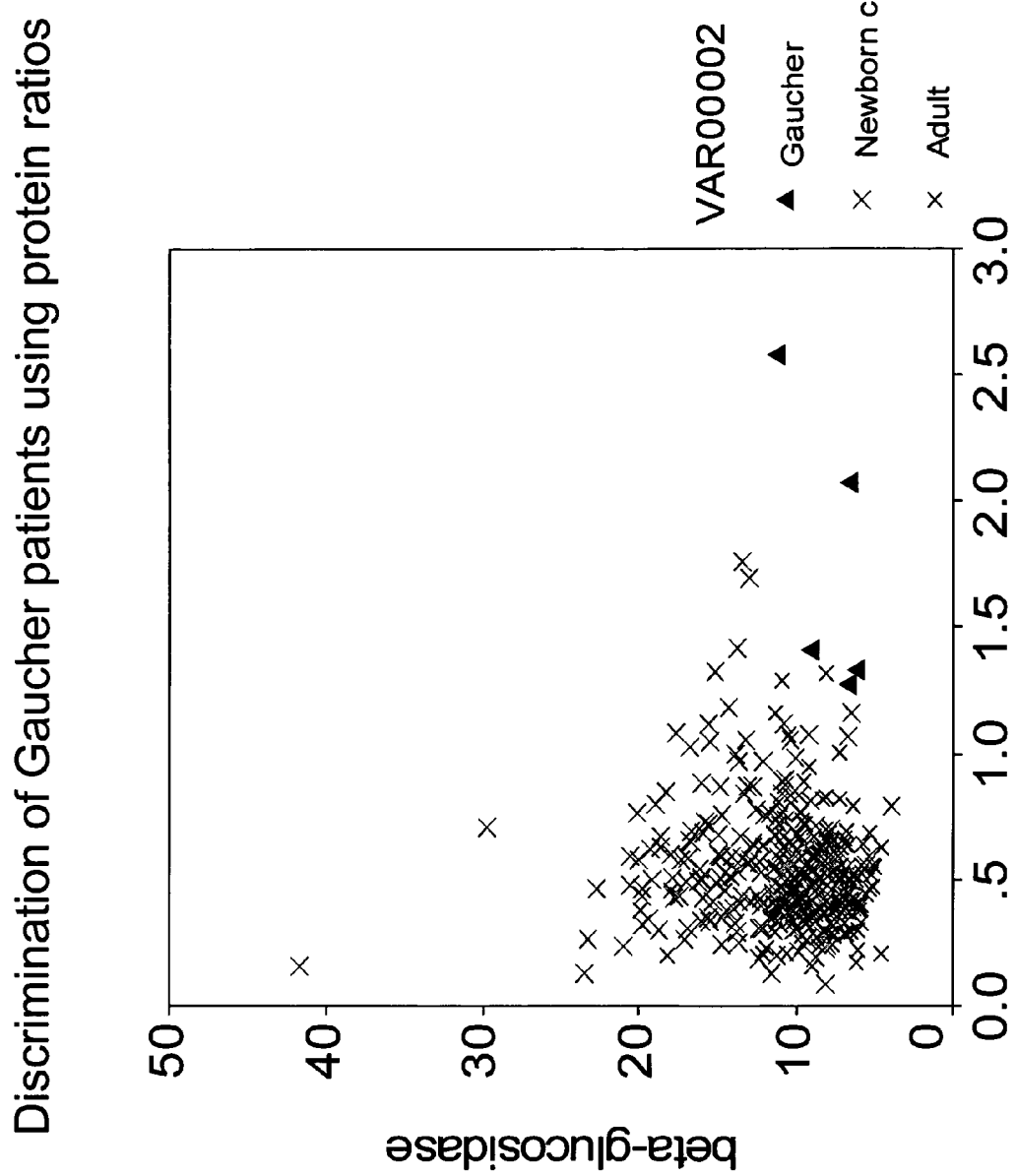
Figure 46:
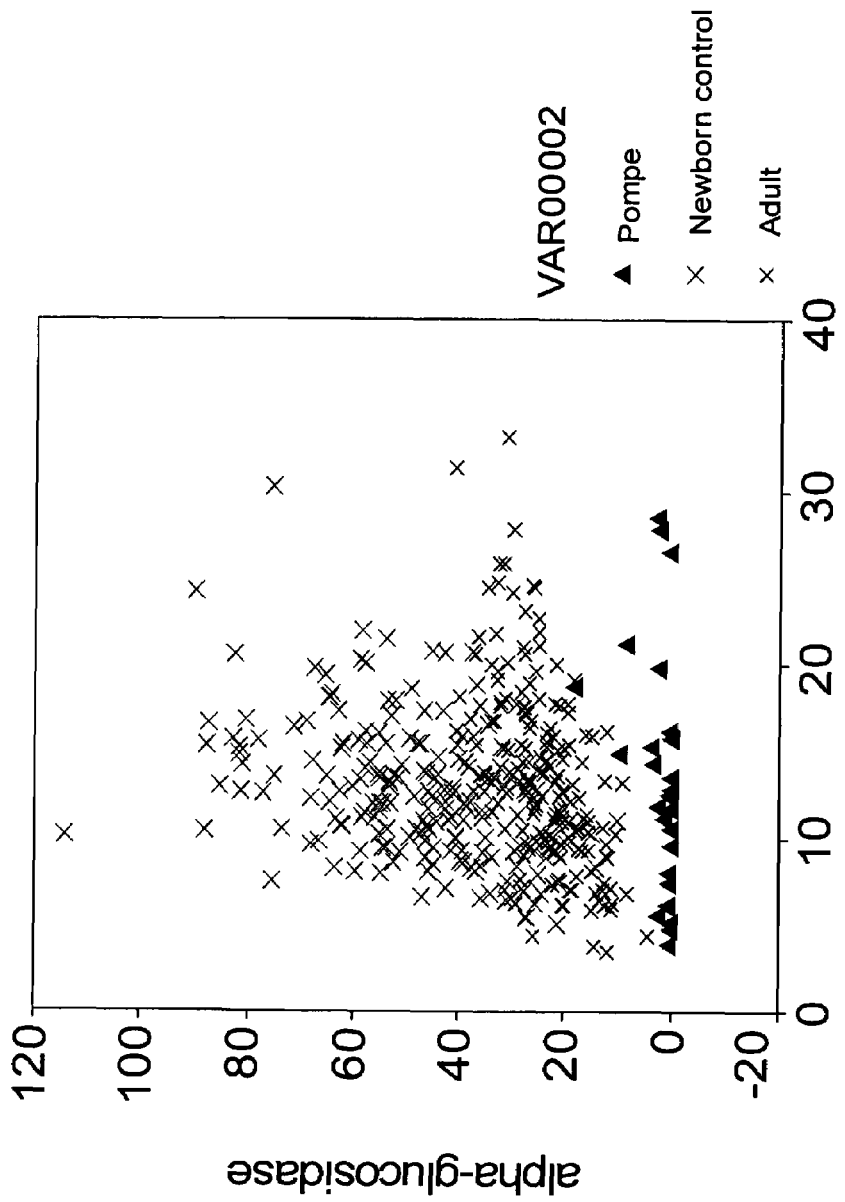
Figure 47:
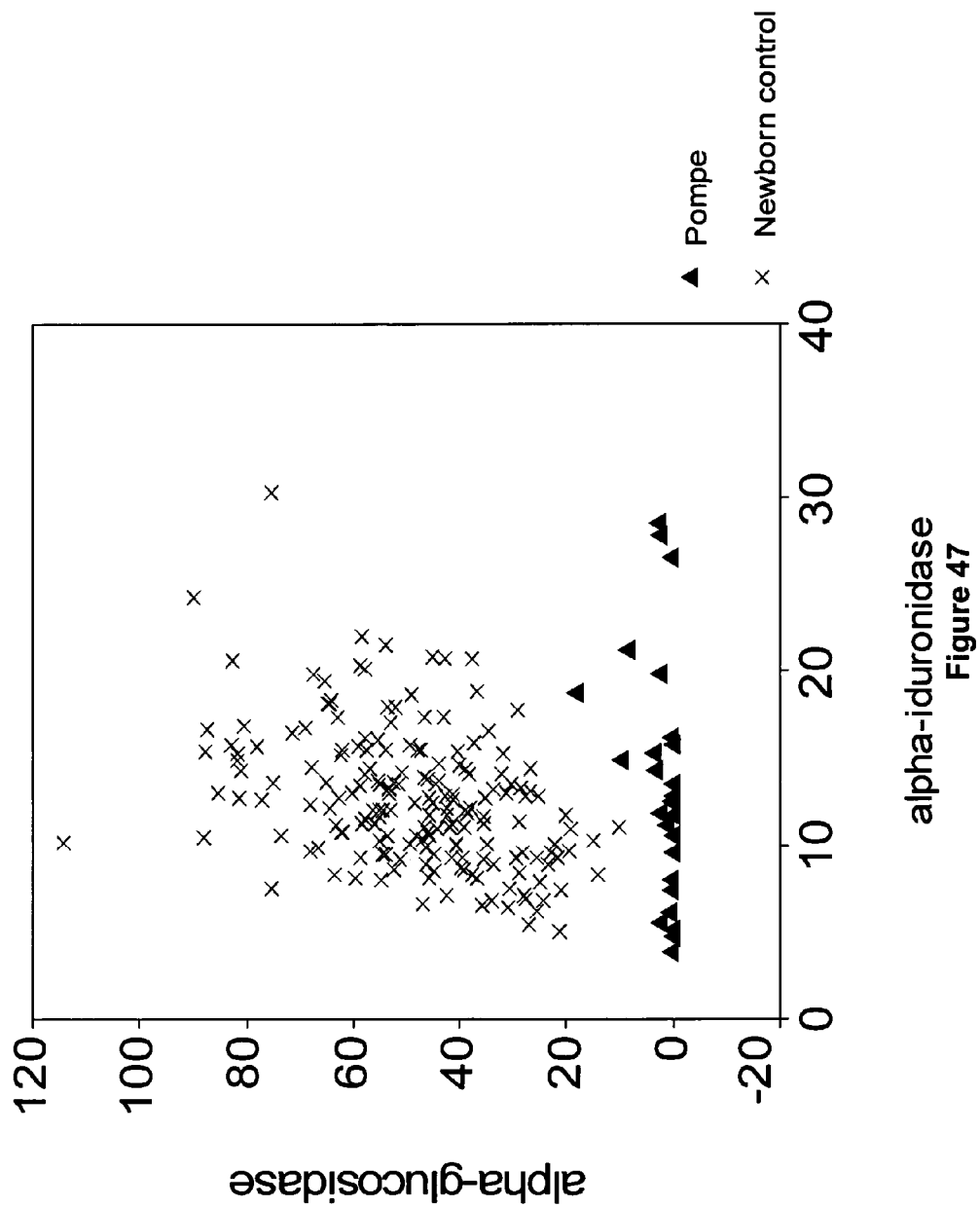
Figure 48:
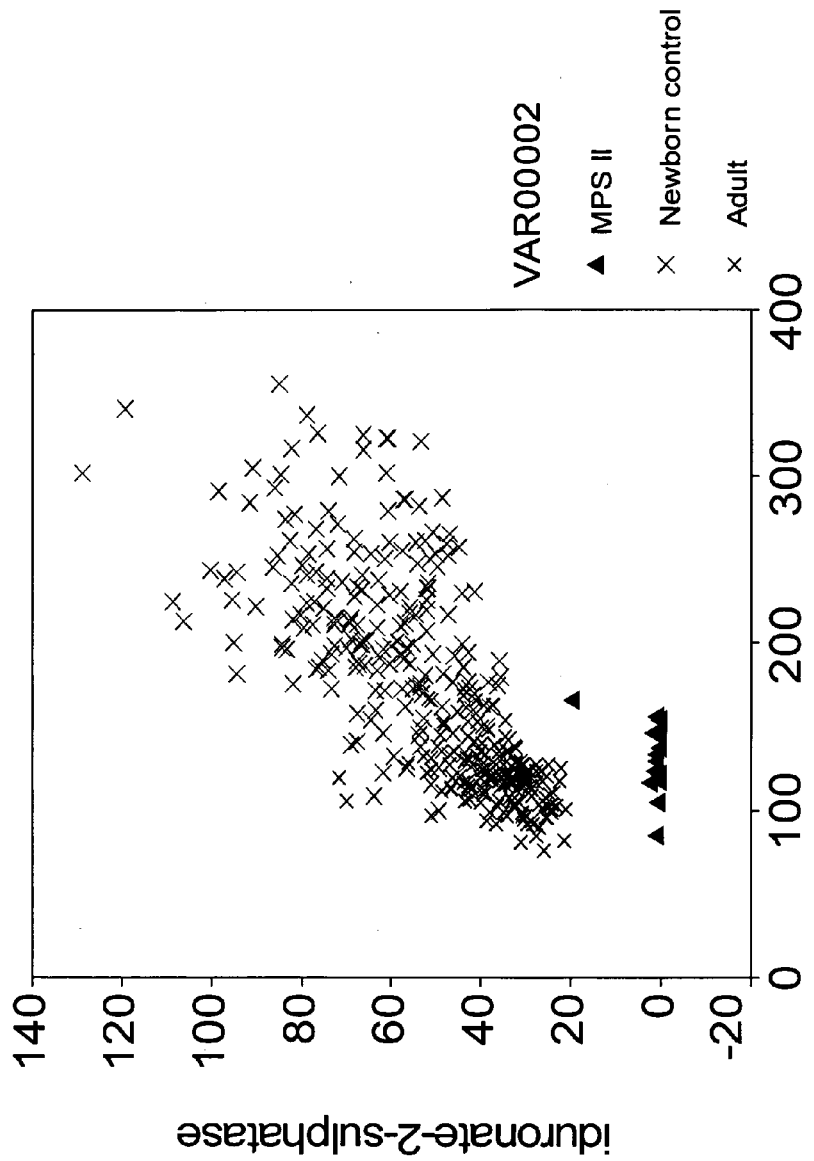
Figure 49:
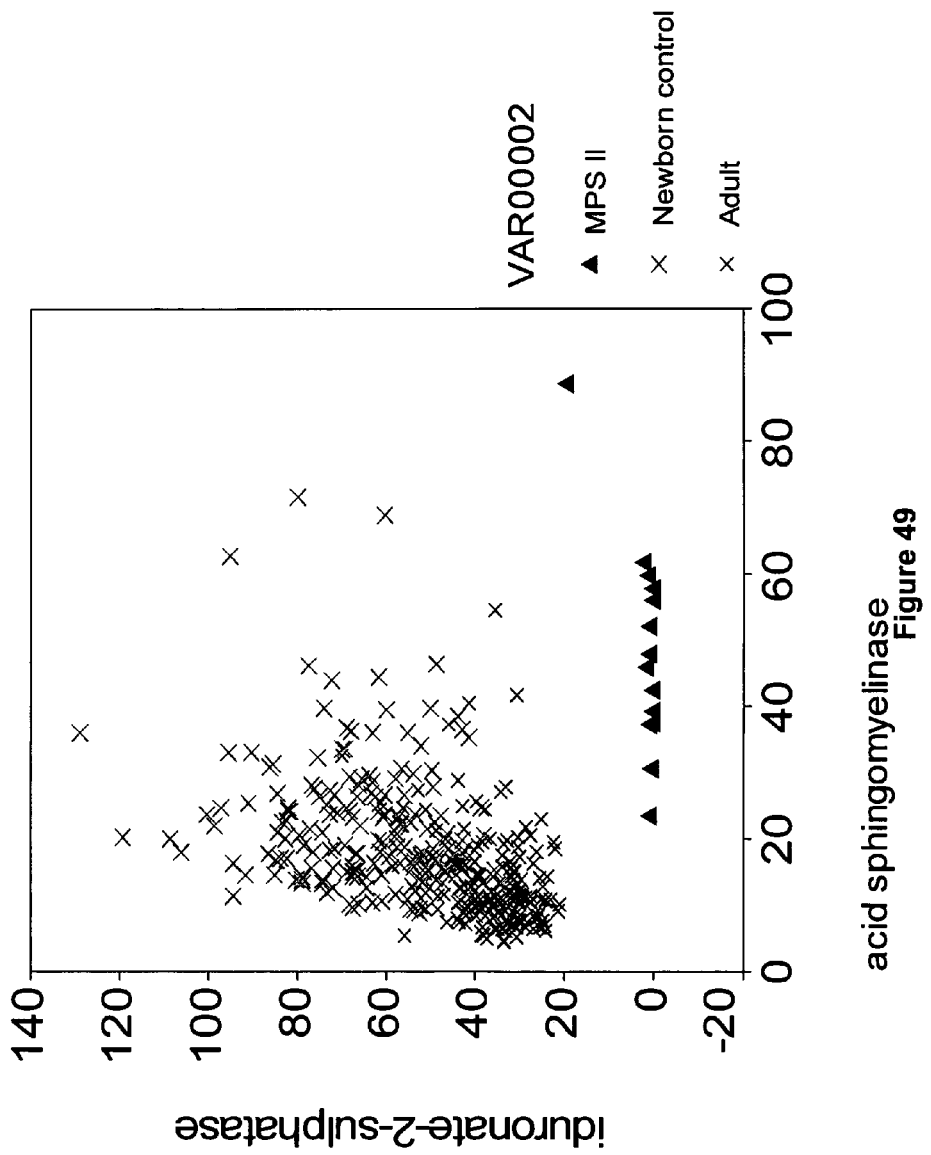
Figure 51:
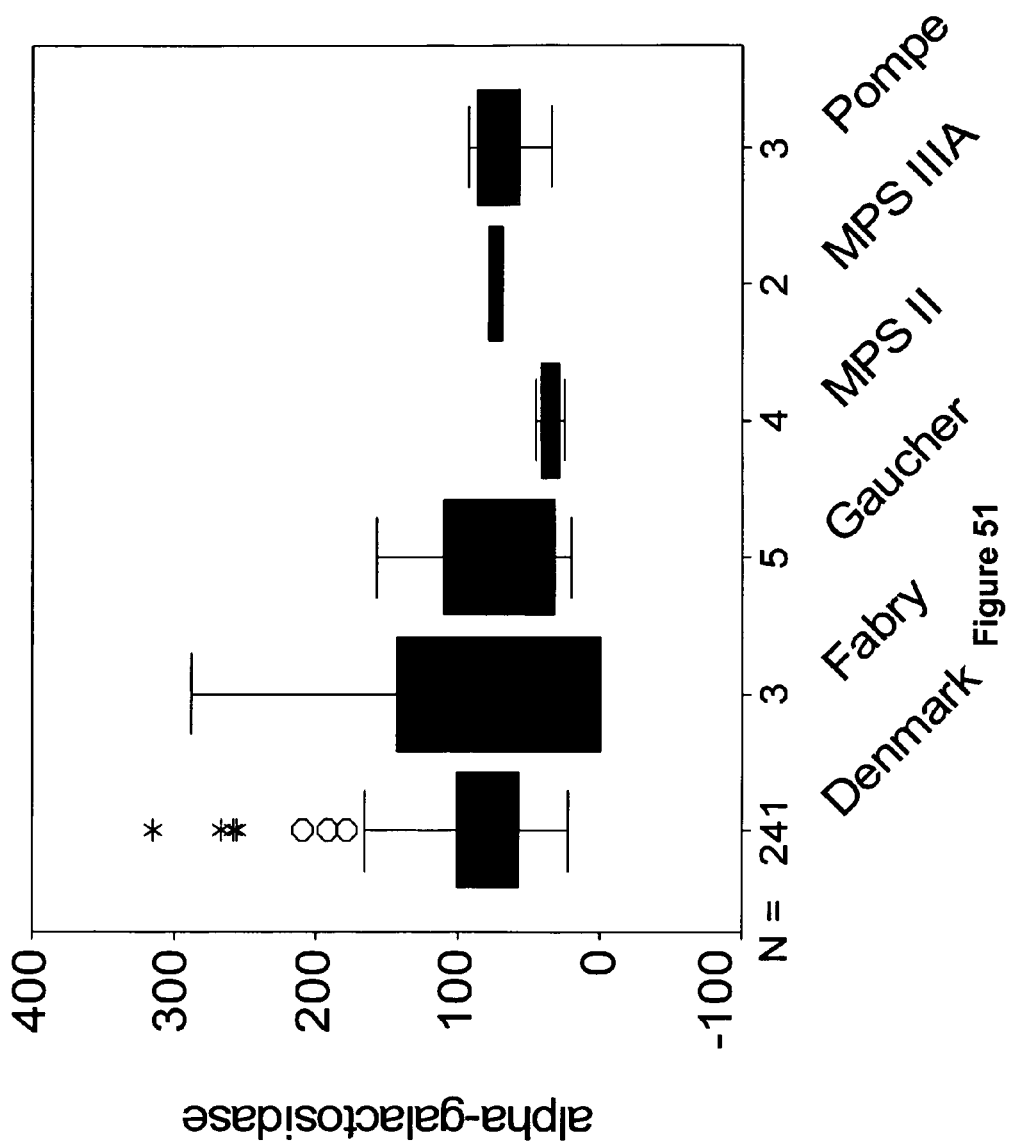
Figure 52:
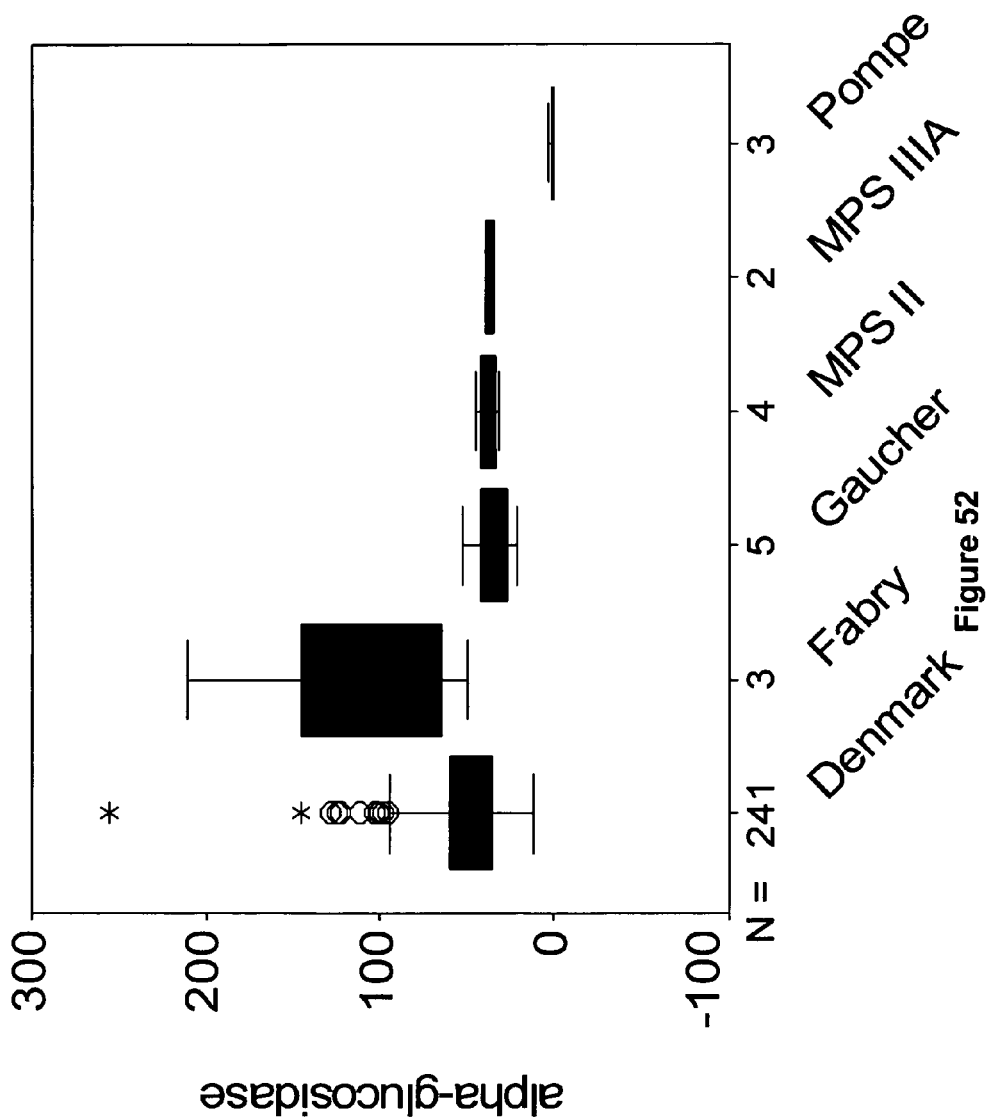
Figure 53:
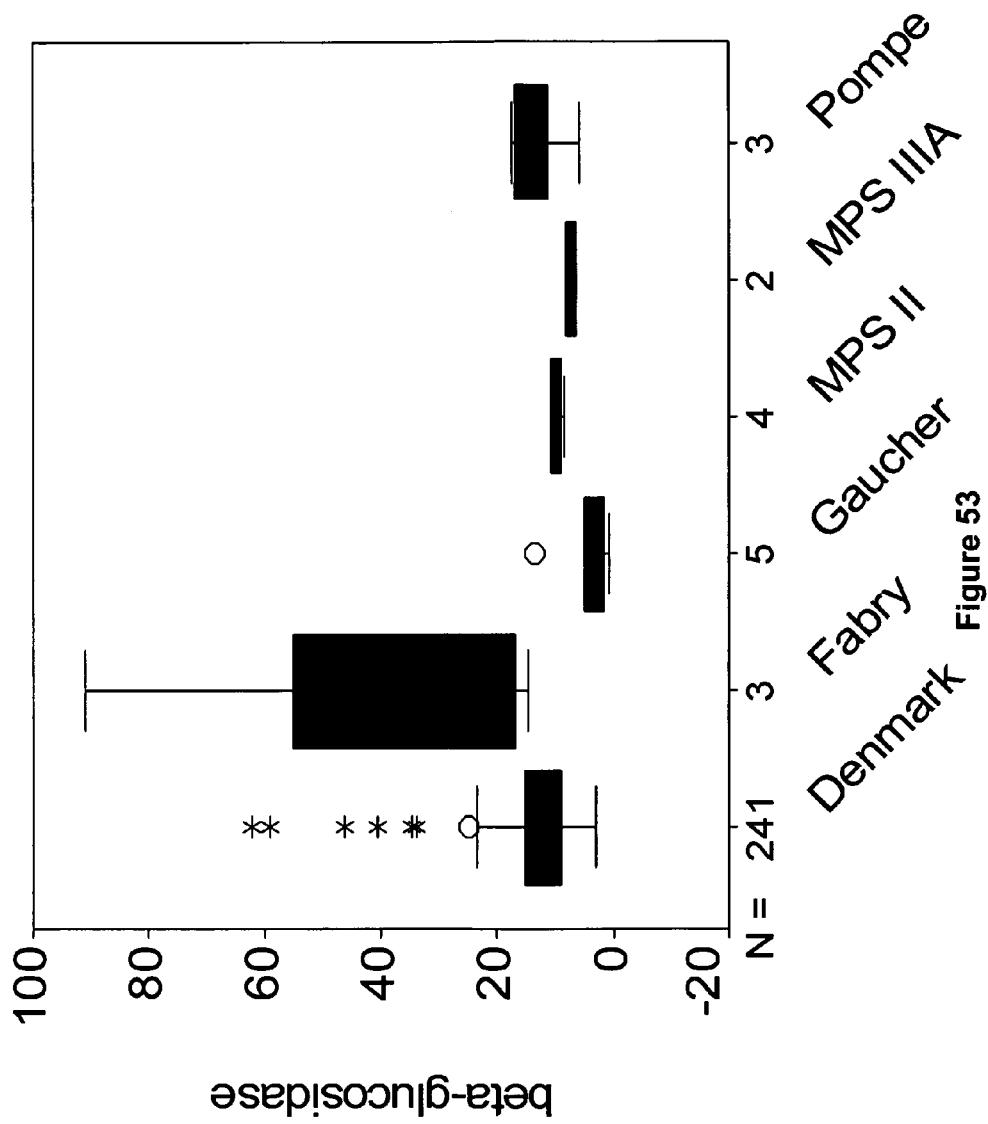
Figure 54:
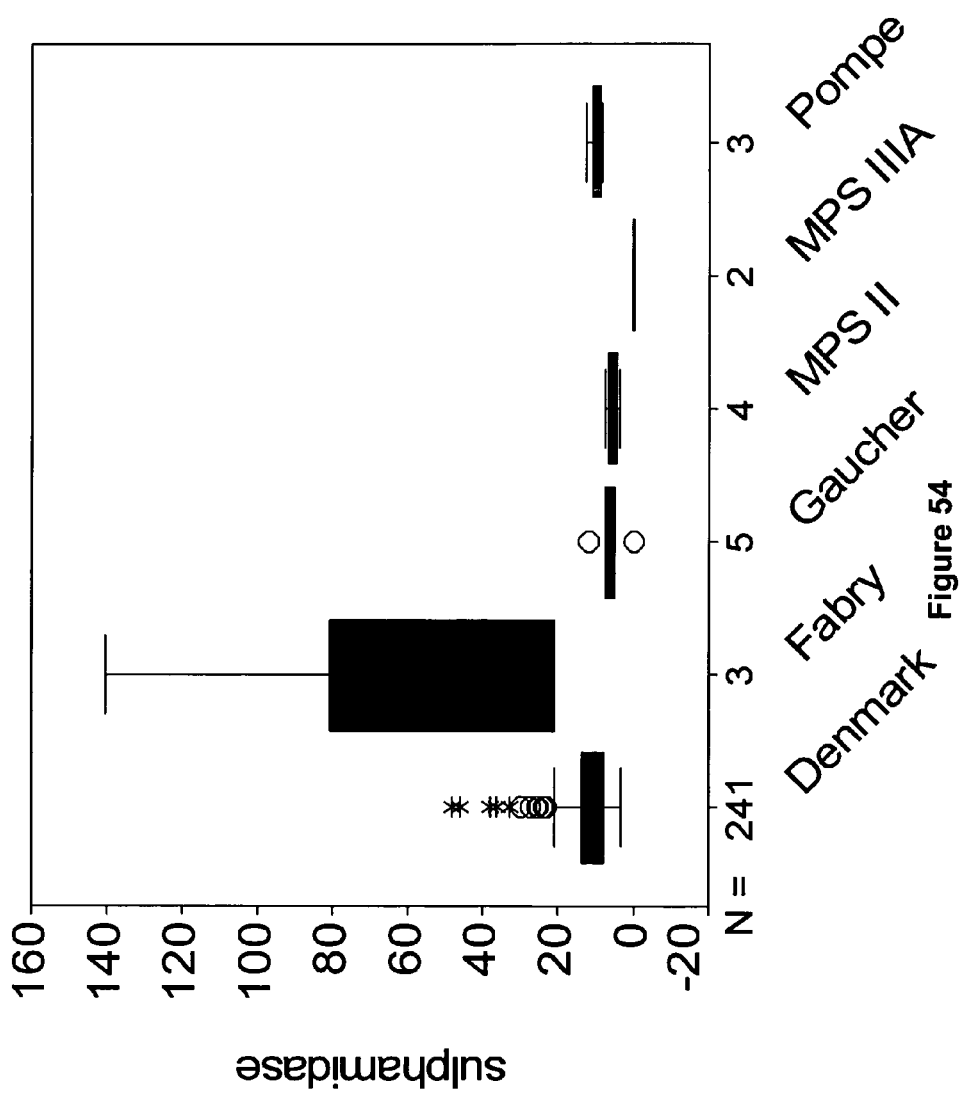
Figure 55:
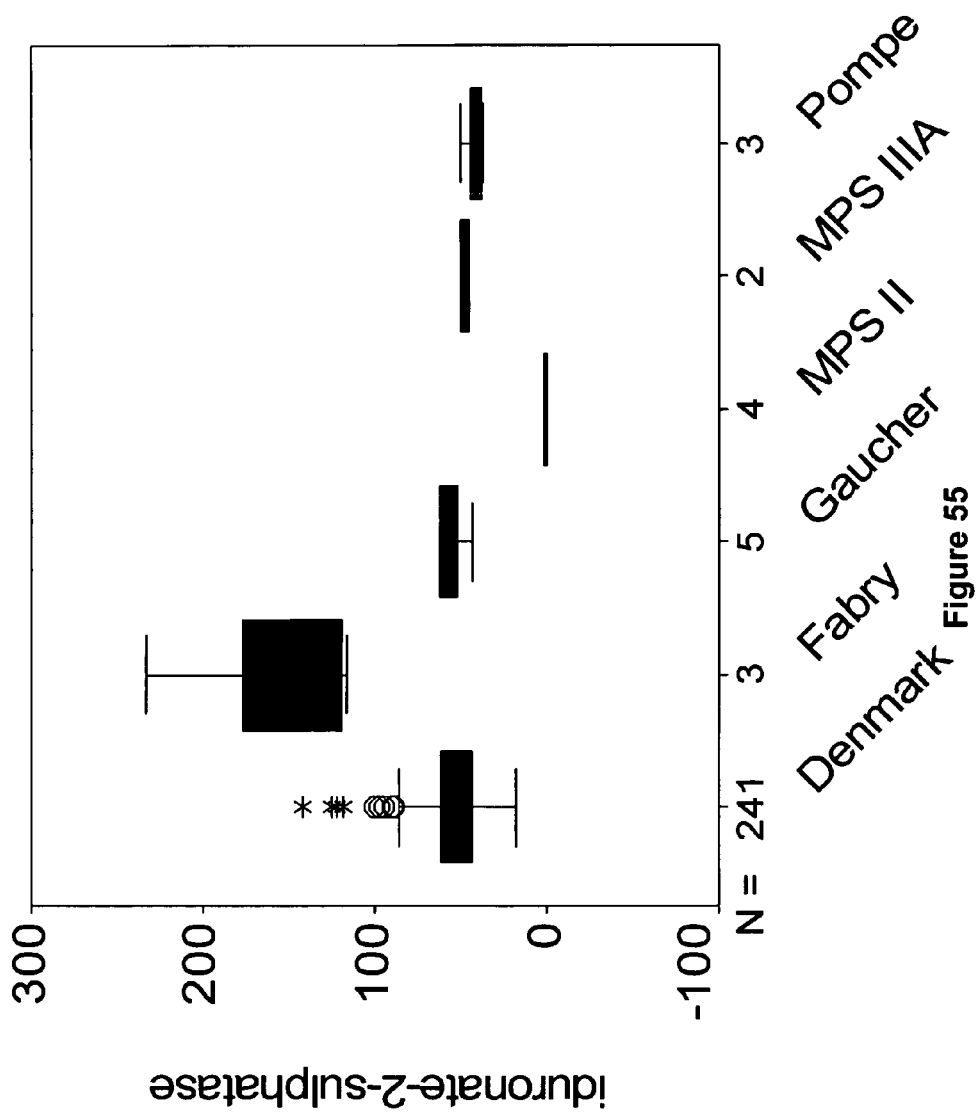
Figure 56:
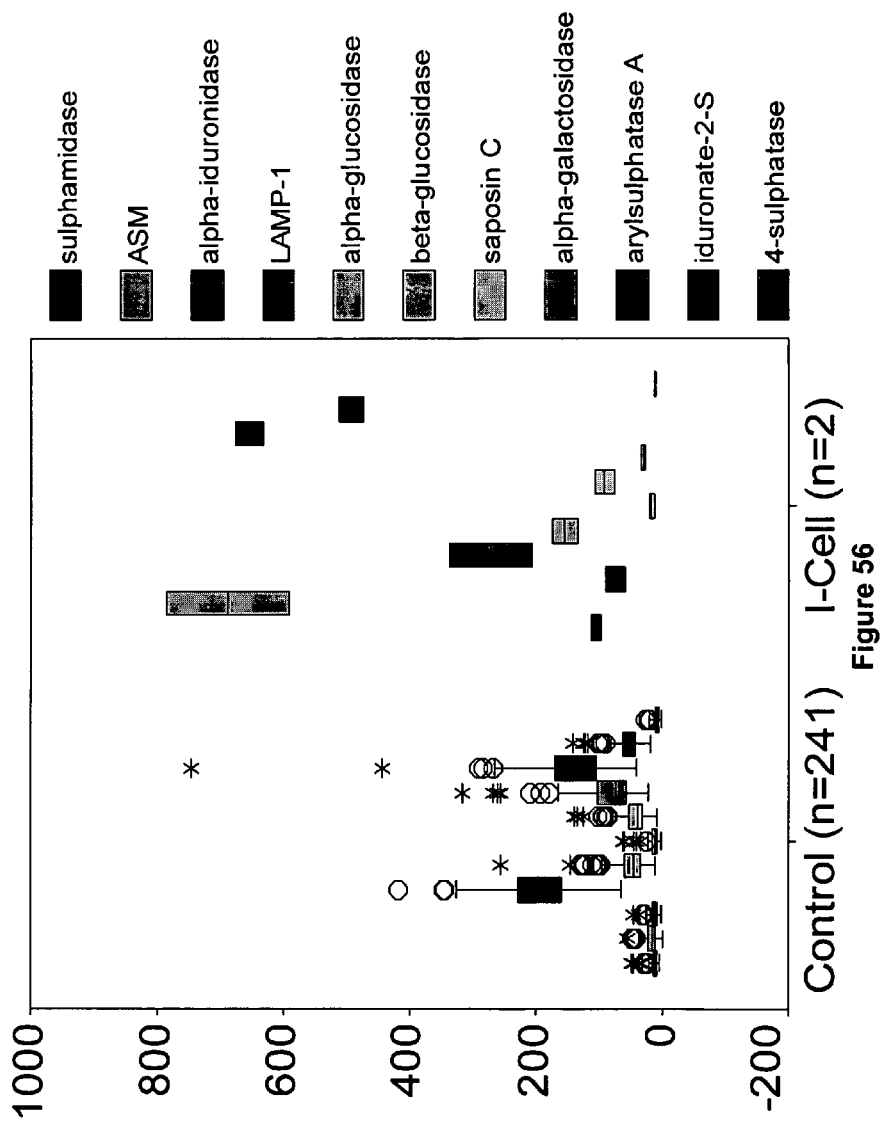
Figure 57:
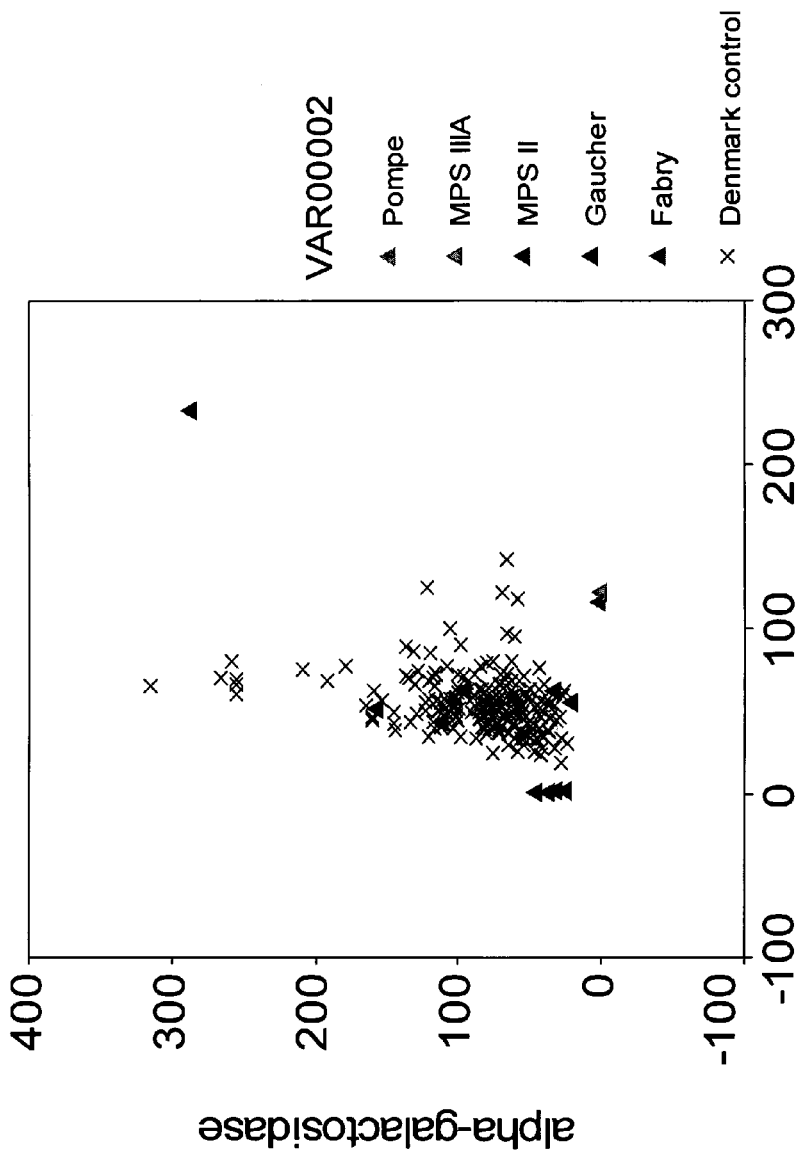
Figure 58:
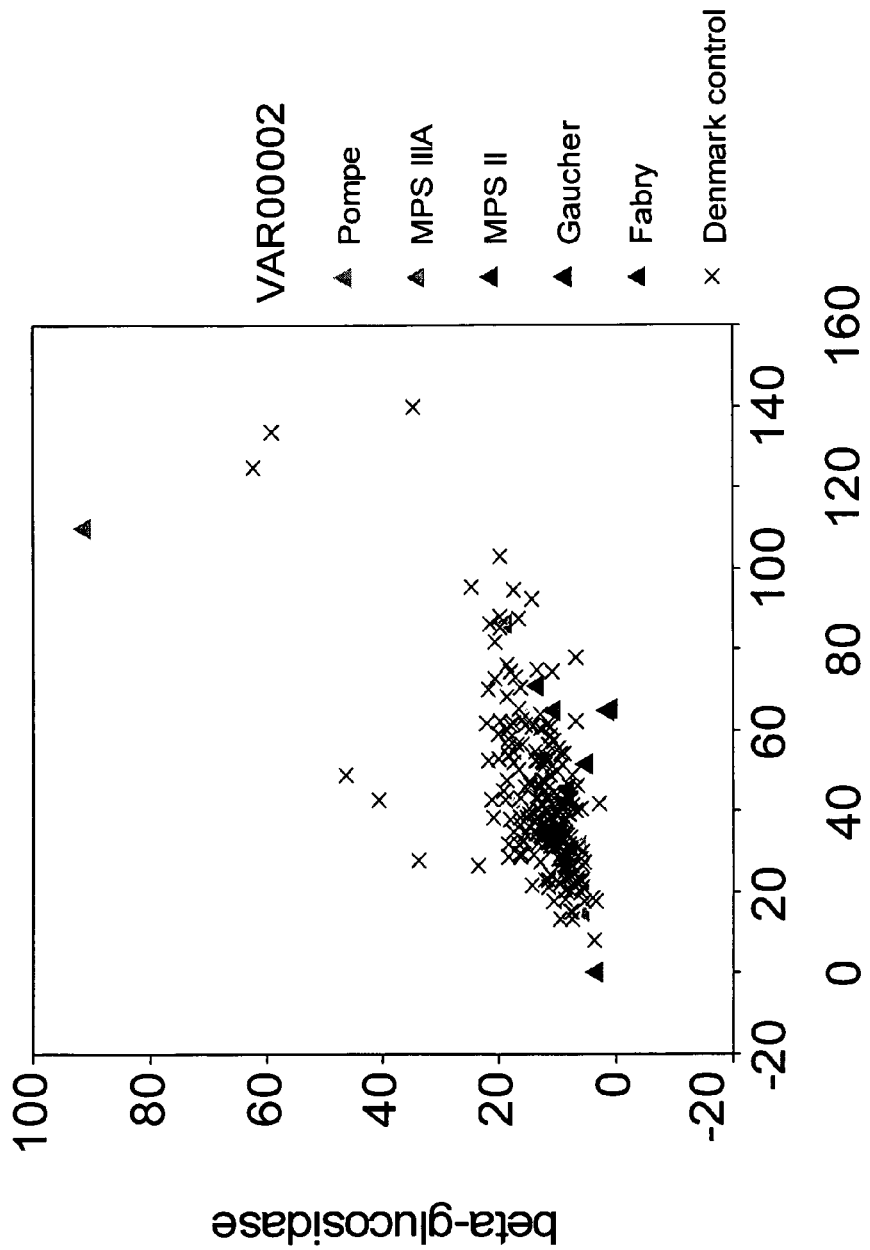
Figure 59:
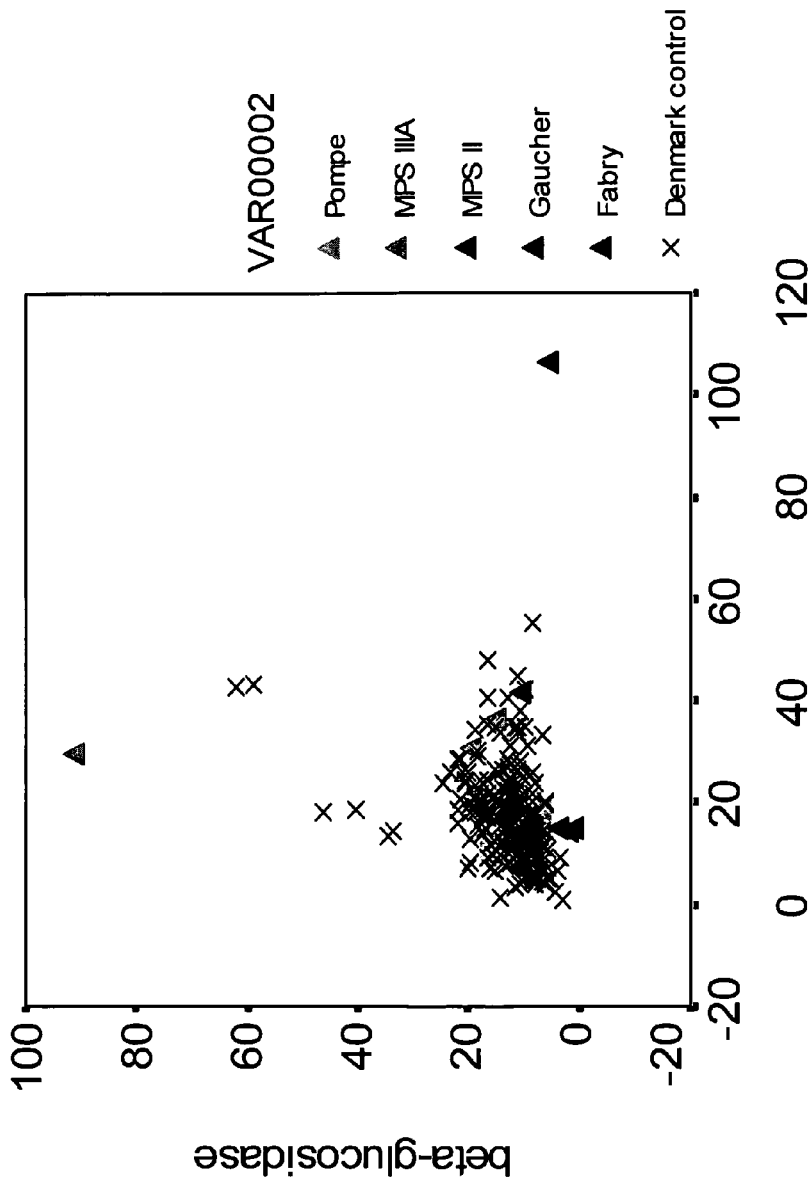
Figure 63:
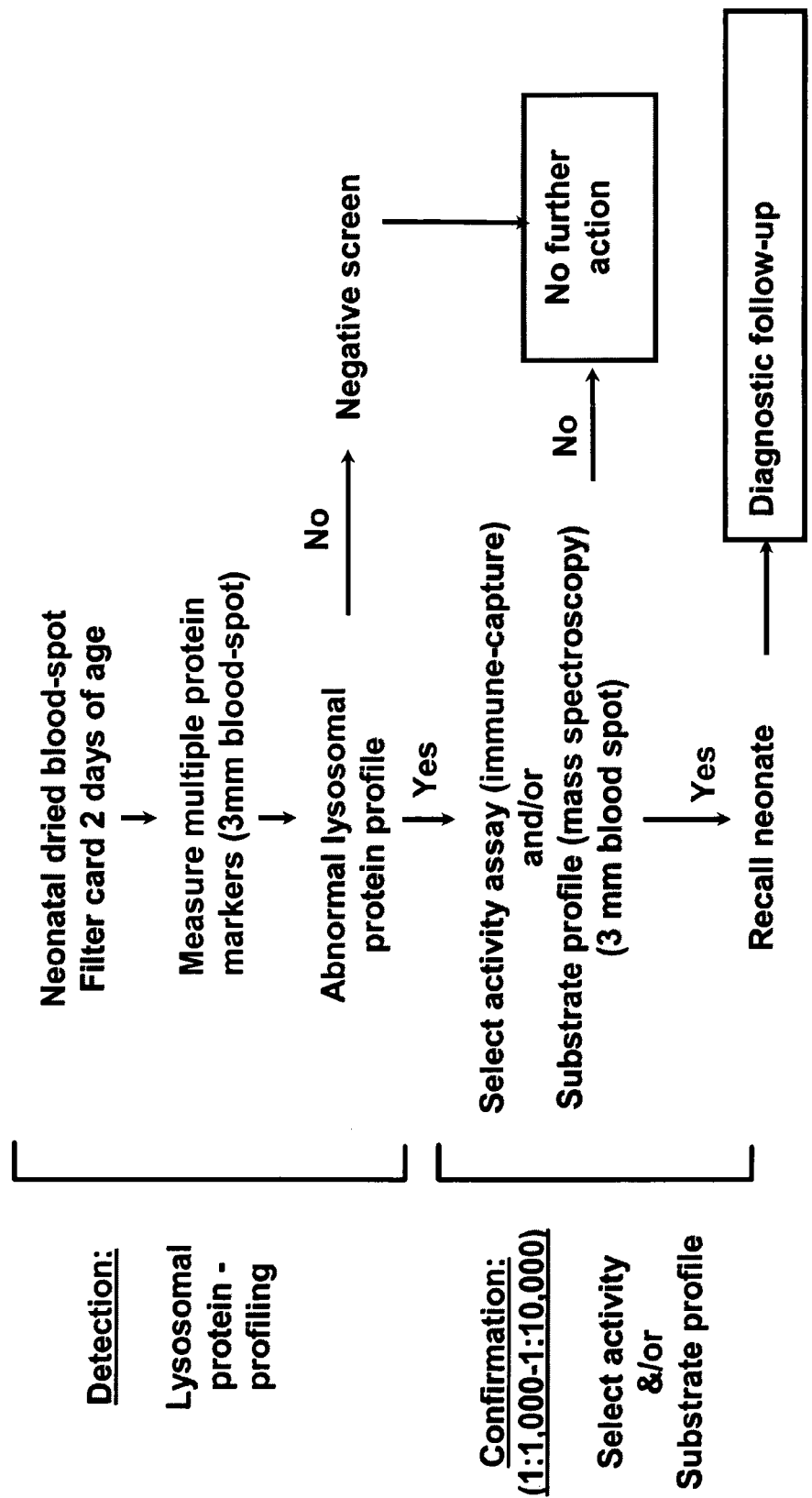
Figure 66:
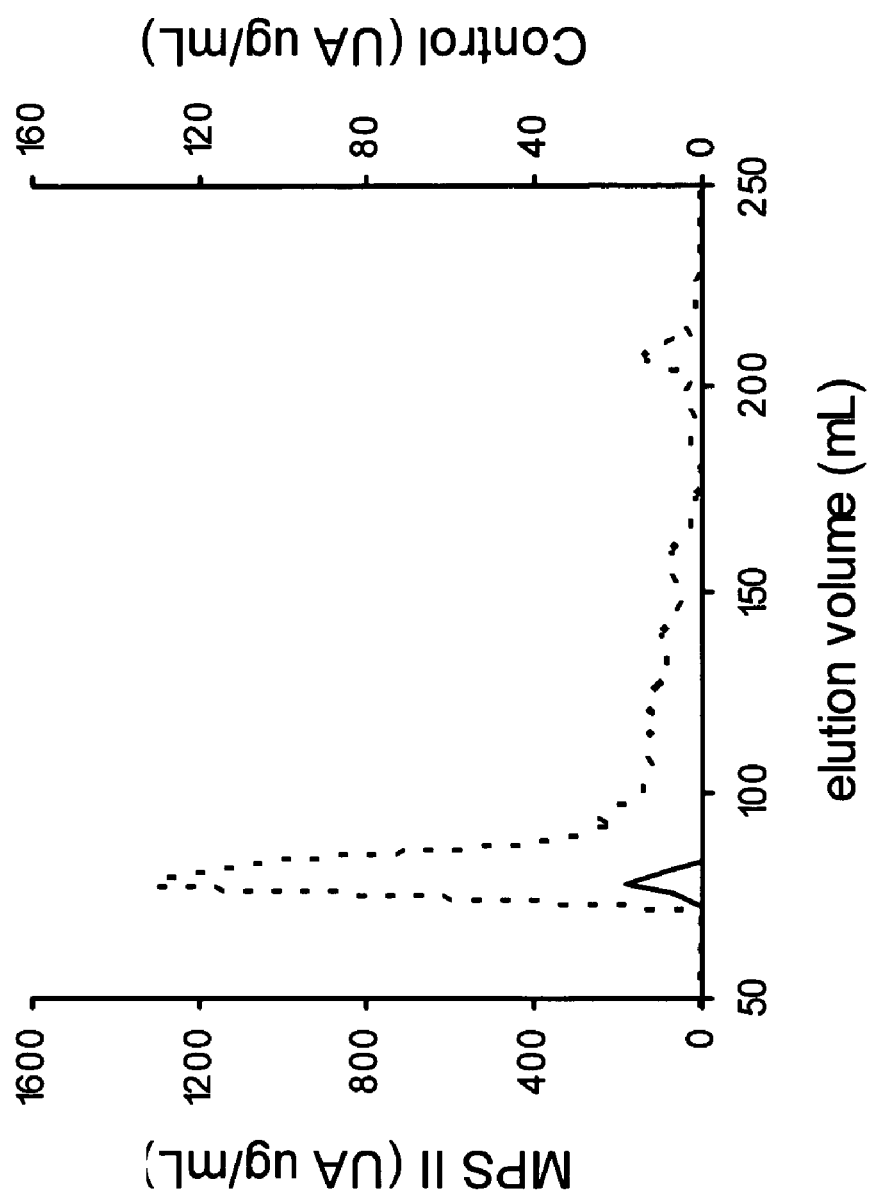

FIG. 19 shows control ranges for protein markers (sulphamidase), wherein the box length is the interquartile range that covers 25th to 75th percentile, the outliers are represented by (circles) each of these cases represent values between 1.5 and 3 box lengths from the upper or lower edge of the box, and the extreme outlier (stars) are cases with values more than 3 box lengths from the upper or lower edge of the box;

FIG. 20 shows control ranges for protein markers (acid sphingomyelinase), wherein the box length is the interquartile range that covers 25th to 75th percentile, the outliers are represented by (circles) each of these cases represent values between 1.5 and 3 box lengths from the upper or lower edge of the box, and the extreme outlier (stars) are cases with values more than 3 box lengths from the upper or lower edge of the box;

FIG. 21 shows control ranges for protein markers (alpha iduronidase), wherein the box length is the interquartile range that covers 25th to 75th percentile, the outliers are represented by (circles) each of these cases represent values between 1.5 and 3 box lengths from the upper or lower edge of the box, and the extreme outlier (stars) are cases with values more than 3 box lengths from the upper or lower edge of the box;

FIG. 22 shows control ranges for protein markers (LAMP-1), wherein the box length is the interquartile range that covers 25th to 75th percentile, the outliers are represented by (circles) each of these cases represent values between 1.5 and 3 box lengths from the upper or lower edge of the box, and the extreme outlier (stars) are cases with values more than 3 box lengths from the upper or lower edge of the box;

FIG. 23 shows control ranges for protein markers (alpha-glucosidase), wherein the box length is the interquartile range that covers 25th to 75th percentile, the outliers are represented by (circles) each of these cases represent values between 1.5 and 3 box lengths from the upper or lower edge of the box, and the extreme outlier (stars) are cases with values more than 3 box lengths from the upper or lower edge of the box;

FIG. 24 shows control ranges for protein markers (beta-glucosidase), wherein the box length is the interquartile range that covers 25th to 75th percentile, the outliers are represented by (circles) each of these cases represent values between 1.5 and 3 box lengths from the upper or lower edge of the box, and the extreme outlier (stars) are cases with values more than 3 box lengths from the upper or lower edge of the box;

FIG. 25 shows control ranges for protein markers (Saposin C), wherein the box length is the interquartile range that covers 25th to 75th percentile, the outliers are represented by (circles) each of these cases represent values between 1.5 and 3 box lengths from the upper or lower edge of the box, and the extreme outlier (stars) are cases with values more than 3 box lengths from the upper or lower edge of the box;

FIG. 26 shows control ranges for protein markers (alpha-galactosidase), wherein the box length is the interquartile range that covers 25th to 75th percentile, the outliers are represented by (circles) each of these cases represent values between 1.5 and 3 box lengths from the upper or lower edge of the box, and the extreme outlier (stars) are cases with values more than 3 box lengths from the upper or lower edge of the box;

FIG. 27 shows control ranges for protein markers (arylsulphatase A), wherein the box length is the interquartile range that covers 25th to 75th percentile, the outliers are represented by (circles) each of these cases represent values between 1.5 and 3 box lengths from the upper or lower edge of the box, and the extreme outlier (stars) are cases with values more than 3 box lengths from the upper or lower edge of the box;

FIG. 28 shows control ranges for protein markers (iduronate-2-sulphatase), wherein the box length is the interquartile range that covers 25th to 75th percentile, the outliers are represented by (circles) each of these cases represent values between 1.5 and 3 box lengths from the upper or lower edge of the box, and the extreme outlier (stars) are cases with values more than 3 box lengths from the upper or lower edge of the box;

FIG. 29 shows control ranges for protein markers (4-sulphatase), wherein the box length is the interquartile range that covers 25th to 75th percentile, the outliers are represented by (circles) each of these cases represent values between 1.5 and 3 box lengths from the upper or lower edge of the box, and the extreme outlier (stars) are cases with values more than 3 box lengths from the upper or lower edge of the box;

FIG. 30 shows LSD affected and control ranges for protein markers (sulphamidase), wherein the box length is the interquartile range that covers 25th to 75th percentile, the outliers are represented by (circles) each of these cases represent values between 1.5 and 3 box lengths from the upper or lower edge of the box, and the extreme outlier (stars) are cases with values more than 3 box lengths from the upper or lower edge of the box;

FIG. 31 shows LSD affected and control ranges for protein markers (acid sphingomyelinase), wherein the box length is the interquartile range that covers 25th to 75th percentile, the outliers are represented by (circles) each of these cases represent values between 1.5 and 3 box lengths from the upper or lower edge of the box, and the extreme outlier (stars) are cases with values more than 3 box lengths from the upper or lower edge of the box;

FIG. 32 shows LSD affected and control ranges for protein markers (alpha-iduronidase), wherein the box length is the interquartile range that covers 25th to 75th percentile, the outliers are represented by (circles) each of these cases represent values between 1.5 and 3 box lengths from the upper or lower edge of the box, and the extreme outlier (stars) are cases with values more than 3 box lengths from the upper or lower edge of the box;

FIG. 33 shows LSD affected and control ranges for protein markers (LAMP-1), wherein the box length is the interquartile range that covers 25th to 75th percentile, the outliers are represented by (circles) each of these cases represent values between 1.5 and 3 box lengths from the upper or lower edge of the box, and the extreme outlier (stars) are cases with values more than 3 box lengths from the upper or lower edge of the box;

FIG. 34 shows LSD affected and control ranges for protein markers (alpha-glucosidase), wherein the box length is the interquartile range that covers 25th to 75th percentile, the outliers are represented by (circles) each of these cases represent values between 1.5 and 3 box lengths from the upper or lower edge of the box, and the extreme outlier (stars) are cases with values more than 3 box lengths from the upper or lower edge of the box;

FIG. 35 shows LSD affected and control ranges for protein markers (beta-glucosidase), wherein the box length is the interquartile range that covers 25th to 75th percentile, the outliers are represented by (circles) each of these cases represent values between 1.5 and 3 box lengths from the upper or lower edge of the box, and the extreme outlier (stars) are cases with values more than 3 box lengths from the upper or lower edge of the box;

FIG. 36 shows LSD affected and control ranges for protein markers (Saposin C), wherein the box length is the interquartile range that covers 25th to 75th percentile, the outliers are represented by (circles) each of these cases represent values between 1.5 and 3 box lengths from the upper or lower edge of the box, and the extreme outlier (stars) are cases with values more than 3 box lengths from the upper or lower edge of the box;

FIG. 37 shows LSD affected and control ranges for protein markers (alpha-galactosidase), wherein the box length is the interquartile range that covers 25th to 75th percentile, the outliers are represented by (circles) each of these cases represent values between 1.5 and 3 box lengths from the upper or lower edge of the box, and the extreme outlier (stars) are cases with values more than 3 box lengths from the upper or lower edge of the box;

FIG. 38 shows LSD affected and control ranges for protein markers (arylsulphatase A), wherein the box length is the interquartile range that covers 25th to 75th percentile, the outliers are represented by (circles) each of these cases represent values between 1.5 and 3 box lengths from the upper or lower edge of the box, and the extreme outlier (stars) are cases with values more than 3 box lengths from the upper or lower edge of the box;

FIG. 39 shows LSD affected and control ranges for protein markers (iduronate-2-sulphatase), wherein the box length is the interquartile range that covers 25th to 75th percentile, the outliers are represented by (circles) each of these cases represent values between 1.5 and 3 box lengths from the upper or lower edge of the box, and the extreme outlier (stars) are cases with values more than 3 box lengths from the upper or lower edge of the box;

FIG. 40 shows LSD affected and control ranges for protein markers (4-sulphatase), wherein the box length is the interquartile range that covers 25th to 75th percentile, the outliers are represented by (circles) each of these cases represent values between 1.5 and 3 box lengths from the upper or lower edge of the box, and the extreme outlier (stars) are cases with values more than 3 box lengths from the upper or lower edge of the box;

FIG. 41 shows control and I-cell ranges for protein markers (sulphamidase; acid sphingomyelinase; alpha-iduronidase; LAMP-1; alpha-glucosidase; beta-glucosidase; Saposin C; alpha-galactosidase; arylsulphatase A; iduronate-2-sulphatase; and 4-sulphatase);

FIG. 42 shows control, MLD and pseudo MLD ranges for arylsulphatase A, wherein the box length is the interquartile range that covers 25th to 75th percentile, the outliers are represented by (circles) each of these cases represent values between 1.5 and 3 box lengths from the upper or lower edge of the box, and the extreme outlier (stars) are cases with values more than 3 box lengths from the upper or lower edge of the box;

FIG. 43 shows control, and multiple sulphatase deficiency values for selected protein markers in Adult, newborn and MSD, wherein the box length is the interquartile range that covers 25th to 75th percentile, the outliers are represented by (circles) each of these cases represent values between 1.5 and 3 box lengths from the upper or lower edge of the box, and the extreme outlier (stars) are cases with values more than 3 box lengths from the upper or lower edge of the box;

FIG. 44 shows a table having the percent identification of LSD using single proteins MLD and pseudo MLD ranges for arylsulphatase A;

FIG. 45 shows a discrimination plot of Gaucher, newborn control, and adult patients using protein ratios (beta-glucosidase and alpha-glucosidease/alpha-galactosidease);

FIG. 46 shows a discrimination plot of Pompe, newborn control, and adult patients using protein ratios (alpha-glucosidase and alpha-iduronidase);

FIG. 47 shows a discrimination plot of Pompe, and newborn control patients using protein ratios (alpha-glucosidase and alpha-iduronidase);

FIG. 48 shows a discrimination plot of MPSII, newborn control, and adult patients using protein ratios (iduronate-2-sulphantase and LAMP-1);

FIG. 49 shows a discrimination plot of MPSII, newborn control, and adult patients using protein ratios (iduronate-2-sulphantase and acid sphingomyelinase);

FIG. 50 shows a table indicating the percentage identification of LSD using protein ratios;

FIG. 51 shows a retrospective analysis of newborns from Guthrie card samples (alpha-galactosidase in Denmark, Fabry, Gaucher, MPSII, MPSIIIA, and Pompe), wherein the box length is the interquartile range that covers 25th to 75th percentile, the outliers are represented by (circles) each of these cases represent values between 1.5 and 3 box lengths from the upper or lower edge of the box, and the extreme outlier (stars) are cases with values more than 3 box lengths from the upper or lower edge of the box;

FIG. 52 shows a retrospective analysis of newborns from Guthrie card samples (alpha-glucosidase in Denmark, Fabry, Gaucher, MPSII, MPSIIIA, and Pompe), wherein the box length is the interquartile range that covers 25th to 75th percentile, the outliers are represented by (circles) each of these cases represent values between 1.5 and 3 box lengths from the upper or lower edge of the box, and the extreme outlier (stars) are cases with values more than 3 box lengths from the upper or lower edge of the box;

FIG. 53 shows a retrospective analysis of newborns from Guthrie card samples (beta-glucosidase in Denmark, Fabry, Gaucher, MPSII, MPSIIIA, and Pompe), wherein the box length is the interquartile range that covers 25th to 75th percentile, the outliers are represented by (circles) each of these cases represent values between 1.5 and 3 box lengths from the upper or lower edge of the box, and the extreme outlier (stars) are cases with values more than 3 box lengths from the upper or lower edge of the box;

FIG. 54 shows a retrospective analysis of newborns from Guthrie card samples (sulphamidase in Denmark, Fabry, Gaucher, MPSII, MPSIIIA, and Pompe), wherein the box length is the interquartile range that covers 25th to 75th percentile, the outliers are represented by (circles) each of these cases represent values between 1.5 and 3 box lengths from the upper or lower edge of the box, and the extreme outlier (stars) are cases with values more than 3 box lengths from the upper or lower edge of the box;

FIG. 55 shows a retrospective analysis of newborns from Guthrie card samples (iduronate-2-sulphatase in Denmark, Fabry, Gaucher, MPSII, MPSIIIA, and Pompe), wherein the box length is the interquartile range that covers 25th to 75th percentile, the outliers are represented by (circles) each of these cases represent values between 1.5 and 3 box lengths from the upper or lower edge of the box, and the extreme outlier (stars) are cases with values more than 3 box lengths from the upper or lower edge of the box;

FIG. 56 shows a retrospective analysis of newborns from Guthrie card samples (sulphamidase; acid sphingomyelinase; alpha-iduronidase; LAMP-1; alpha-glucosidase; beta-glucosidase; Saposin C; alpha-galactosidase; arylsulphatase A; iduronate-2-sulphatase; and 4-sulphatase);

FIG. 57 shows a retrospective analysis plot of Denmark, Fabry, Gaucher, MPSII, MPSIIIA, and Pompe newborn Guthrie card samples (alpha-glucosidase and alpha-iduronidase);

FIG. 58 shows a retrospective analysis plot of Denmark, Fabry, Gaucher, MPSII, MPSIIIA, and Pompe newborn Guthrie card samples (beta-glucosidase and saposin C);

FIG. 59 shows a retrospective analysis plot of Denmark, Fabry, Gaucher, MPSII, MPSIIIA, and Pompe newborn Guthrie card samples (beta-glucosidase and acid sphingomyelinase);

FIG. 60 shows a table of the percentage of total identified LSD;

FIG. 61 shows a table of the percentage of identified LSD using single proteins;

FIG. 62 shows a table of the percentage of identified LSD affected newborns using retrospective analysis;

FIG. 63 shows the multiplex neonatal screening strategy for LSD;

FIG. 64 shows a table of proposed structure of MPS II Oligosaccharides derived from dermatan sulfate;

FIG. 65 shows a table of proposed structure of MPS II Oligosaccharides derived from heparan sulfate;

FIG. 66 shows Elution profile of control and MPS II urine from Bio-Gel P4. GAGs were isolated from control and MPS II patient urine by a combination of anion exchange and size exclusion chromatography. Fractions from the Bio-Gel P4 column were assayed for UA equivalents. The solid and broken lines represent elution from the Bio-Gel P4 column of control and MPS II urine, respectively.

Figure 67:
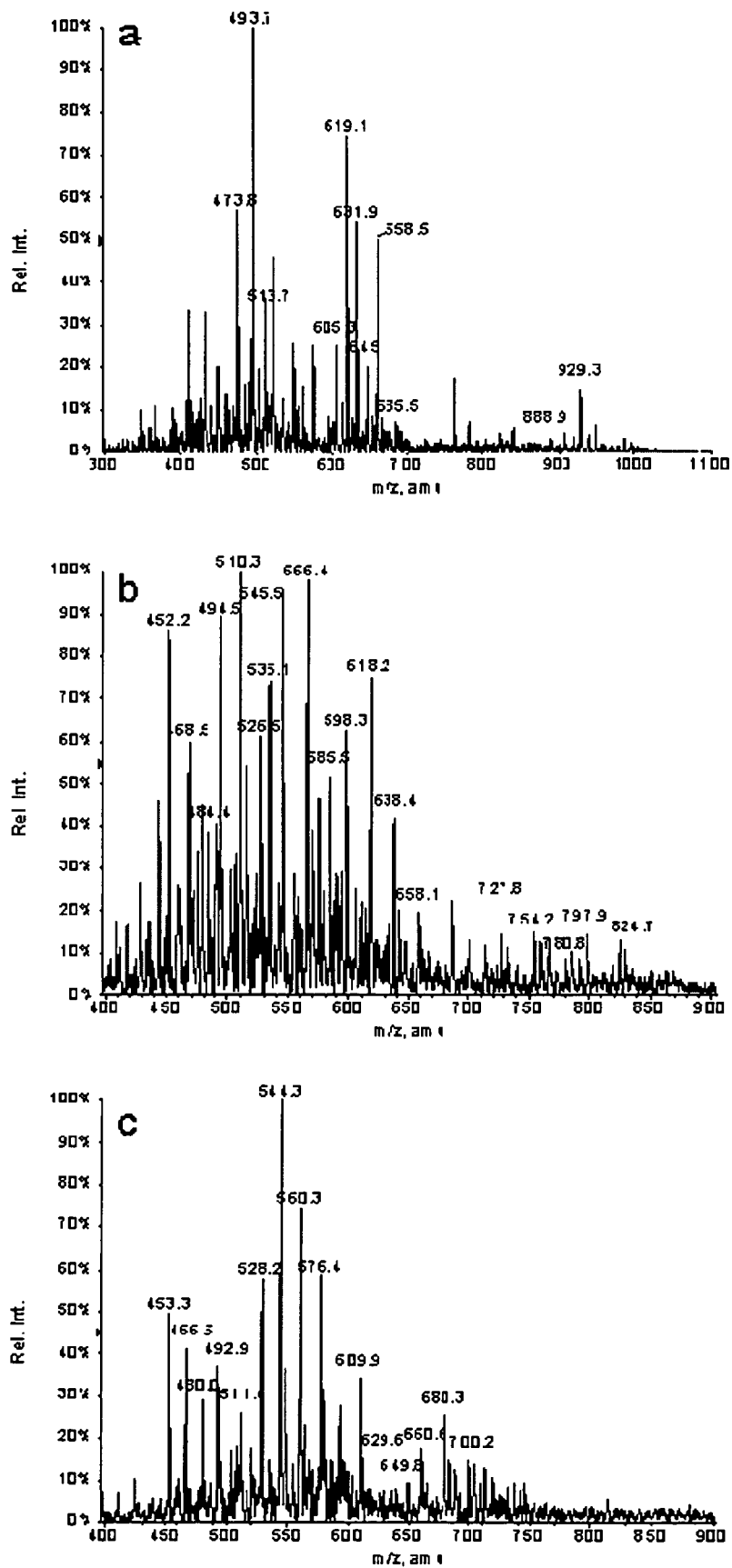

FIG. 67 shows ESI-MS of selected oligosaccharides. Eluate fractions from the Bio-Gel P4 column were lyophilised, derivatized with PMP and analyzed by ESI-MS. Panel a shows ESI-MS of heptasaccharides; [UA-HN]$_2$-UA-HNAc-UA with 3-6 S of $[M-3H]^{-3}$ ions 605.3, 631.9, 658.5, 685.5 and with 4-6 S $[M-4H]^{-4}$ ions 473.8, 493.7, 513.7; and UA-HN-[UA-HNAc]$_2$-UA with 2-3 S of $[M-2H]^{-2}$ ions 888.9, 929.3 and with 3-4 S $[M-3H]^{-3}$ ions 619.1, 645.7. Panel b shows ESI-MS of an octasaccharide; [UA-HNAc]$_4$ with 4-6 S $[M-3H]^{-3}$ ions 727.8, 754.2, 780.8 and $[M-4H]^{-4}$ ions 545.5, 565.4, 585.5, and with 5-7 S $[M-5H]^{-5}$ ions 452.2, 468.5, 484.4; a nonasaccharide UA-HN-(UA-HNAc)$_3$-UA with 5-6 S $[M-3H]^{-3}$ ions 797.9, 824.7, with 5-8 S $[M-4H]^{-4}$ ions 598.3, 618.2, 638.4, 658.1 and with 4-6 S $[M-5H]^{-5}$ ions 494.5, 510.3, 526.5. Panel c shows ESI-MS of decasaccharides; (UA-HNAc)$_5$ with 5-7 S $[M-4H]^{-4}$ ions 660.6, 680.3, 700.2, with 4-8S $[M-5H]^{-5}$ ions 511.4, 528.2, 544.3, 560.3, 576.4, with 6-9 S $[M-6H]^{-6}$ ions 453.3, 466.6, 480, 492.9; UA-HN-[UA-HNAc]$_4$ with 3-5 S $[M-4H]^{-4}$ ions 609.9, 629.6, 649.8.

Figure 68:
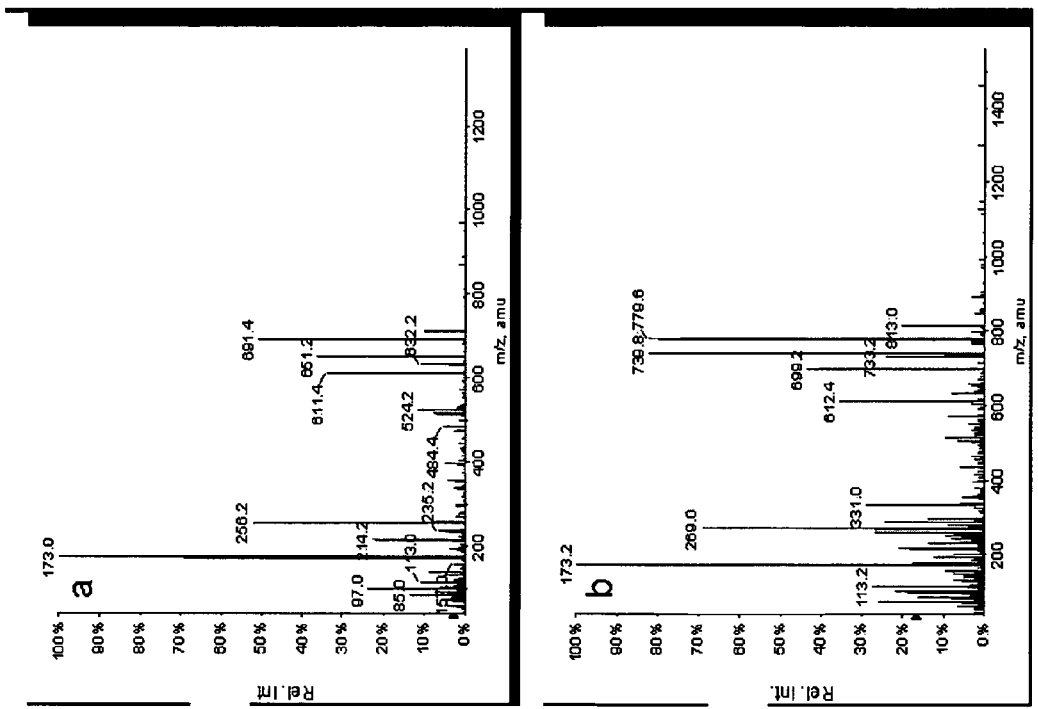

FIG. 68 shows Product ion spectra of oligosaccharides from a MPS II patient. Eluate fractions from the Bio-Gel P4 column were lyophilised, derivatized with PMP and analyzed by ESI-MS/MS. Panel a shows the product ion spectra of a tetrasaccharide UA-HN-UA-HNAc with 4S. Products of the $[M-2H]^{2-}$, m/z 691.4, were obtained. Major product ions at m/z 651.2 $[M-S-2H]^{2-}$, m/z 611.4 $[M-2S-2H]^{2-}$, m/z 173 $[PMP-H]^-$ and m/z 256 corresponding to a PMP molecule with a fragmented HNAc. Panel b shows the product ion spectra of a pentasaccharide UA-HN-UA-HNAc-UA with 4S. Products of the $[M-2H]^{2-}$, m/z 779.6, were obtained. Major product ions at m/z 739.8 $[M-S-2H]^{2-}$, m/z 699.2 $[M-2S-2H]^{2-}$, m/z 173 $[PMP-H]^-$ m/z 331 $[PMP-UA-H]^-$ and 269 corresponding to a PMP molecule with a fragmented UA.

Figure 69:
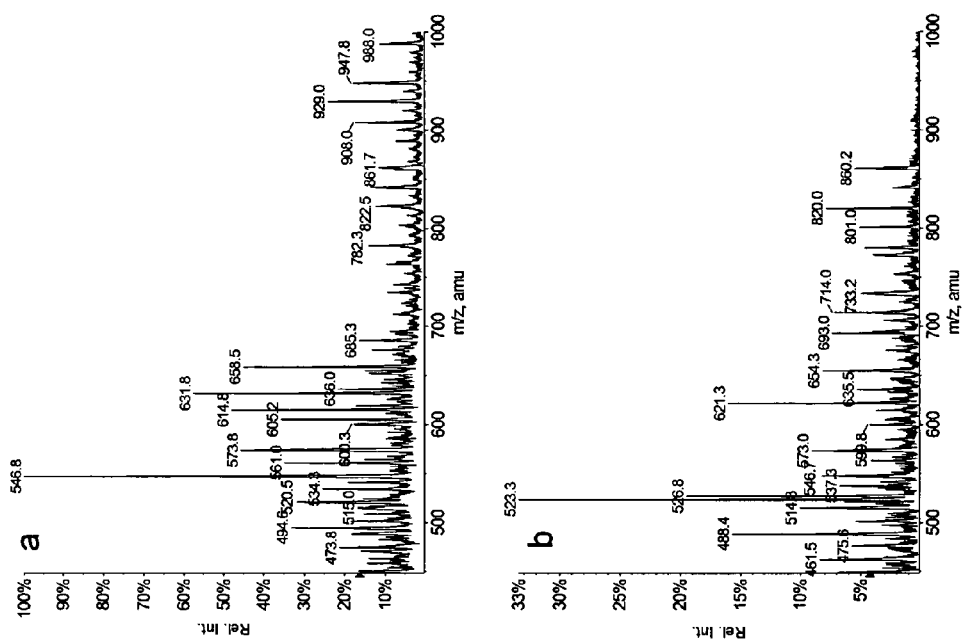

FIG. 69 shows Mass spectra of oligosaccharides following recombinant enzyme digests. Negative ion ESI-MS of pooled hexasaccharide and heptasaccharide isolated from MPS II urine. Panel a shows ESI-MS of a heptasaccharide (UA-HN-UA-HN-UA-HNAc-UA); with 3-5 S producing $[M-2H]^{-2}$ ions at m/z 908, 947.8, 988, with 3-6 S producing $[M-3H]^{-3}$ ions at m/z 605.2, 631.8, 658.5, 685.3 and with 4-6 S producing $[M4H]^{-4}$ ions at m/z 473.8, 494.6. A hexasaccharide (UA-HNAc-UA-HNAc-UA-HNAc); with 1-4 S producing $[M-2H]^{-2}$ ions at m/z 782.3, 822.5, 861.7 and $[M-3H]^{-3}$ ions at m/z 520.5, 546.8, 573.8, 600.8. Panel b shows the same pooled heptasaccharide and hexasaccharide from MPS II urine following treatment with recombinant I2S and IDUA. The loss of S (80 amu) and IdoA (176 amu) from the heptasaccharide results in a hexasaccharide (HN-UA-HN-UA-HNAc-UA); with 2-4 S producing $[M-2H]^{-2}$ ions at m/z 779.7, 820, 860.8 and $[M-3H]^{-3}$ ions 546.7, 573, 599.8. The loss of S and IdoA from the hexasaccharide results in a pentasaccharide (HNAc-UA-HNAc-UA-HNAc); with 1-3 S producing $[M-2H]^{-2}$ ions at m/z 654.3, 693, 733.2 and $[M-3H]^{-3}$ ions at m/z 461.3, 488.5.

Figure 70:
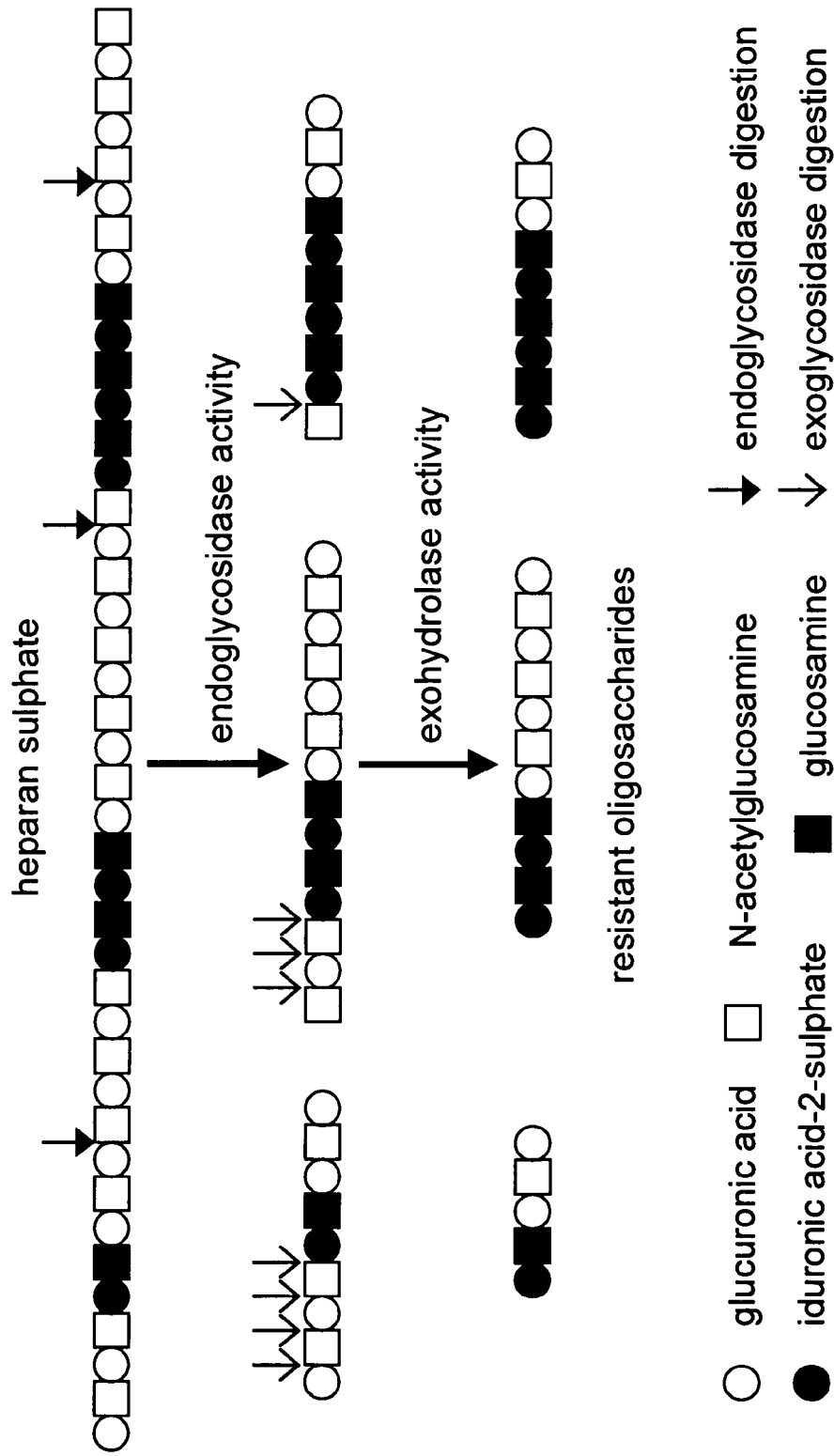

FIG. 70 shows Generation of HS-derived oligosaccharides in MPS II. Following endohydrolase action by heparanase on the regions of low sulphation, exoenzymes involved in the breakdown of HS act sequentially until a IdoA-2S residue is reached at the end of a region of high sulphation. Further degradation of the oligosaccharide is prevented by the deficiency of the iduronate-2-sulphatase. An analogous scheme where the endohydrolase acts on the GlcNAc-GlcA bonds in the low sulphation region is also proposed to account for the oligosaccharides with HNAc at the reducing terminus. A similar scheme involving an endo-N-acetylglucoasminidase activity is also proposed to account for the HS derived oligosaccharides in Table 2 series 4 (in FIG. 65).

SUMMARY

Lysosomal Storage Disorders ("LSDs") represent a group of over 40 distinct genetic diseases that generally affect young children. Individuals that are affected with a LSD present a wide range of clinical symptoms that depend upon the specific disorder or a particular genotype involved. The present invention is generally related to a multiple screening diagnostic for LSD and related diseases. More particularly, this invention pertains to compounds, reagents, and methods for identifying and quantifying multiple target enzymes and proteins that are used to accurately diagnose a LSD. These target enzymes and proteins are naturally present in biological fluids or tissues of patients. The invention also pertains to a Multiplexing Bead Technology for simultaneous screening of specific LSD enzymes.

One aspect of the current invention is a composition used for detection of a LSD. The composition comprises a capture antibody capable of binding an epitope of a target antigen, and a microsphere having the capture antibody conjugated to the microsphere. The target antigen is selected from the group consisting of: saposin (SeqID No. 1), LAMP-1 (SeqID No. 2), α-iduronidase (SeqID No. 3), α-glucosidase (SeqID No. 4), β-glucosidase (SeqID No. 5), 2-sulphatase (SeqID No. 6), 4-sulphatase (SeqID No. 7), α-galactosidase (SeqID No. 8), sphingomyelinase (SeqID No. 9), 3-sulphatase (SeqID No. 10) and sulphamidase. The microsphere having the conjugated capture antibody has a preferred diameter of about 5 μm and at least a first fluorophore and a second fluorophore. The first fluorophore being spectrally distinct from the second fluorophore. The composition may further comprise a detection antibody, wherein the detection antibody is capable of binding the target antigen, and the detection antibody may be different from the capture antibody. The detection antibody is conjugated to any detectable label known in the art (e.g. a fluorescent label).

DETAILED DESCRIPTION

Terms

The term "a" or "an" as used herein in the specification may mean one or more. As used herein in the claim(s), when used in conjunction with the word "comprising", the words "a" or "an" may mean one or more than one. As used herein "another" may mean at least a second or more.

The term "animal," "subject," or "patient" as used herein may be used interchangeably and refers to any species of the animal kingdom. In preferred embodiments it refers more specifically to humans.

The term "biomolecule" as used herein is understood to represent the target molecule, such as a protein, an antibody, a metabolite, a DNA sequence, an RNA sequence, a biologic with activities used or measured for the purposes multiplexing and profiling of target biomolecules, or a combination thereof, for the composition and method of determining LSD, used in administering, monitoring, or modifying an LSD therapy.

The term "clinical status" as used herein refers to patients that are being studied or treated by physicians for a LSD.

The term "comprise," or variations such as "comprises" or "comprising," as used herein may be used to imply the inclusion of a stated element or integer or group of elements or integers, but not the exclusion of any other element or integer or group of elements or integers.

The term "fluorophore" as used herein refers to any fluorescent compound or protein that can be used to quantify the LSD antigens.

The term "normalize" as used herein refers to bringing a target, reference, or other samples into conformity with a standard, pattern, model, etc. For example, in one embodiment, urine samples from LSD patients and non-LSD patients were normalized by using a 1 μmol equivalent of creatinine from each sample.

The term "phenotype" as used herein refers to the manifest characteristics of an organism collectively, including anatomical and psychological traits that result from both its heredity and its environment.

The term "preclinical status" as used herein refers to the period of a disease before any of the clinical symptoms appear.

The term "lysosomal storage disorder ("LSD") associated biomolecule" as used herein refers to any biomolecule that has been linked to any LSD. In preferred embodiments, a LSD associated biomolecule includes, but is not limited to: saposin (SeqID No. 1), LAMP-1 (SeqID No. 2), α-iduronidase (SeqID No. 3), α-glucosidase (SeqID No. 4), β-glucosidase (SeqID No. 5), 2-sulphatase (SeqID No. 6), 4-sulphatase (SeqID No. 7), α-galactosidase (SeqID No. 8), sphingomyelinase (SeqID No. 9), sulphamidase, or 3-sulphatase (SeqID No. 10), or sulphamidase, LAMP-2, α-galactosidase A, iduronate-2-sulphatase, α-iduronidase, N-acetylgalactosamine 4-sulphatase, galactose 6-sulphatase, acid sphingomyelinase, galactocerebrosidase, arylsulphatase A, saposin B, heparan-N-sulphatase, α-N-acetylglucosaminidase, acetylCoA: glucosamine N-acetyltransferase, N-acetylglucosamine 6-sulphatase, β-galactosidase, β-glucuronidase, aspartylglucosaminidase, acid lipase, β-hexosaminidase A, β-hexosamindase B, GM2-acitvator, acid ceramidase, α-L-fucosidase, α-D-mannosidase, β-D-mannosidase, neuraminidase, phosphotransferase, phosphotransferase g-subunit, palmitoyl protein thioesterase, tripeptidyl peptidase I, cathespsin K, α-galactosidase B, or sialic acid transporter. As shown below, Table 1 indicates some enzyme deficiencies for LSDs.

The term "reference quantity" as used herein refers to a known, normalized amount of a LSD biomarker in a biological fluid. The reference quantity is determined from an animal, or group of animals having a defined clinical status, preclinical status, or phenotype of a LSD disease. The reference quantity may refer to a table compiled from various animals or groups of animals having correlations between relative amounts of LSD biomarkers in a biological fluid, and a known clinical status, preclinical status, or phenotype.

Other Abbreviations: "MPS," mucopolysaccharidosis; "GAG," glycosaminoglycans; "HS," heparan sulfate; "DS," dermatan sulfate; "IDUA," α-L-iduronidase; "I2S," iduronate-2-sulfatase; "ESI-MS/MS," electrospray ionization-tandem mass spectrometry; "IdoA," α-L-iduronic acid; "HN," hexosamine; "UA," uronic acid; "GlcN," glucosamine; "GlcNAc," N-acetylglucosamine; "GalNAc," N-acetylgalactosamine; "HNAc," N-acetylhexosamine; "MRM," multiple-reaction monitoring.

Lysosomal Storage Disorders

The LSD's represent a group of over 40 distinct genetic diseases that generally affect young children. Patients are usually born without the visible features of a LSD, but early stage symptoms can quickly develop into a progressive clinical concern. Although some effective LSD therapies have been developed, it is paramount that therapy be started as soon as the LSD has been diagnosed. Unfortunately, a clinical diagnosis of a LSD often requires multiple visits to a range of specialists requiring time-consuming, invasive, complex, inconvenient, and expensive assays. The current process for an accurate diagnosis of LSD for a patient not having a family history of LSD can take months to years, which is unacceptable when effective LSD therapies are needed earlier.

It is generally recognized that the accumulation of storage materials in the lysosomes of LSD affected individuals will increase from approximately 1% to as much as 50% of the total cellular volume. Certain lysosomal proteins are present at altered levels in the LSD affected individuals (Meikle et al., 1997; Hua et al., 1998). Unless stated otherwise all regents were of analytical grade and were obtained from Sigma Chemical Company, MO USA. Preparation of recombinant proteins, antibodies and calibration standards for Lamp-1 and saposin C. Recombinant Lamp-1 (minus tail) was isolated from CHO-K1 cells as detailed in Isaac et al [Isaac E L, Karageorgous L E, Brooks D A, Hopwood J J and Meikle P J. Experimental Cell Research 2000, 254: 204-209]. Recombinant Saposin C was a gift from Dr G A Grabowski and was prepared by the method of Qi and Grabowski [Qi T L and Grabowski G A J Biol Chem 1994, 269: 16746-16753].

Identifying "at Risk" Individuals. In order to demonstrate that identification of two or more LSD biomarkers can increase the accuracy of LSD diagnosis, methods that combined the identification of LAMP-1 proteins and saposin C proteins in patients samples were evaluated.

The anti Lamp-1 monoclonal antibody (BB6) was generated using intact Lamp-1 protein by the method of Carlsson and Fukada [Carlsson S R and Fukada M JBC (1989) 264 (34): 20526-20531] and 7B2 (anti Saposin C) monoclonal antibody was produced using the recombinant protein by the method described in [Zola H and Brooks D. Techniques for the production and characterization of monoclonal hybridoma antibodies. In: Hurrell JGR, ed. Monoclonal hybridoma antibodies: techniques and applications. Boca Raton, Fla.: CRC Press, 1982:1-57]. Polyclonal antibodies were generated for both Lamp-1 and Saposin C by immunizing separate rabbits with 200 μg of each recombinant protein per inoculation (four inoculations in total) based upon the method of Leonova et al, 1996, [JBC 271:17312-20]. All antibodies were purified using 5 ml Hitrap™ Protein G affinity column (Pharmacia, Uppsala, Sweden). The polyclonal antibodies were affinity purified further by column chromatography using their respective recombinant proteins coupled to Affi-Gel® 10 Gel (Bio-Rad #153-6046, CA, USA) according to manufacturers instructions.

Blood spot calibrators containing final concentrations of 2000, 1000, 500, 250, 62.5 and 0 μg/L for Lamp-1 and saposin C were prepared as detailed in Umapathysivam et al [Umapathysivam K, Whittle A M, Ranieri E, Bindloss C, Ravenscroft E M, van Diggelen O P, Hopwood J J and Meikle P J Clin Chem 46(9): 1318-1325 2000]. Two blood spot controls containing low (Lamp-1 400 µg/L; saposin 200 µg/L) and high (Lamp-1 800 µg/L; saposin C 500 µg/L) protein concentrations were similarly prepared.

Quantification of Lamp-1 and Saposin C in Dried Blood Spots Containing EDTA. Lamp-1 and Saposin C were measured in dried blood spots using one step three tier, time-delayed fluorescence immunoassays. Microtiter plates (Labsytems, Helsinki, Finland #95029180) were coated with either BB6 or 7B2 at a concentration of 5 µg/L in 0.1 mol/l NaHCO3, pH 8.3 and incubated covered for approximately 16 hrs at 4° C. Plates were washed twice with wash buffer (0.25 mol/l NaCl, 0.02 mol/l Tris containing 0.005% Tween 20 (BDH, Poole, England) and 0.002% Thiomerosal, pH7.8) Non-specific binding sites on the plates were blocked by the addition of 100 µl of 0.25M NaCl, 0.02M Tris containing 0.5% skim milk powder (Diploma, Bonlac Foods, Victoria, Australia), pH 7.8, per well. After a two hour incubation at room temperature, the microtiter plates were washed twice with 0.25M NaCl, 0.02M Tris pH 7.8 and tapped dry before being lyophilized and stored desiccated at 4° C. prior to use.

Standard calibrators, controls and patient dried blood spots were placed in duplicate into the coated microtiter wells with 200 µl of either polyclonal antibody diluted in assay buffer (0.15 mol/l NaCl, 0.05 mol/L Tris, 20 µmol/L Diethylene triamine-penta-acetic acid, containing 0.01% Tween 40, 0.5% bovine serum albumin (A-9647), 0.05% bovine γ-globulin (G-7516), and 0.05% sodium azide, pH 7.8). The antibodies were used at a final concentration of 200 µg/L and 400 µg/L for the anti-Lamp-1 and anti saposin C polyclonal respectively. The plates were covered and incubated at room temperature for one hour with shaking, then placed overnight at 4° C., followed by an hour incubation with shaking at room temperature. The blood spots were removed by suction and the plates washed six times with wash buffer. After dilution in assay buffer to final concentration of 0.1 µg/ml, 100 µl of anti rabbit europium labeled antibody (Wallac, Finland #AD0105), was added to every well and incubated for one hour at room temperature with shaking. After washing the plates a final six times with wash buffer, 200 µl of DELFIA® Enhancement solution (Wallac, Finland) was added per well and the plates incubated at room temperature for ten minutes with shaking. Fluorescence was measured on a DELFIA® 1234 Research Fluorometer (Wallac, Finland). The concentrations of Lamp-1 and Saposin C in the blood spots were calculated using spline fit curves generated by Multicalc Data Analysis software (version 2.4 Wallac, Finland).

Although certain lysosomal target proteins are present at altered levels in the affected individuals, the current individual screening assays may be inaccurate due to variations among individual samples. For example, a given sample is assumed to contain an average number of lysosomes or white blood cells ("WBC"), however variations in these values between individual samples are not typically considered. Thus, variations in an individual having a deficiency in a particular LSD biomolecule (e.g. lysosomal target protein), but also having an unusually high WBC count or high numbers of lysosomes in the test sample may return an assay result that is consistent for individuals that do not have a LSD. Consequently, if WBC or high numbers of lysosomes were controlled in the sample preparation a large inaccuracy could be avoided, and a proper diagnosis could be made during the first round of LSD screening.

Determining the quantities of multiple target enzymes increases the accuracy of diagnosing a specific LSD as compared to any single assay. For example, using immunoquantification assays directed toward identifying the levels of the lysosome-associated membrane proteins ("LAMPs"), such as LAMP-1 or LAMP-2, in an "at-increased-risk" group will identify up to 65% of LSD affected individuals. However, the combination of LAMP's with one of the saposins increases identification of LSD affected individuals to approximately 85%. Therefore, a method to identify two or more biomarkers simultaneously would increase the accuracy of LSD diagnosis and reduce the time and cost for each assay. A Multiplexing Bead Technology is used to simultaneously detect specific at least 2 LSD target antigens is described below or in Table 1.

TABLE 1

Enzymes deficient in some common lysosomal storage disorders

| Disease | Clinical Phenotype | Enzyme Deficiency | Australian Prevalence |
|---|---|---|---|
| Gaucher disease types I/II/III | Gaucher disease | Glucocerebrosidase (β-glucosidase) | 1 in 57,000 |
| Cystinosis | | Cystine transporter | 1 in 192,000 |
| Fabry disease | Fabry disease | α-Galactosidase A | 1 in 117,000 |
| Glycogen storage disease II | Pompe disease | α-Glucosidase | 1 in 146,000 |
| Mucopolysaccharidosis type I | Hurler/Scheie syndrome | α-L-Iduronidase | 1 in 88,000 |
| Mucopolysaccharidosis type II | Hunter syndrome | Iduronate-2-sulphatase | 1 in 136,000 |
| Mucopolysaccharidosis type VI | Maroteaux-Lamy syndrome | N-acetylgalactosamine 4-sulphatase | 1 in 235,000 |
| Mucopolysaccharidosis type IVA | Morquio syndrome | Galactose 6-sulphatase | 1 in 169,000 |
| Niemann-Pick disease types A/B | Niemann-Pick disease | Acid sphingomyelinase | 1 in 248,000 |
| Globoid cell leucodystrophy | Krabbe disease | Galactocerebrosidase | 1 in 201,000 |
| Metachromatic leucodystrophy | | Arylsulphatase A | 1 in 92,000 |
| Metachromatic leucodystrophy | | Saposin B | |
| Mucopolysaccharidosis type IIIA | Sanfilippo syndrome | Heparan-N-sulphatase | 1 in 114,000 |
| Mucopolysaccharidosis type IIIB | Sanfilippo syndrome | α-N-Acetylglucosaminidase | 1 in 211,000 |
| Mucopolysaccharidosis type IIIC | Sanfilippo syndrome | AcetylCoA:N-acetyltransferase | 1 in 1,407,000 |
| Mucopolysaccharidosis type IIID | Sanfilippo syndrome | N-Acetylglucosamine 6-sulphatase | 1 in 1,056,000 |
| Mucopolysaccharidosis type IVB | Morquio syndrome | β-Galactosidase | |
| Mucopolysaccharidosis type VII | Sly | β-Glucuronidase | 1 in 2,111,000 |
| Niemann-Pick disease type C1 | Niemann-Pick disease | Cholesterol trafficking | 1 in 211,000 |
| Niemann-Pick disease type C2 | Niemann-Pick disease | Cholesterol trafficking | |
| Aspartylglucosaminuria | | Aspartylglucosaminidase | 1 in 2,111,000 |

TABLE 1-continued

Enzymes deficient in some common lysosomal storage disorders

| Disease | Clinical Phenotype | Enzyme Deficiency | Australian Prevalence |
|---|---|---|---|
| Cholesterol ester storage disease | Wolman disease | Acid lipase | 1 in 528,000 |
| GM1-Gangliosidosis types I/II/III | | β-Galactosidase | 1 in 384,000 |
| GM2-Gangliosidosis type I | Tay Sachs disease | β-Hexosaminidase A | 1 in 201,000 |
| GM2-Gangliosidosis type II | Sandhoff disease | β-Hexosaminidase A & B | 1 in 384,000 |
| GM2-Gangliosidosis | | GM2-activator deficiency | |
| Farber Lipogranulomatosis | Farber disease | Acid ceramidase | |
| Fucosidosis | | α-L-Fucosidase | >1 in 2,000,000 |
| Galactosialidosis types I/II | | Protective protein | |
| α-Mannosidosis types I/II | | α-D-Mannosidase | 1 in 1,056,000 |
| β-Mannosidosis | | β-D-Mannosidase | |
| Mucolipidosis type I | Sialidosis types I/II | Neuraminidase | |
| Mucolipidosis types II/III | I-cell disease; | Phosphotransferase | 1 in 325,000 |
| Mucolipidosis type IIIC | pseudo-Hurler polydystrophy | Phosphotransferase g-subunit | |
| Mucolipidosis type IV | | Unknown | |
| Multiple sulphatase deficiency | | Multiple sulphatases | 1 in 1,407,000 |
| Neuronal Ceroid Lipofuscinosis, CLN1 | Batten disease | Palmitoyl protein thioesterase | |
| Neuronal Ceroid Lipofuscinosis, CLN2 | Batten disease | Tripeptidyl peptidase I | |
| Neuronal Ceroid Lipofuscinosis, CLN3 | Vogt-Spielmeyer disease | Protein function not known | |
| Neuronal Ceroid Lipofuscinosis, CLN5 | Batten disease | Protein function not known | |
| Neuronal Ceroid Lipofuscinosis, CLN8 | Northern Epilepsy | Protein function not known | |
| Pycnodysostosis | | Cathepsin K | |
| Sialic acid storage disease | Schindler disease | α-Galactosidase B | |
| Sialic acid storage disease | Sialuria; salla disease | Sialic acid transporter | 1 in 528,000 |

Prevalence figures quoted from Miekle et al., JAMA 281: 249-254 (1999). Prevalence and ratio of lysosomal storage disorders may vary from country to country

Example 1

Multiplexing Bead Technology and Target LSD Proteins. The Multiplexing Bead Technology is built around 3 core technologies. The first is the family of fluorescently dyed microspheres having bound biomolecules. The second is a flow cytometer with 2 lasers and associated optics to measure biochemical reactions that occur on the surface of the microspheres, and the third is a high-speed digital signal processor to efficiently manage the fluorescent output. Bio-Rad (Hercules, Calif.), provides a commercially available protein array system called the "Bio-Plex™". The Bio-Plex™ protein array system includes fluorescently dyed microspheres, a flow cytometer with 2 lasers and associated optics, and a high-speed digital signal processor. However, neither the Bio-Plex™ protein array system nor any other commercially available systems include any specific biomolecules, methods, compounds, or reagents needed for the simultaneous screening of specific LSD enzymes.

Figure 1:
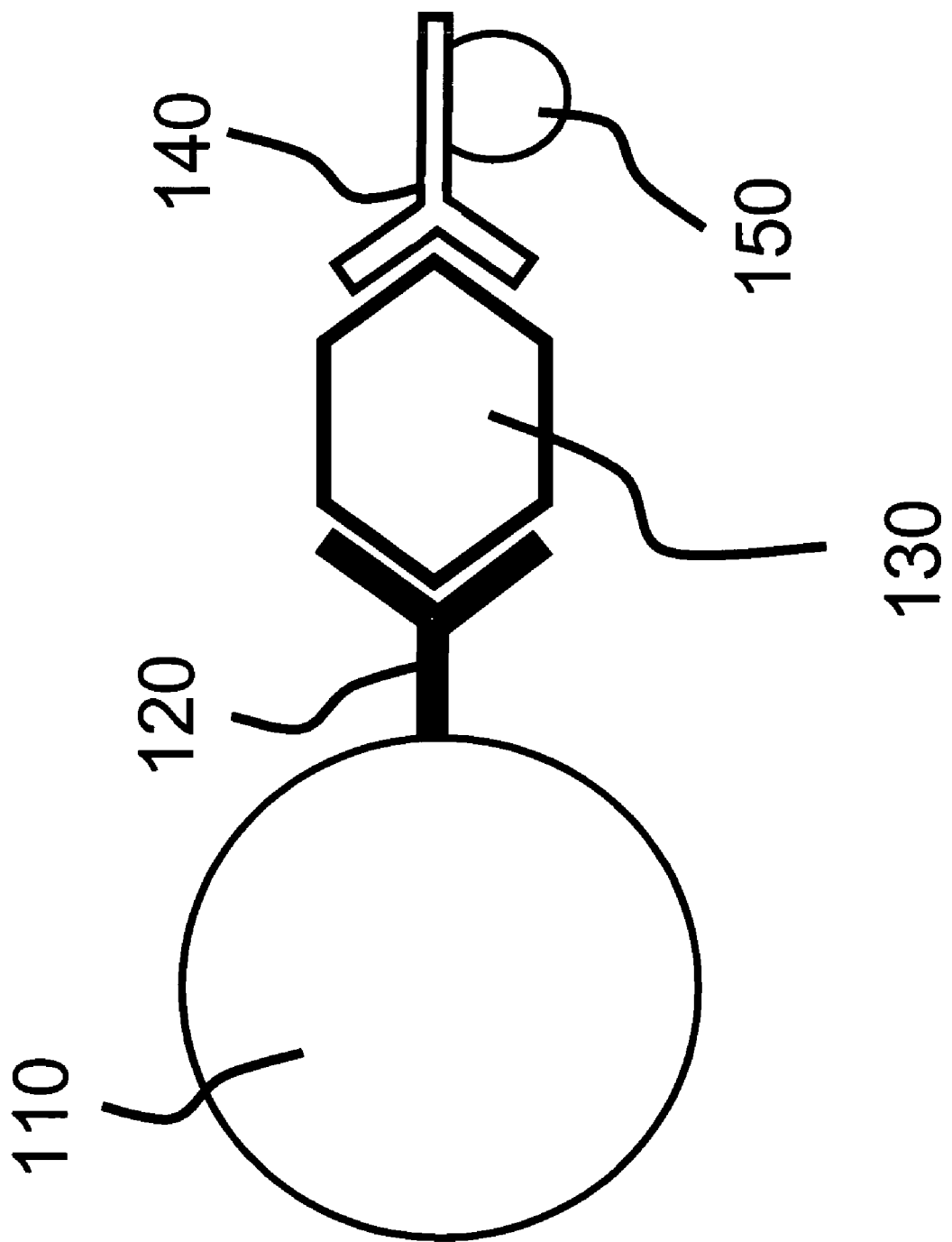
FIG. 1 shows a microsphere capture sandwich immunoassay having a microsphere with two spectrally distinct fluorophores, the target LSD capture antibody and the unique LSD target protein or target antigen bound to the target LSD capture antibody and a reporter molecule.

The Bio-Plex™ protein array system uses multiplexing technology to enable the simultaneous quantitation of up to 100 different analytes. This technology uses polystyrene microspheres internally dyed with differing ratios of 2 spectrally distinct fluorophores. Each fluorophore can have any of 10 possible levels of fluorescent intensity, thereby creating a family of 100 spectrally distinct bead sets. In a preferred embodiment, the dyed microspheres are conjugated with antibodies specific for a target LSD protein or peptide thereof. Although not wanting to be bound by theory, each of the 100 spectrally distinct bead sets can contain a capture antibody specific for a unique LSD target protein. In a multiplexed Bio-Plex™ assay, LSD antibody-conjugated beads are allowed to react with the sample and a secondary LSD antibody, or a detection LSD antibody in a microtiter plate well to form a capture sandwich immunoassay. FIG. 1 shows a drawing of a complete microsphere capture sandwich immunoassay having a polystyrene microsphere (110) with 2 spectrally distinct fluorophores; the target LSD capture antibody (120) bound to the microsphere; a unique LSD target protein or target antigen (130) bound to the target LSD capture antibody; a detection LSD antibody (140); and a detection molecule (e.g. phycoerythrin, "PE" or Biotin) (150). Once the complete microsphere capture sandwich immunoassay has formed in solution, the immunoassay solution is then drawn into the Bio-Plex™ array reader, which illuminates and reads the sample. Although not wanting to be bound by theory, there are many enzyme deficiencies specific for a particular LSD, and some of these enzymes are shown in Table 1.

When a red diode "classification" laser (635 nm) in the Bio-Plex™ array reader illuminates a dyed bead, the bead's fluorescent signature identifies it as a member of one of the 100 possible bead sets. Bio-Plex™ Manager software correlates each bead set to the assay reagent that has been coupled to it (for example, a first LSD capture antibody coupled to bead set #22, and a second LSD capture antibody coupled to bead set #42). In this way the Bio-Plex™ protein array system can distinguish between the different assays combined within a single microtiter well. A green "reporter" laser (532 nm) in the array reader simultaneously excites a third fluorescent dye (phycoerythrin, "PE") bound to the detection LSD antibody in the assay. Although not wanting to be bound by theory, the amount of green fluorescence is proportional to the amount of target analyte captured in the immunoassay. Extrapolating the captured amount of target analyte to a standard curve allows quantitation of each LSD analyte in the sample. The digital signal processing algorithms provide simultaneous real-time data acquisition of classification and reporter signal output from thousands of beads per second, supporting up to 100× 96=9,600 analyte measurements from each 96-well plate.

Example 2

Designing and Producing LSD Target Microspheres. The BioPlex Protein Array System was used as one embodiment to demonstrate the type and nature of the reagents necessary for a LSD multiplex diagnostic assay. Capture antibodies and detection antibodies have been purified that selectively bind epitopes of: saposin, LAMP-1, α-iduronidase, α-glucosidase, β-glucosidase, 2-sulphatase, 4-sulphatase, α-galactosidase, sphingomyelinase, and 3-sulphatase. The full or partial sequences of the following proteins that were used to generate the purified antibodies are as follows: saposin (SeqID No. 1), LAMP-1 (SeqID No. 2), α-iduronidase (SeqID No. 3), α-glucosidase (SeqID No. 4), β-glucosidase (SeqID No. 5), 2-sulphatase (SeqID No. 6), 4-sulphatase (SeqID No. 7), α-galactosidase (SeqID No. 8), sphingomyelinase (SeqID No. 9), 3-sulphatase (SeqID No. 10), and sulphamidase.

Monoclonal Antibodies. Monoclonal antibodies were produced in Balb/C mice using standard immunisation protocols (Harlow et al., 1988). Mice were immunized with recombinant enzyme using established protocols. Plasma cells from these immunized mice were fused with P3.653 myeloma cells (Zola et al., 1982) and the resulting hybridoma cell lines screened for antibodies against the recombinant protein by direct ELISA (Harlow et al., 1988). Monoclonal antibodies were purified from cell culture supernatants by ammonium sulfate precipitation followed by affinity purification on Hitrap™ Protein G affinity column (Pharmacia Biotech, Uppsala, Sweden).

In some embodiments, a monoclonal capture antibody for LAMP-1 was BB6 developed and provided by Sven Carlsson (Carlsson et al., 1989). The monoclonal reporter antibody for α-glucosidase (43D1) was obtained from Pharming, Inc. and has been described (Fransen et al., 1988). The polyclonal reporter antibody for LAMP-1, the rabbit polyclonal reporter antibody for saposin C, the sheep polyclonal capture antibody for α-glucosidase, and the monoclonal capture antibody ("7B2") for saposin C were prepared within the Lysosomal Diseases Research Unit at the WCH in Adelaide, Australia using standard techniques, known in the art, and briefly described below. The availability and production of specific monoclonal and polyclonal antibodies are know to one of ordinary skill in the art. Production of the specific antibodies uses in the current examples are given below:

Polyclonal Antibodies. Sheep polyclonal antibodies were produced against recombinant proteins (e.g. saposin (SeqID No. 1), LAMP-1 (SeqID No. 2), α-iduronidase (SeqID No. 3), α-glucosidase (SeqID No. 4), β-glucosidase (SeqID No. 5), 2-sulphatase SeqID No. 6), 4-sulphatase (SeqID No. 7), α-galactosidase (SeqID No. 8), sphingomyelinase (SeqID No. 9), 3-sulphatase (SeqID No. 10) and sulphamidase). A sheep was injected sub-cutaneously with 2 mg of protein in 1 mL of an emulsion of phosphate buffered saline (pH 7.4) and complete Freunds adjuvant, followed by four booster injections (2 mg each) with incomplete Freunds adjuvant, each three weeks apart. One week after the last injection the sheep was bled out and serum collected. Rabbit polyclonal antibody was produced in the same manner, except 0.2-1.0 mg of protein was used per immunisation. Sheep polyclonal antibody was purified on a 5 mL Hitrap™ Protein G affinity column (Pharmacia Biotech, Uppsala, Sweden) followed by an affinity column prepared from the recombinant protein used for the immunisation. Recombinant protein affinity columns were prepared by coupling 5 mg of the recombinant protein to 2.5 mL of Affi-gel 10 (Bio-Rad, Hercules, Calif., USA) as per manufacturer's instructions.

Briefly, 5 mL of sheep serum was diluted with 5 mL of phosphate buffered saline (pH 7.4) and centrifuged (2200 g, 10 min, 4° C.). The centrifuged serum was passed through a 0.2 μm filter, and then loaded on to the Protein G column at a flow rate of 0.5 mL/min. The column was washed with phosphate buffered saline, pH 7.4 and the antibody eluted with 0.1 mol/L $H_3PO_4$/$NaH_2PO_4$, pH 2.5 and immediately neutralized by adding 1.0 mol/L $Na_2HPO_4$ ($1/10^{th}$ vol). The protein content was estimated by absorbance at 280 nm (absorbance=1.4 for 1.0 g/L of protein). The eluate was diluted four fold and then loaded on to the appropriate recombinant protein affinity column at the same flow rate. The column was washed and eluted as described for the Protein G column.

Coupling Antibodies to Microspheres. The target capture antibodies were coupled to Bio-Rad carboxylated ("COOH") beads as follows: anti-saposin to bead No. 42, anti-LAMP-1 to bead No. 25, anti-α-iduronidase to bead No. 24, anti-α-glucosidase to bead No. 26, anti-β-glucosidase to bead No. 28, anti-2-sulphatase to bead No. 45, anti-4-sulphatase to bead No. 46, anti-α-galactosidase to bead No. 43, anti-sphingomyelinase to bead No. 22, and anti-3-sulphatase to bead No. 44), as indicated in FIG. 9. The coupling of the target capture antibodies to the polystyrene microspheres was performed using the BioRad bead coupling kit (Catalog number 171-406001, BioRad, Hercules, Calif.). The Bio-Plex™ amine coupling kit includes 4 ml bead wash buffer, 85 ml bead activation buffer, 135 ml PBS, pH 7.4, 10 ml blocking buffer, 25 ml storage buffer, 105 ml staining buffer, 40 coupling reaction tubes. The Bio-Plex™ amine coupling kit provides the buffers necessary to covalently couple 6-150 kD proteins to 5.5 μm dyed carboxylated polystyrene beads in under 5 hr. The covalent couple of the target capture antibody to the carboxylated polystyrene bead is achieved via carbodiimide reactions involving the protein primary amino groups and the carboxyl functional groups bound on the surface of polystyrene beads. The covalent attachment is permanent, leaving no unbound protein after cleanup, even after months of storage. The protein-coupled beads can then be used in multiplex protein-protein binding studies or in the development of multiplex assays that can be analyzed with the Bio-Plex™ protein array system. The bead yield per coupling reaction is approximately 80%, or enough protein-coupled beads for two 96-well microtiter plates using 5,000 beads per well.

Once the coupling reaction was completed, the target capture antibody-coupled beads were enumerated and the efficiency of the protein coupling reaction was validated, according to the manufacturer's protocol with modifications. In this procedure, the protein-coupled beads were reacted with a phycoerythrin ("PE")-labeled antibody that binds to the coupled protein, which was then analyzed using the Bio-Plex™ protein array system. This procedure was performed by reacting the beads with a PE-labeled antibody. Alternatively, a reaction using a biotinylated antibody followed by streptavidin-PE may be used. Although not wanting to be bound by theory, the intensity of the fluorescent signal of this reaction is directly proportional to the amount of protein on the surface of the beads. A successful coupling typically yields a mean fluorescent intensity ("MFI") signal that is greater than 2,000. The protein coupling validation procedure provided a rapid relative assessment of the amount of protein coupled to the beads, but could not verify the functionality of the protein.

The detection antibodies that specifically bind epitopes of: saposin; LAMP-1; α-iduronidase; α-glucosidase; β-glucosidase; 2-sulphatase; 4-sulphatase; α-galactosidase; sphingomyelinase; and 3-sulphatase, were biotinylated according to the manufacturer's instructions (Molecular Probes, FluroReporter Biotin-XX protein labelling kit F-2610). There are several published methods known in the art for preparation of biotinylated or phycobiliprotein conjugates with antibodies and other proteins. Generally, the coupling chemistry used to crosslink a phycobiliprotein to another protein includes: (a) treating the antibody or other protein with a succinimidyl ester maleimide derivative at pH 7.5, which converts some lysine residues of the antibody to thiol-reactive maleimides; (b) preparing a thiolated phycobiliprotein by reducing the appropriate SPDP-modified phycobiliprotein with dithiothreitol ("DTT") or with tris-(2-carboxyethyl)phosphine ("TCEP"); (c) mixing the above two dialyzed protein conjugates to yield a stable thioether crosslink; and (d) chromatographically separating the phycobiliprotein conjugates from the unreacted proteins.

Figure 2:
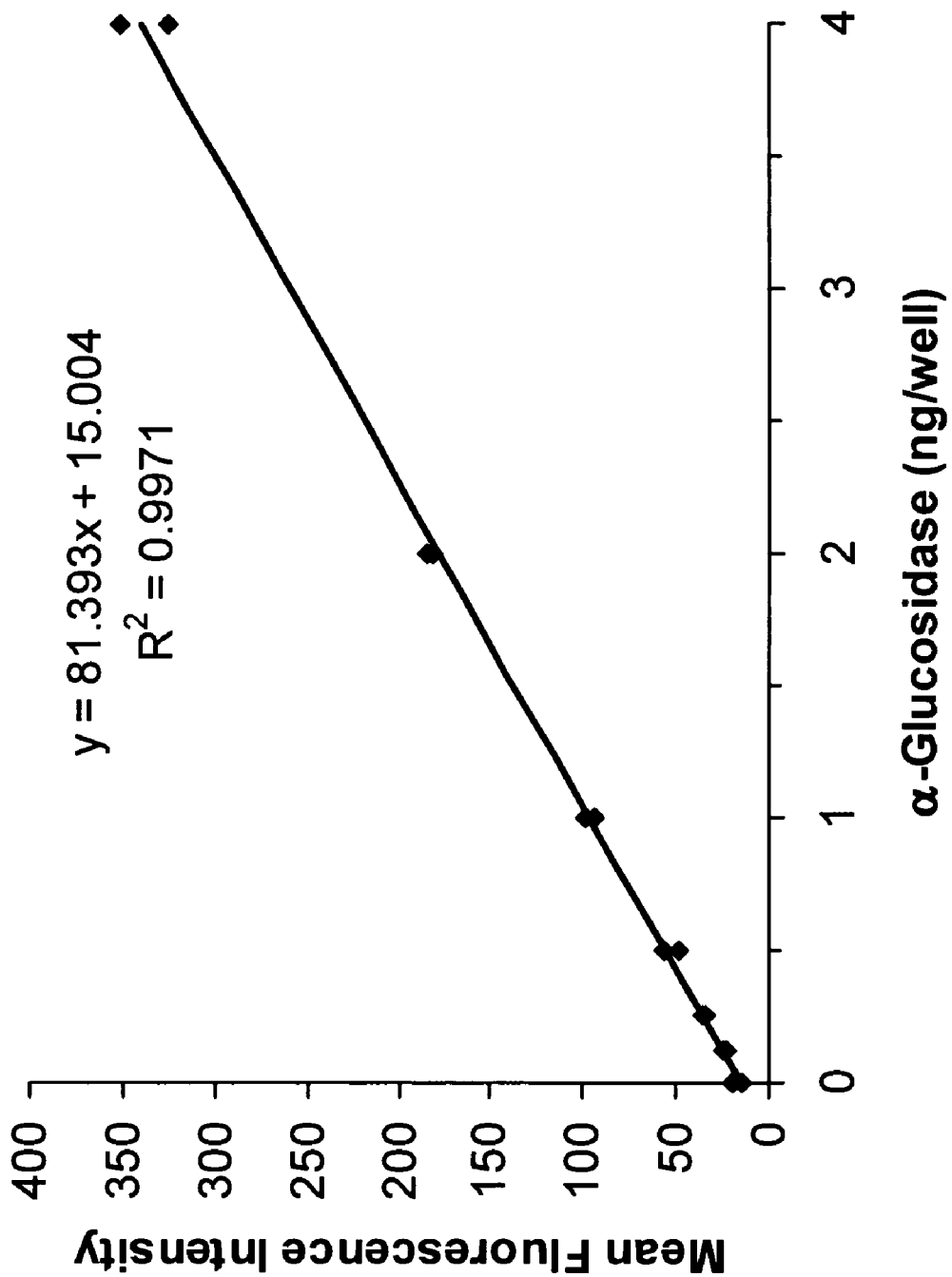
FIG. 2 shows a calibration curve for α-glucosidase in a microsphere based assay.
Figure 3:
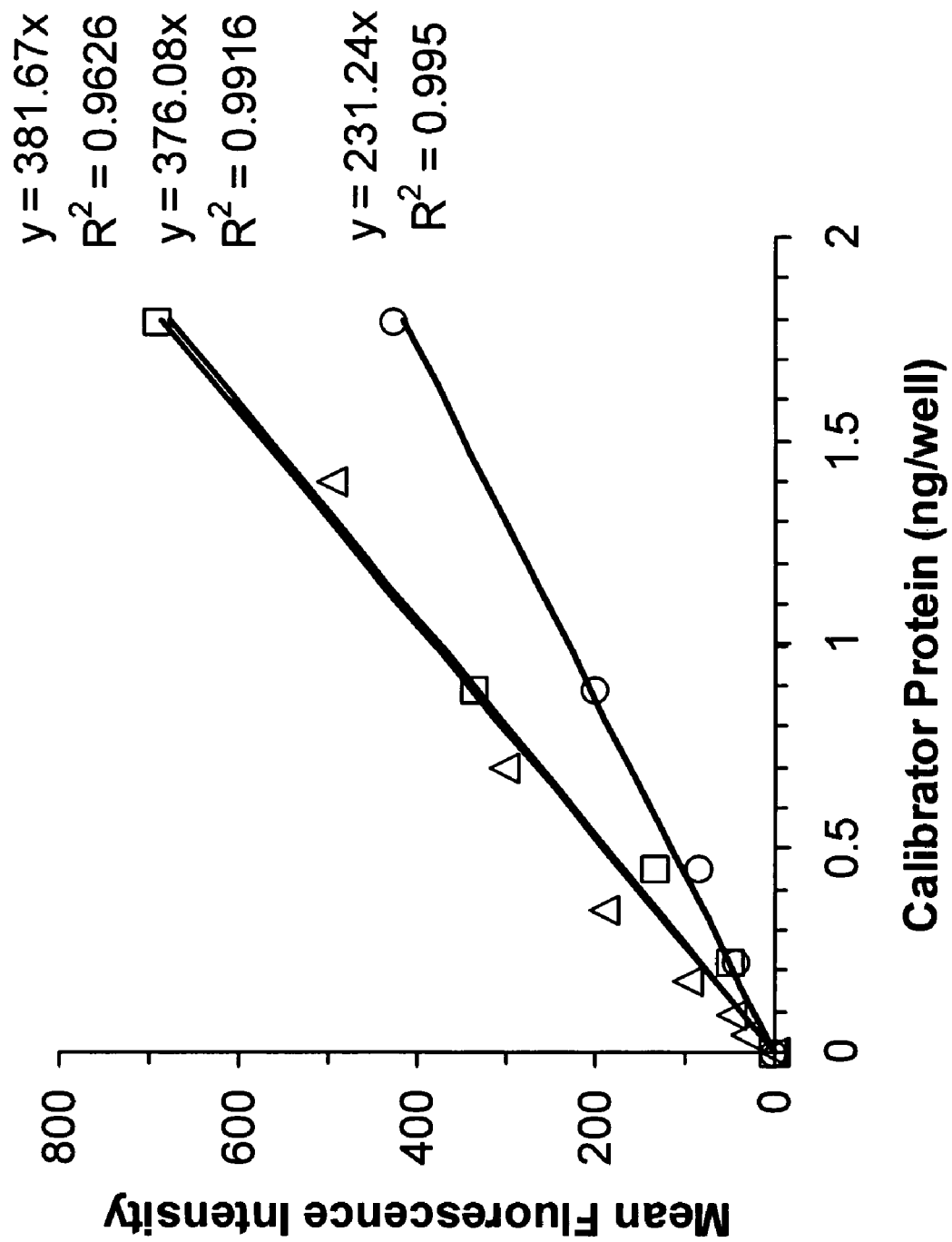
FIG. 3 shows multiplexed calibration curves in a microsphere based assay.

A calibration curve was generated using liquid calibrator proteins in a microsphere based assay using calibrator protein capture antibodies and bead sets #25, #42, #26, #28, #43, #46, #45, #44, and #22 (BioRad, Hercules, Calif., USA). FIG. 2 shows a calibration curve for a single assay for α-glucosidase. The detection capability for the amount of calibrator protein present in each well reaction was linear in the range of 0 to 4 ng/well of the assay. The MFI was the average of the total fluorescence detected for the beads in the defined bead region. Calibration curves were also established, using liquid calibrators, for LAMP-1 (open square), saposin C (open circle), and α-glucosidase (open triangle), as shown in FIG. 3. Increased MFI for the α-glucosidase protein, when compared to FIG. 2, is the result of improvements in the capture antibody labeling of the microspheres and the phycoerythrin reporter labeled antibodies. FIG. 3 also indicates that the detection capability for a multiplex assay of three calibrators was linear from 0 to 2 ng/well of the assay.

Figure 4:
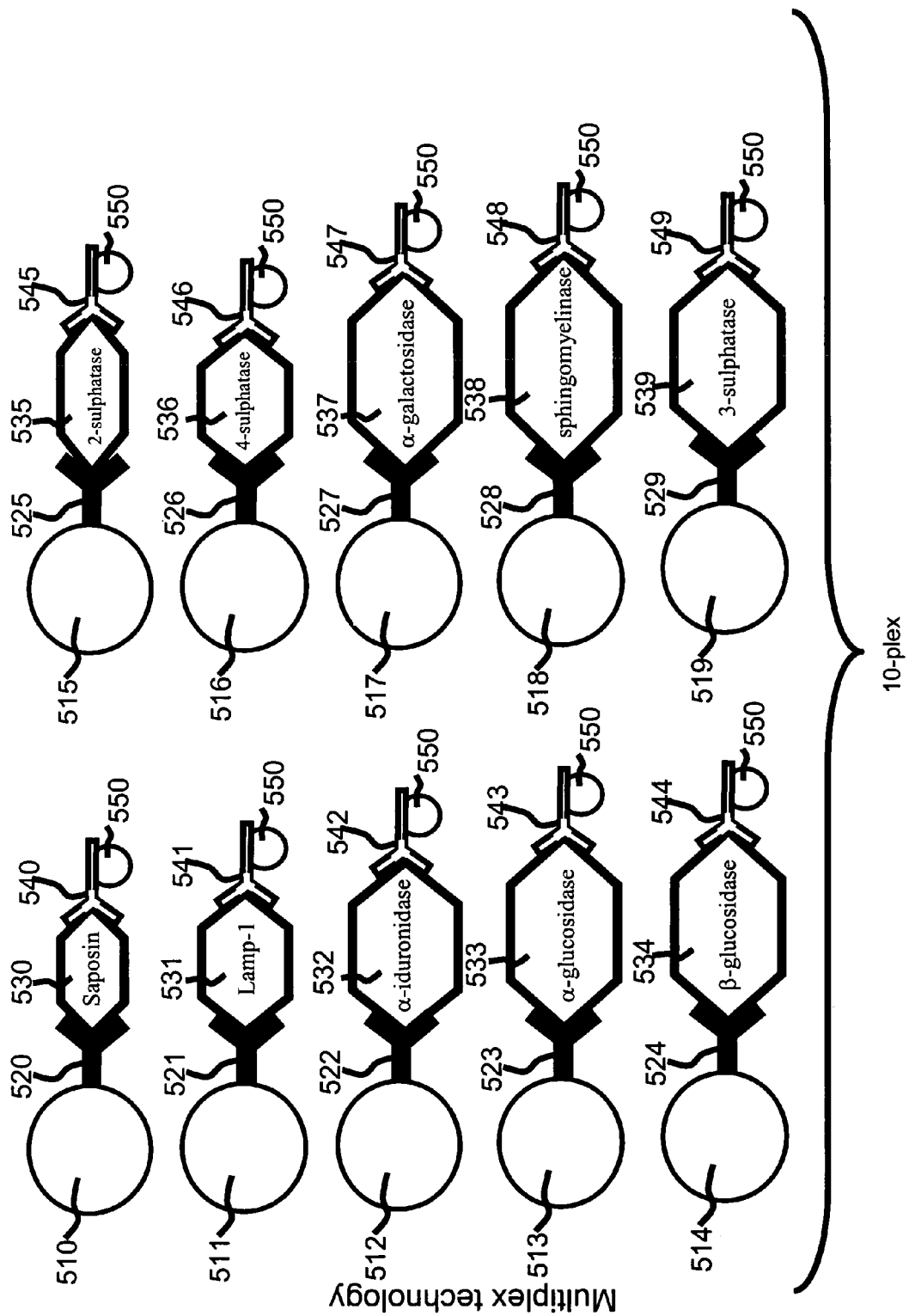
FIG. 4 shows the multiplex technology having at least a 10-plex for LSD's.

As a general illustration, FIG. 4 shows a drawing of a microsphere collection of capture sandwich immunoassays for the 10-plex having: 10 spectrally distinct polystyrene microsphere (510-519); 10 target LSD capture antibody (520-529) bound to the microsphere; 10 unique LSD target proteins or target antigens and representing: saposin, LAMP-1, α-iduronidase, α-glucosidase, β-glucosidase, 2-sulphatase, 4-sulphatase, α-galactosidase, sphingomyelinase, and 3-sulphatase (530-539) bound to the corresponding target LSD capture antibody; 10 unique detection LSD antibody (540-549); and a detection molecule (550).

Figure 5:
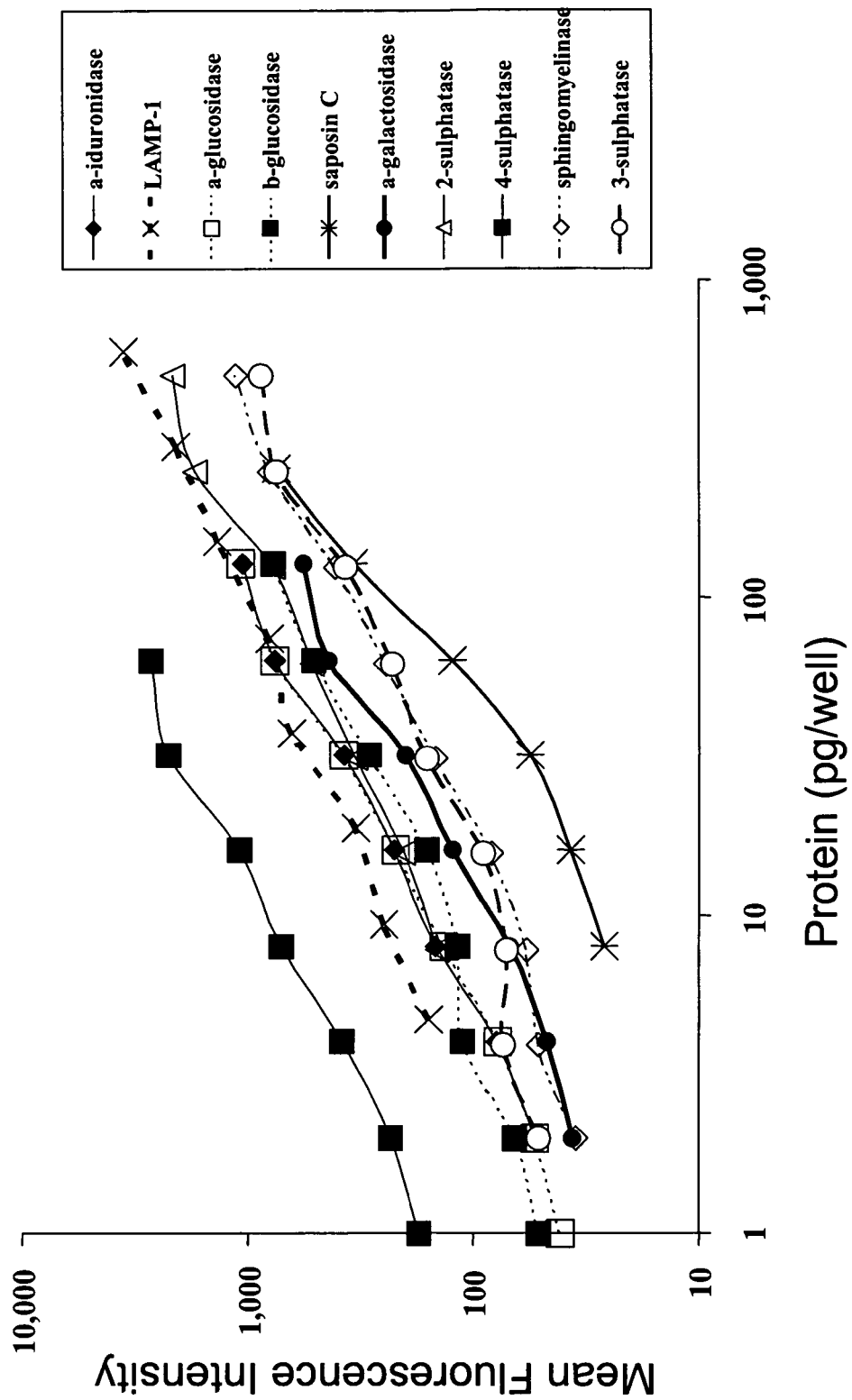
FIG. 5 shows calibration curves for a 10-plex immune quantification of lysosomal proteins.
Figure 6:
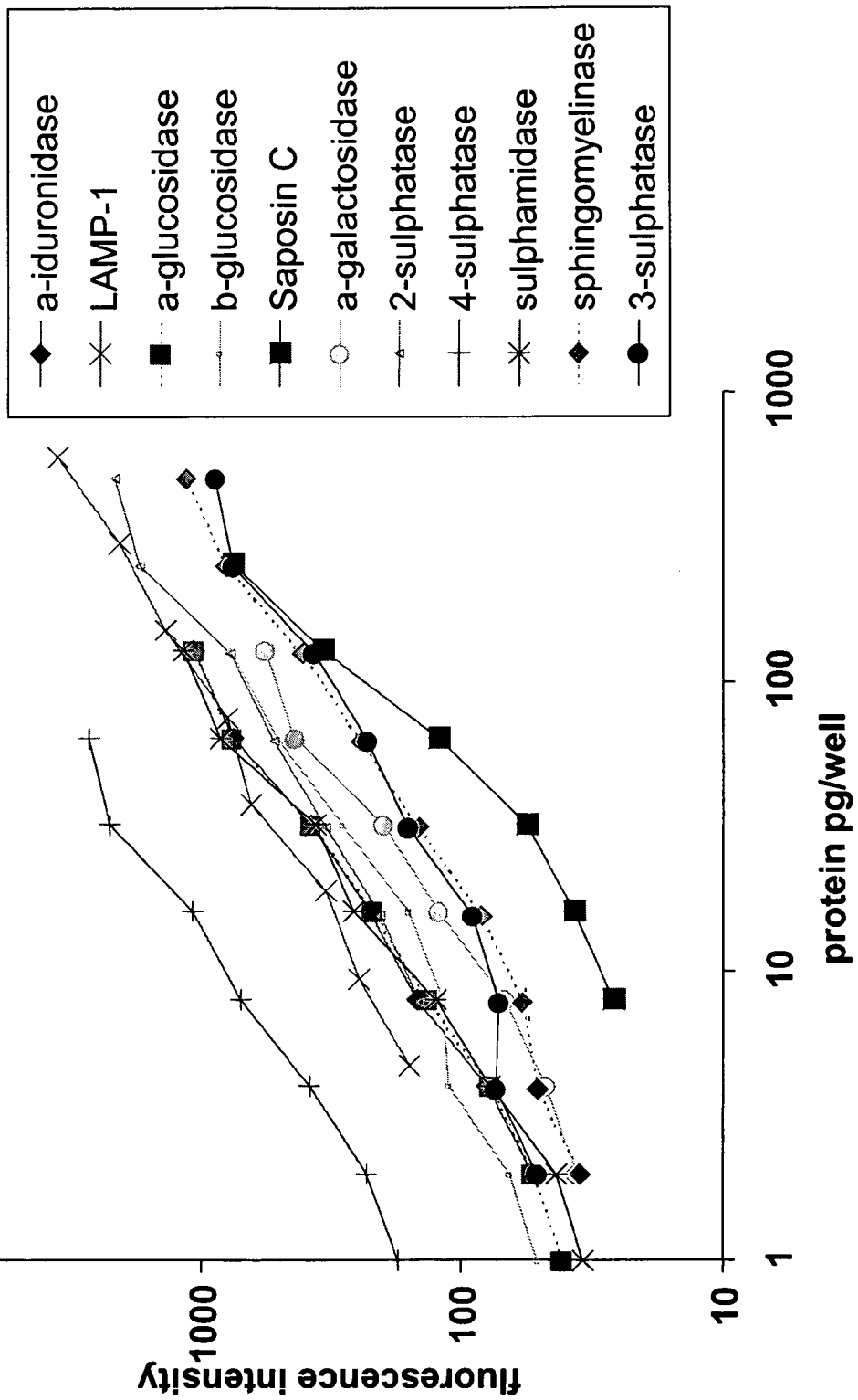
FIG. 6 shows calibration curves for a 11-plex immune quantification of lysosomal proteins.
Figure 11:
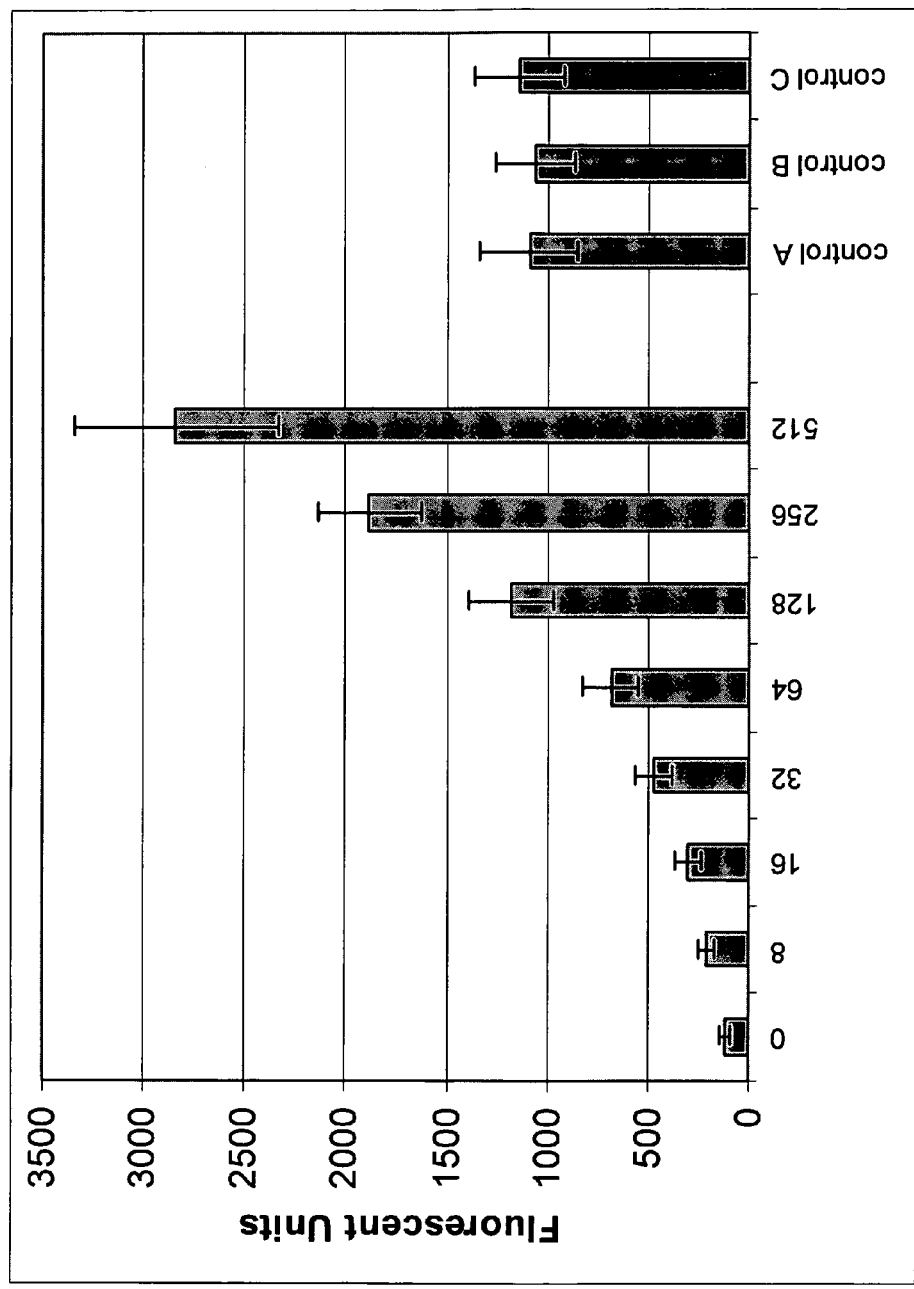
FIG. 11 shows the LAMP Protein Standard and Adult Controls in Fluorescent Units.
Figure 12:
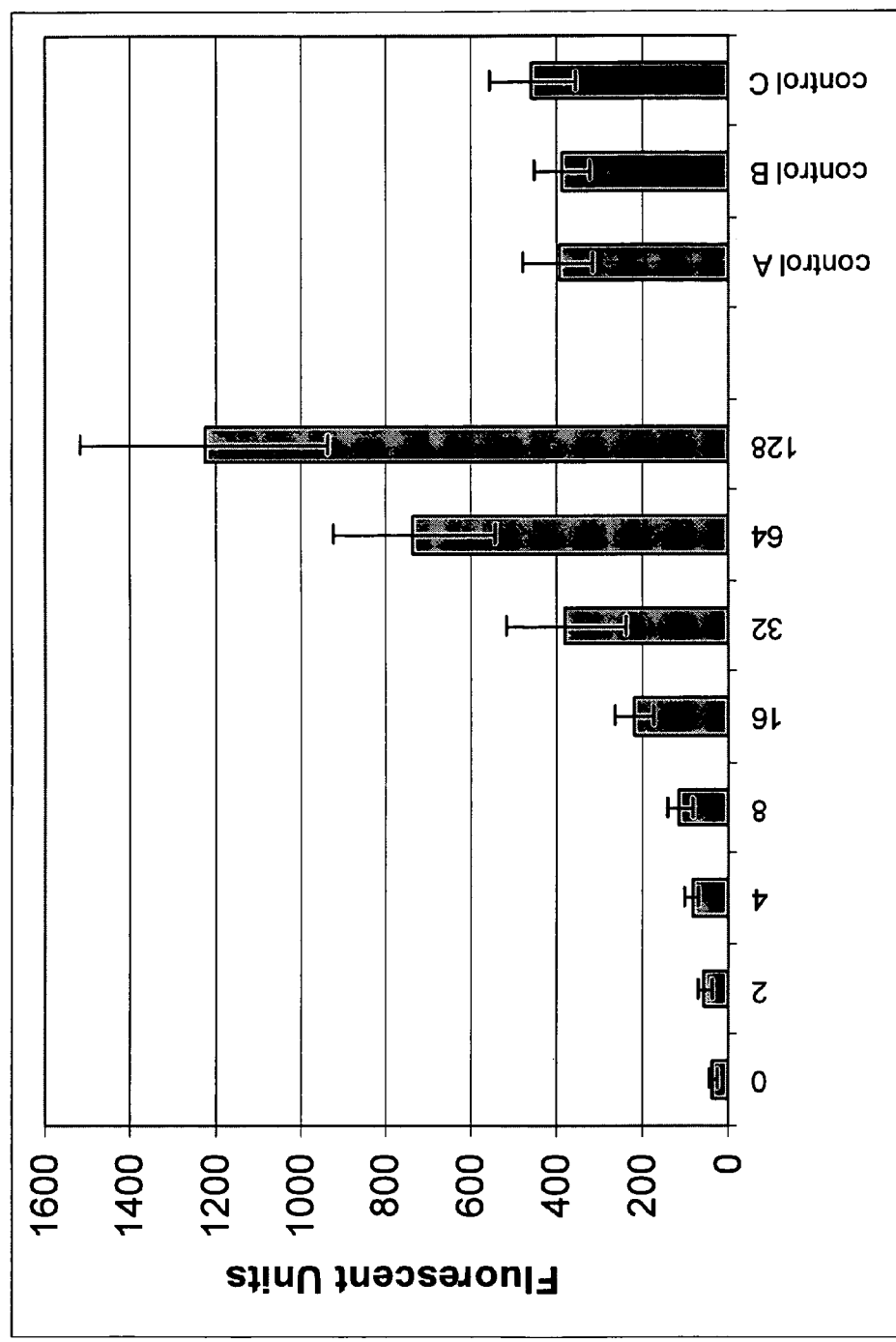
FIG. 12 shows the GAA Protein Standard and Adult Controls in Fluorescent Units.
Figure 13:
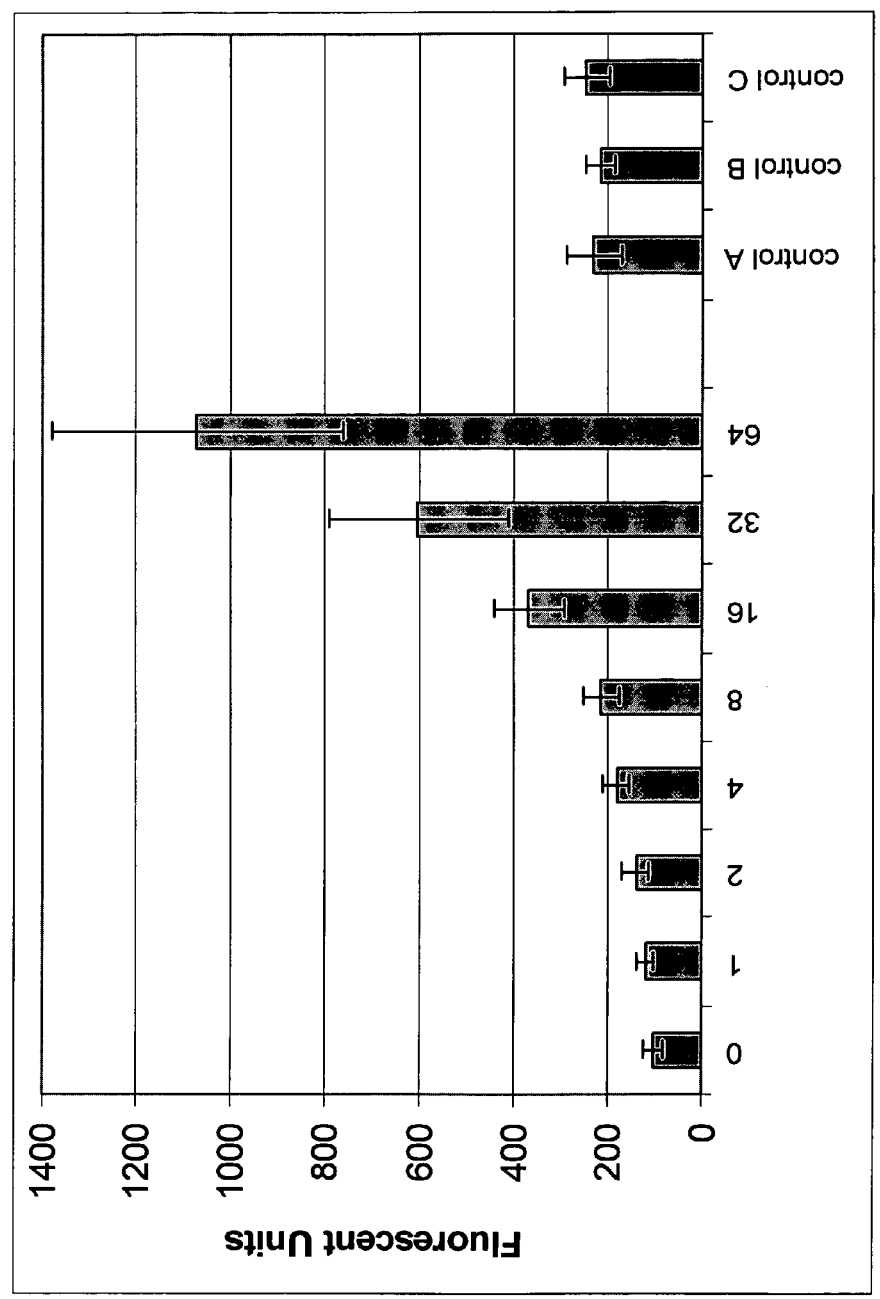
FIG. 13 shows the beta-Glucosidease Protein Standard and Adult Controls in Fluorescent Units.
Figure 14:
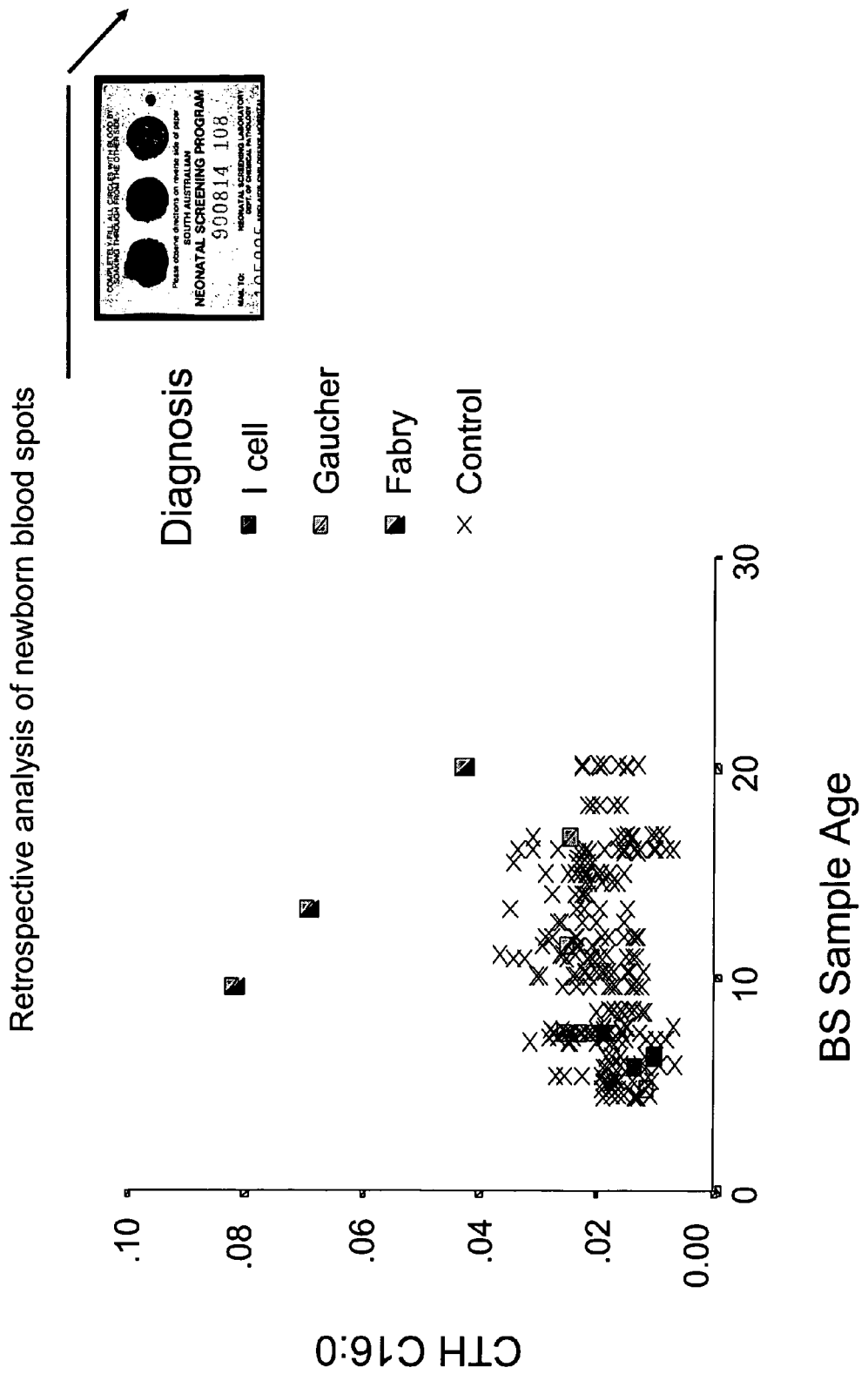
FIG. 14 shows retrospective analysis of CTH C 16:0 in newborn blood spots.
Figure 15:
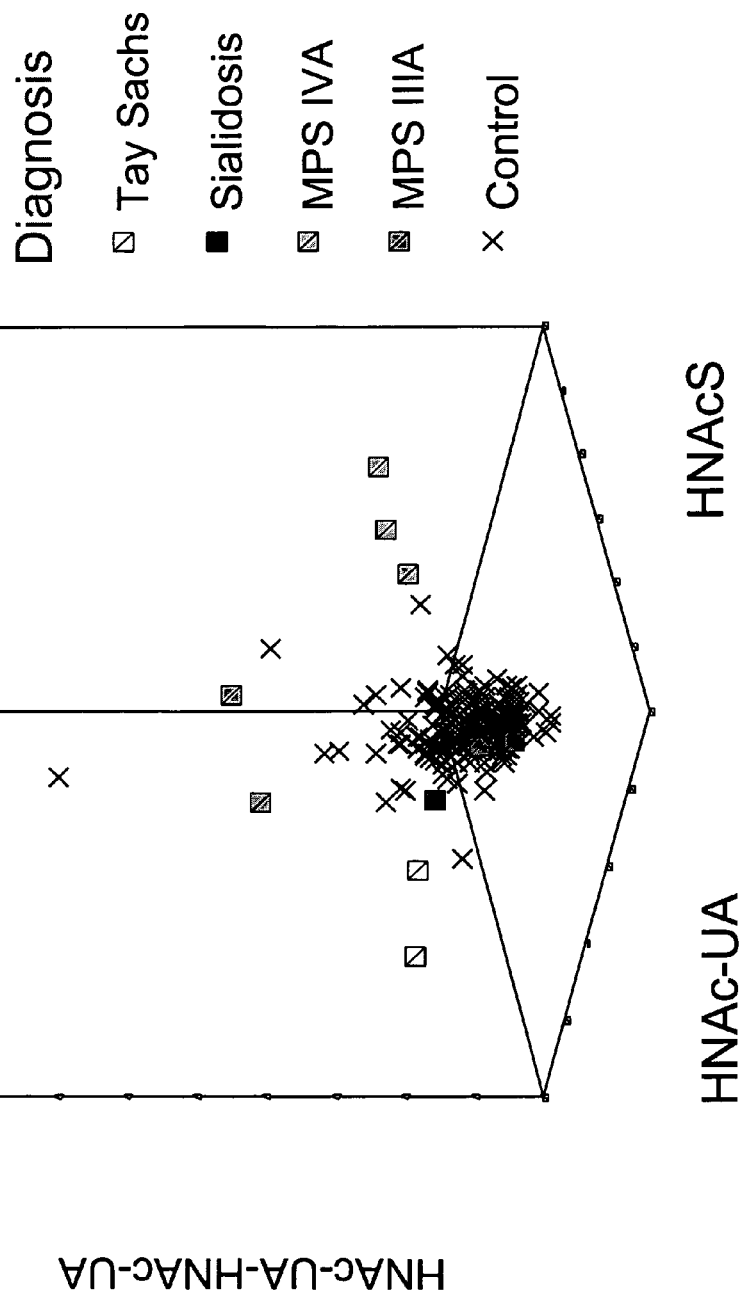
FIG. 15 shows retrospective analysis of HNAc-UA-HNAc-UA in newborn blood spots.
Figure 16:
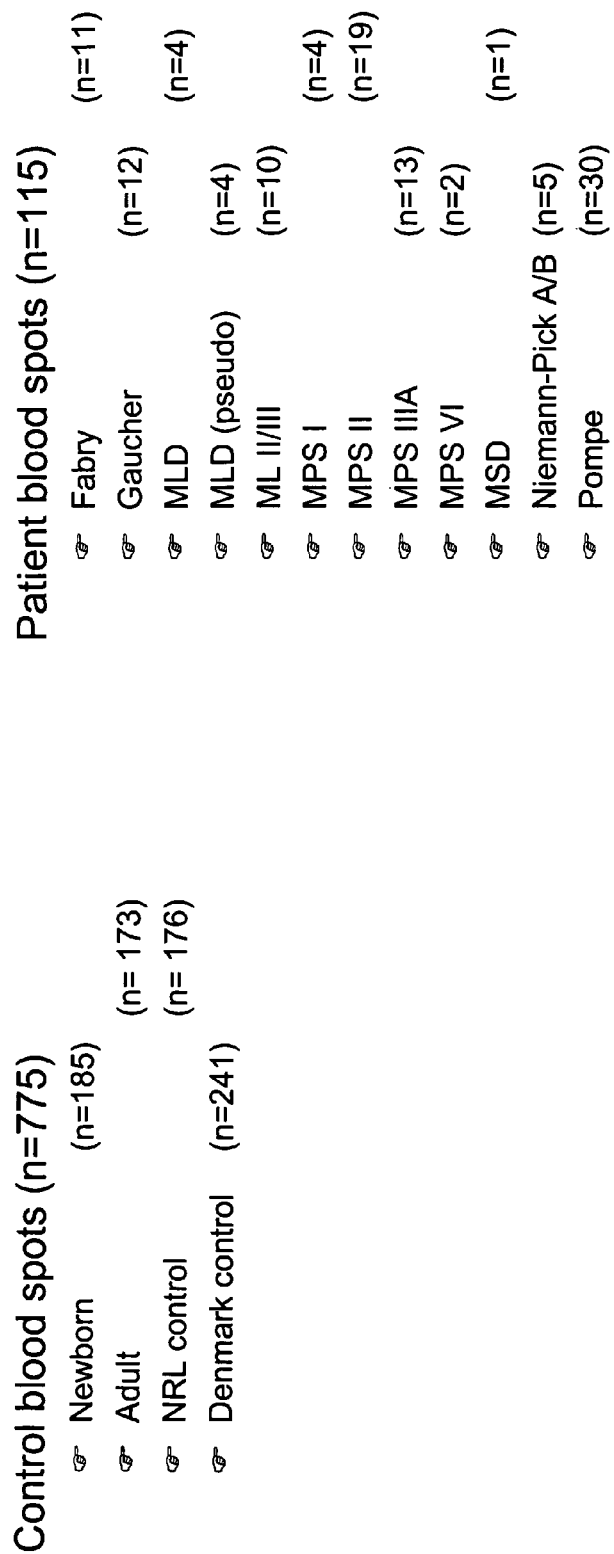
FIG. 16 shows Validation of the Multiplex Newborn Screening Assay.

Development of Ten-Plex and Eleven-Plex Assays. All bead assays were performed in 96-well filtration plates (Millipore MAB VNS1250), sealed and protected from light. All standards were performed in duplicate. Standard solutions containing saposin C, LAMP-1, α-iduronidase, α-glucosidase, β-glucosidase, 2-sulphatase, 4-sulphatase, α-galactosidase, sphingomyelinase, and 3-sulphatase protein (50 µl) were added in serial 2-fold dilutions in assay buffer, as indicated. Standards were generated by using the recombinant form of each specific target protein. Biotinylated antibodies (50 µl) were added to each well, wherein the final concentration of each antibody was 16 ng/well in assay buffer. Antibody-coated beads (5,000/well) for each individual assay were mixed in filtered (0.2 µm) PBS containing 0.5% BSA (Sigma A-9647), 0.05% γ-globulin (Sigma G-7516) and 0.05% Tween 20, pH 7.2 (assay buffer), placed into pre-wetted filtration plates and the supernatant removed by vacuum. Diluted pre-mixed standards were added to the beads followed by the 10 pre-mixed biotinylated reporter antibodies. The plates were incubated for one-hour at room temperature with shaking and then placed at 4° C. overnight. After a further one-hour incubation at room temperature with shaking, the plates were washed three-times with filtered (0.2 µm) PBS containing 0.05% Tween 20, pH 7.2 (wash buffer) under vacuum. Streptavidin conjugated to phycoerythrin (Molecular Probes S-866) was diluted in assay buffer (1.2 µg/mL) and added to the wells (125 µl/well); the plates were then incubated at room temperature with shaking for 10 minutes. The plates were then read on the Bio-Plex suspension array system (Bio-Rad) using version 3.0 software and counting 100 beads/region. FIG. 5 shows the resulting calibration curves for saposin C (asterisk), LAMP-1 (X-mark), α-iduronidase (solid diamond), α-gulucosidase (open square), β-gulucosidase (solid square), 2-sulphatase (open triangle), 4-sulphatase (solid square), α-galactosidase (solid circle), sphingomyelinase (open diamond), and 3-sulphatase (open circle) of the 10-plex assay. FIG. 6 shows an 11-plex assay with an added sulphamidase (asterisk).

The control ranges for protein markers in adult, NRL controls, Denmark and newborn samples are shown in FIGS. 19-29 for each of the specific markers (sulphamidase; acid sphingomyelinase; alpha-iduronidase; LAMP-1; alpha-glucosidase; beta-glucosidase; Saposin C; alpha-galactosidase; arylsulphatase A; iduronate-2-sulphatase; and 4-sulphatase). As shown in FIGS. 19-29, the box length is the interquartile range that covers 25th to 75th percentile, the outliers are represented by (circles) each of these cases represent values between 1.5 and 3 box lengths from the upper or lower edge of the box, and the extreme outlier (stars) are cases with values more than 3 box lengths from the upper or lower edge of the box.

The ranges for protein markers in adult controls, newborn controls, Fabry, Gaucher, MLD, MPS I, MPS II, MPSIIA MPS VI, NP a/b and Pompe samples are shown in FIGS. 31-40 for each of the specific markers (sulphamidase; acid sphingomyelinase; alpha-iduronidase; LAMP-1; alpha-glucosidase; beta-glucosidase; Saposin C; alpha-galactosidase; arylsulphatase A; iduronate-2-sulphatase; and 4-sulphatase). As shown in FIGS. 31-40, the box length is the interquartile range that covers 25th to 75th percentile, the outliers are represented by (circles) each of these cases represent values between 1.5 and 3 box lengths from the upper or lower edge of the box, and the extreme outlier (stars) are cases with values more than 3 box lengths from the upper or lower edge of the box.

FIG. 44 shows a table having the percent identification of LSD using single proteins that allowed many of the LSD's to be 100% identified, and Gaucher and Pompe were not identified 100%. FIG. 50 showed a table having the percent identification of LSD using ratios as having all but Gaucher identified as 100%.

A retrospective analysis of newborn samples from Guthrie cards was also conducted. FIGS. 51-55 show the retrospective analysis of: alpha-galactosidase; alpha-glucosidase; beta-glucosidase; sulphamidase; and iduronate-2-sulphatase. As shown in FIGS. 51-55, the box length is the interquartile range that covers 25th to 75th percentile, the outliers are represented by (circles) each of these cases represent values between 1.5 and 3 box lengths from the upper or lower edge of the box, and the extreme outlier (stars) are cases with values more than 3 box lengths from the upper or lower edge of the box. FIG. 62 shows that Fabry, ML II/III, MPS II, MPS IIIA and Pompe were identified from retrospective LSD affected newborns at 100%, and Gaucher was identified in retrospective LSD affected newborns at 80%. The other disorders were not identified in this retrospective analysis.

Example 3

A defect in exo-degradative pathways provides insight into endo-degradation of heparan and dermatan sulfates. Maria Fuller, Ally Chau, Rachael C. Nowak, John J. Hopwood and Peter J. Meikle contributed to the invention of Example 3. Within cells, dermatan sulfate and heparan sulfate are degraded in two steps. The initial endohydrolysis of these polysaccharides is followed by the sequential action of lysosomal exoenzymes to reduce the resulting oligosaccharides to monosaccharides and inorganic sulfate. Mucopolysaccharidosis types II is a lysosomal storage disorder caused by a deficiency of the exoenzyme iduronate-2-sulfatase. Consequently, partially degraded fragments of dermatan sulfate and heparan sulfate, have been shown to accumulate in the lysosomes of affected cells and are excreted in the urine. Di- to hexadecasaccharides, isolated from the urine of a mucopolysaccharidosis type II patient using anion exchange and gel filtration chromatography, were identified using electrospray ionization-tandem mass spectrometry. These oligosaccharides were shown to have non-reducing terminal iduronate 2-sulfate residues by digestion with recombinant iduronate 2-sulfatase. A pattern of growing oligosaccharide chains composed of alternating uronic acid and N-acetylhexosamine residues was identified and suggested to originate from dermatan sulfate. A series of oligosaccharides consisting of hexosamine/N-acetylhexosamine alternating with uronic acid residues were also identified and based on the presence of unacetylated hexosamine, these oligosaccharides are proposed to derive from heparan sulfate. The presence of both odd and even length oligosaccharides suggests both endo-β-glucuronidase and endo-N-acetylhexosaminidase activities toward both glycosaminoglycans. Furthermore, the putative oligosaccharide structures identified indicate that heparanase activities are directed towards regions of both low and high sulfation, whilst the N-acetylhexosaminidase activity acted only in regions of low sulfation.

The sulfated glycosaminoglycans heparan sulfate (HS) and dermatan sulfate (DS) are present in a wide variety of cell types where they play an intricate role in the extracellular matrix. HS has repeating disaccharide units consisting of uronic acid (UA) alternating with α-linked (1,4) glucosamine (GlcN) residues. Biosynthesis of HS occurs in the Golgi. Following the synthesis of the base polymer consisting of the disaccharide repeat (GlcA 1-4 GlcNAc), a series of enzymatic reactions occurs, deacetylating the GlcNAc, epimerising the glucuronic acid (GlcA) to iduronic acid (IdoA) and adding sulfate groups to both O and N positions on IdoA and GlcN. Consequently, the UA residue may be β-linked (1,4) D-GlcA, or α-linked (1,4) L-IdoA, unsulfated or with O-sulfation of the C2-hydroxyl. The amino group of GlcN may be N-sulfated, N-acetylated or occasionally unsubstituted. The GlcN may also be sulfated on the C6-hydroxyl and sometimes on the C3-hydroxyl. The proportion of GlcA and IdoA varies considerably, not only between different species of HS but also within a particular HS chain. Likewise, the degree and type of sulfation is not stoichiometric (3). The modification reactions that are responsible for the structural diversity are not complete, producing a final HS molecule with a domain structure (4). HS chains typically contain regions rich in GlcA and N-acetylated GlcN (GlcNAc) disaccharides with no sulfation (NA domains), contiguous variable length sequences containing IdoA and GlcNS derivatives with high sulfation (NS domains), and bridging these domains are mixed sequences in which GlcNAc disaccharides and GlcNS disaccharides alternate (NA/NS domains) (5).

DS is composed of repeating disaccharide units consisting of UA alternating with β-linked (1,4) D-N-acetylgalactosamine (GalNAc) residues that may be sulfated on the C4- and/or C6-position. Some DS chains have predominantly (1,3) α-linked IdoA residues with some C2-sulfation, while others have primarily (1,3) β-linked GlcA. Similar to HS, DS forms block structures of lowly sulfated GlcA-GalNAc disaccharides alternating with blocks of highly sulfated IdoA-GalNAc disaccharides.

The catabolism of HS and DS begins with endohydrolysis of the polysaccharide chains to oligosaccharides. Two classes of human endoenzymes have been reported that cleave at specific sites within the DS and HS polysaccharides. Hyaluronidases (endo-β-N-acetylhexosaminidases) are a family of enzymes that degrade hyaluronan, as well as chondroitin sulfate and DS. Hyaluronidases cleave internal β-linked (1,4) glycosidic bonds between GalNAc and GlcA in DS (7). Levels of hyaluronidase are elevated in a number of cancers but the identity of the type of hyaluronidase expressed in most cancer tissue and cells is still unknown (8). Heparanase (endo-β-glucuronidase) cleaves at glucuronosyl bonds within HS resulting in smaller saccharide chains. Heparanase activity has been shown to be associated with cell invasion, angiogenesis, inflammation and tissue remodelling through a number of cell-matrix interactions. The action of heparanase on cell surface and extracellular matrix HS proteoglycans is thought to be a highly regulated process involving the binding and internalisation of heparanse to specific cell surface proteoglycans (syndecans), thereby limiting the extracellular accumulation and action of this endoglycosidase. Endosulfatase action on heparin has also been reported and it is likely that similar activity will be shown to the sulfated domains of HS.

Following partial catabolism by endoenzymes, HS and DS are degraded from their non-reducing termini by the sequential action of highly specific lysosomal exoenzymes. At least 10 lysosomal exoenzymes act to reduce these oligosaccharides to monosaccharides and inorganic sulfate to enable exit out of the lysosome. A deficiency in any one of these exoenzyme activities may result in lysosomal storage of the GAG substrates with the resulting clinical manifestation of the mucopolysaccharidoses (MPS). MPS II results from a deficiency of iduronate-2-sulfatase (I2S; EC 3.1.6.13), which hydrolyzes the C2-sulfate ester bond of non-reducing terminal α-L-iduronic acid residues in HS and DS. In the absence of I2S activity the catabolism of HS and DS is blocked. Consequently, partially degraded fragments of HS and DS accumulated in the lysosomes of affected cells and are excreted in the urine. These oligosaccharide fragments are presumably produced by endohydrolase activities, followed by exohydrolase activities that terminate at the substrate for I2S. Structural characterisation of these oligosaccharides can therefore provide insight into the process of endodigestion of HS and DS and detail of the substrate specificities of the enzymes involved. To this end, we have identified a series of oligosaccharides from MPS II patient urine that provide evidence for novel endohydrolase activities and specificities.

Experimental Procedures and Materials for Example 3.

Recombinant human IDUA and recombinant human I2S were each prepared from CHO-K1 expression systems. MPS II patient urine and control urine was supplied with consent.

Isolation of urinary GAG. Urine samples from an MPS II patient and an age-matched control (500 ml) were clarified by centrifugation and passed over a 30 ml column of DEAE-Sephacel previously equilibrated with 0.1 M NaCOOCH$_3$ buffer, pH 5. The column was washed with 10 column volumes of the equilibration buffer and urinary GAG eluted in the same buffer containing 1.2 M NaCl. Fractions were assayed for UA and the GAG-containing fractions (20 ml) were pooled, lyophilized and reconstituted in 4 ml of H$_2$O.

The pooled GAG fraction was then size-fractionated on a Bio-Gel P4 column (170 cm×1.5 cm) in 0.5 M NH$_4$COO. Fractions (4 ml) were collected and assayed for UA.

Derivatization of oligosaccharides. Samples from Bio-Gel P4 column fractions were lyophilized prior to derivatization. Samples were resuspended in 100 µL 250 mM 1-phenyl-3-methyl-5-pyrazolone, 400 mM NH$_4$OH, heated at 70° C. for 90 min and then acidified with a 2-fold molar excess of HCOOH. Samples were made up to 500 µl with H$_2$O and then extracted with an equal volume of CHCl$_3$ to remove excess 1-phenyl-3-methyl-5-pyrazolone and centrifuged at 13,000×g for 5 min. Chloroform extraction was repeated a further 2 times and the aqueous layer was lyophilised and the derivatized oligosaccharides resuspended in 500 µL of an aqueous solution of 50% (v/v) CH$_3$CN/0.025% (v/v) HCOOH prior to analysis by mass spectrometry. Derivatization of samples following enzyme digestion was performed in the same way except that the aqueous phase from the first chloroform extraction was treated as follows: copolymeric solid phase extraction cartridges (50 mg, C18 and aminopropyl) (United Chemical Technologies, Bristol, Pa., USA) were primed with methanol (1 mL) then water (1 mL), after which the sample was applied and allowed to enter the solid phase completely. Samples were desalted with three consecutive 1 mL water washes, dried on a Supelco, Visiprep24 vacuum manifold (Sigma-Aldrich, St. Louis, Mo., USA) and the remaining 1-phenyl-3-methyl-5-pyrazolone was removed with two 1 mL chloroform washes. The columns were again dried, and derivatized oligosaccharides were eluted in an aqueous solution of 50% (v/v) CH$_3$CN/NH$_4$OH pH 11.5, lyophilized and resuspended in 50% (v/v) CH$_3$CN/0.025% (v/v) HCOOH.

Enzymatic cleavage. Column fractions containing 10 µg of UA were lyophilized prior to digestion with recombinant I2S and IDUA. Enzymatic cleavage was performed at 37° C. for 16 hr in 50 µL of 50 mM NaCOOCH$_3$ buffer (pH 4.5) supplemented with 0.5 mg/ml BSA and 20 µg recombinant enzyme (IDUA and/or I2S). Following digestion, the oligosaccharides were derivatized as described above and analyzed by ESI-MS in negative ion mode.

Mass spectrometry. Oligosaccharide analysis was performed by ESI-MS/MS using a PE Sciex API 3000 triple-quadrupole mass spectrometer with an turboionspray source and Analyst 1.1 data system. Samples were either directly infused using a Harvard Apparatus pump at 10 µL/min or injected with a Gilson 233 autosampler at 80 µL/min using a carrying solvent of 50% (v/v) CH$_3$CN/0.025% (v/v) HCOOH in H$_2$O. Oligosaccharides were identified based on mass to charge (m/z) ratios by ESI-MS and further characterized using collision induced dissociation-MS/MS in the negative ion mode.

Isolation of oligosaccharides in MPS II urine. A combination of anion exchange and gel filtration was used to isolate GAG-derived oligosaccharides from control and MPS II urine. From a volume of 500 mL of MPS II urine, 45 mg of UA equivalents were recovered from the DEAE column and of this material 40% eluted in the fractionation range of the Bio-Gel P4 column (<hexadecasaccharide). In comparison, from 500 mL of urine from a control individual, only 0.2 mg of UA equivalents were recovered and 100% of this was excluded from the Bio-Gel P4 fractionation range (>hexadecasaccharide). Urinary oligosaccharides, from the MPS II patient, eluting between 96 and 225 mL (FIG. 66) were further characterized by mass spectrometry.

Mass spectrometry of oligosaccharides. Electrospray ionisation-mass spectrometry (ESI-MS) was performed in negative ion mode on each eluate fraction from the Bio-Gel P4 column. For each oligosaccharide structure, multiple sulfated species could be identified. These oligosaccharides showed characteristic multiply charged ions produced by proton abstraction and as such were identified as [M-H]$^{-1}$ up to [M-8H]$^{-8}$ ions. FIG. 67 shows representative spectra for oligosaccharides ranging from tetrasaccharide to tetradecasaccharides. Electrospray ionisation-tandem mass spectrometry (ESI-MS/MS) was also used for further characterisation of these oligosaccharides. Precursor ion scan of m/z 173, corresponding to an ionised 1-phenyl-3-methyl-5-pyrazolone (PMP) fragment was used to support the assignments made from the ESI-MS scans. Strong signals were observed for oligosaccharide ions in higher charged states (>[M-3H]$^{-3}$), whereas signals from the [M-2H]$^{-2}$ were weak or not detectable (data not shown). Collisionally activated dissociation-tandem mass spectrometry (CAD-MS/MS) was performed on all major oligosaccharide signals and used to confirm the assignments made from the ESI-MS spectra and to identify the residue at the reducing terminus. Oligosaccharides containing N-acetylhexosamine (HNAc) at the reducing terminus gave a product ion at m/z 256 and those with a UA at the reducing end gave a product ion of m/z 331. A representative product ion spectra of a tetrasaccharide (UA-HN-UA-HNAc 4S) with a characteristic product ion m/z 256 is shown in FIG. 68a, and FIG. 68b shows the product ion spectra from a pentasaccharide (UA-HN-UA-HNAc-UA 4S) with a characteristic product ion of m/z 331. Product ion analysis was performed on all major signals in the ESI-MS and in most instances enabled the identification of the reducing terminal sugar as either UA or HNAc.

The mass spectrometric analysis of the oligosaccharides eluted from the Bio-Gel P4 column enabled the identification of 25 different oligosaccharide species ranging in size from di- to hexadecasaccharide with various numbers of sulfates. Tables 1 and 2 display a summary of the oligosaccharides present in the MPS II patient urine that were classified into series' based on their proposed structures. Two series of oligosaccharides containing UA and HNAc disaccharide repeat units were identified with 1-2 sulfates per disaccharide. The first series, with an even number of saccharides, had a UA residue on the non-reducing end and a HNAc on the reducing end (Table 1, series 1). The second series consisted of an odd number or residues ranging from tri- to heptasaccharide (Table 1, series 2) with UA at the reducing terminus.

Four series of oligosaccharides containing UA, HN and HNAc were identified with different levels of sulfation (Table 2). Series 1-3 consist of an odd number of residues with UA at the reducing terminus, and series 4 contains an even number of residues with HNAc at the reducing terminus. The oligosaccharides in series 1 are composed of one HN with either zero, one or two HNAc. Series 2 contains oligosaccharides with two HN and up to five HNAc. The oligosaccharide in series 3 contains three HN residues and a single HNAc. Series 4 lists oligosaccharides with an even number of residues containing one HN and up to four HNAc residues.

Enzymatic characterisation of the non-reducing end. For oligosaccharides present in sufficient quantities the non-reducing end UA was identified as iduronate-2-sulfate (Ido2S) by enzymatic cleavage with recombinant I2S and IDUA. FIG. 69 shows ESI-MS of pooled hexa- and heptasaccharide fractions isolated from MPS II urine, before and after I2S and IDUA treatment. The hexasaccharide identified by m/z ratios with the putative structure [UA-HNAc]$_3$ with 1 to 4 sulfates was shown to lose 176 and 80 amu, representing UA and S respectively, following incubation with recombinant I2S and IDUA. As with the hexasaccharide, a heptasaccharide with the proposed structure (UA-HN)$_2$-UA-HNAc-UA with 3 to 6

S, also showed losses of 176 and 80 amu following digestion with recombinant IDUA and I2S (FIG. 69). A peak with m/z of 523.3 corresponding to IdoA hydrolysed from the oligosaccharides was also identified in the digested sample (FIG. 69b). Treatment of the oligosaccharides with only recombinant IDUA resulted in no change to the spectra, while treatment with I2S resulted in the disappearance of each of the oligosaccharides in the highest sulfation form (spectra not shown).

Di- to hexa-decasaccharides that would appear to originate from endohydrolase activities on HS and DS, and are therefore the result of incomplete catabolism of HS and DS, were isolated from the urine of an MPS II patient. Mass spectrometry has enabled structural characterisation of these oligosaccharides using a combination of ESI-MS and CAD-MS/MS. CAD-MS/MS was performed on all major oligosaccharide signals and used to confirm the assignments made from the ESI-MS spectra and to identify the residue at the reducing terminus. Enzyme treatment with recombinant I2S and IDUA identified the non-reducing residue as IdoA2S, the substrate for the enzyme deficiency in MPS II.

ESI-MS identified oligosaccharides that have a different number of residues but very similar molecular weights, which occurs as a result of the similarity between the mass of HN (161 Da) and 2 S (160 Da). For example, the octasaccharide ([UA-HN]$_3$-UA-HNAc (4S)) has a molecular weight of 2059.4 whereas the heptasaccharide ([UA-HN]$_2$-UA-HNAc-UA (6S)) has a molecular weight of 2058.4 and when the $[M-4H]^{-4}$ ions are compared the difference is m/z 513.9 compared with m/z 513.6, respectively. The mass accuracy of the instrument used in this study could not positively discriminate these structures. However, identification of the reducing terminus as either UA or HNAc and the non-reducing terminus as IdoA2S enabled this discrimination.

Two series of oligosaccharides that are likely derived from DS (Table 1) and four series of oligosaccharides likely derived from HS (Table 2), based on the presence of unacetylated HN residues in the HS-derived oligosaccharides, were identified. The formation of DS-derived oligosaccharides terminating in HNAc (Table 1, series 1) is consistent with the reported action of hyaluronidase to act on the GalNAc-UA linkages of DS. The second series of DS-derived oligosaccharides was composed of an odd number of saccharides with UA at both the reducing and non-reducing termini (Table 1, series 2). As with series 1, these oligosaccharides had a concomitant increase in the number of sulfate residues with oligosaccharide length. Although not wanting to be bound by theory, we would suggest that the sulfate residues are distributed along the DS oligosaccharides, consistent with the reported action of hyaluronidase to GalNAc-4-S residues. Although the smaller oligosaccharides (di- to octasaccharide) had up to 2 sulfates per disaccharide, the larger (up to hexadecasaccharide) had fewer sulfates. This may result from the loss of sulfate residues in the ion source of the mass spectrometer as has been previously reported. However, these oligosaccharides may also arise in part from the structural heterogeneity present in DS. We have previously reported tri- and pentasaccharides, isolated from MPS I urine, and identified them as being derived from DS by the presence of GalNAc-4-S as the penultimate residue at the non-reducing end. These oligosaccharides were suggested to derive from endohydrolase activity against the UA-GalNAc bond in DS. This concept is further supported here in MPS II, with the identification of tri-, penta- and heptasaccharides derived from DS. However, we did not observe any significant signals from larger oligosaccharide species in this series. The limitation on the size of the oligosaccharide identified may reflect substrate specificity of the endoglucuronidase activity for terminal regions of the DS chains, although it may also be that larger species are not present in sufficient amounts to be resolved from the more abundant oligosaccharide species terminating in HNAc, seen in the complex spectra of the larger oligosaccharides.

The oligosaccharide series containing UA-HN and UA-HNAc disaccharides provides a more complex picture of endohydrolysis of HS. Two series of oligosaccharides (Table 2, series 1 and 2) are likely products of heparanase activity towards HS. These series have a trisaccharide (UA-HN-UA) or a pentasaccharide (UA-HN-UA-HN-UA) base structure with an increasing number (up to five) of HNAc-UA disaccharides. Interestingly, the number of sulfates associated with this series does not increase with the size of the oligosaccharide but remains relatively constant between three and seven. In light of the reported domain structure of HS with regions of high (NS) and low (NA) sulfation, it seems probable that these two series of oligosaccharides represent short NS domains with an increasing extension of the NA domain. Thus, the heparanase appears to have specificity for the relatively highly sulphated linkage region between the NS and NA domains (thus producing the base tri and pentasaccharides) and also for the unsulfated region represented by the extending GlcNAc-UA disaccharides (NA domain). Previous studies have indicated multiple substrates for heparanase activity. For example, earlier studies indicated that human heparanase cleaved a sequence within the highly modified NS domains of HS. Heparanase from CHO cells has been proposed to have substrate specificity for the mixed NA/NS domains. Studies on the heparanase from a rat parathyroid cell line identified relatively undersulfated structures at the cleavage site and also proposed that the cleavage occurred at the boundary of highly sulphated and undersulfated domains. At the same time studies on recombinant human heparanase with defined tetra and hexasaccharide structures indicated the requirement for a highly sulphated structure containing an unsulfated GlcA at the cleavage site.

Although there appears to be only one candidate gene for heparanase, it is also plausible that there are two different enzymes with specificities for either NS or NA domains in HS. Heparanase activity is also likely to be responsible for the generation of the nonasaccharide (UA-HN-[UA-HN]$_2$-UA-HNAc-UA) (Table 2, series 3) that represents a longer NS domain with heparanase cleavage occurring after the first HNAc in the adjacent NA domain. The final HS-derived oligosaccharide series (Table 2, series 4) represents similar structures to those seen in series 1 but with a HNAc as opposed to a UA at the reducing end. This suggests the action of an endohydrolase on the HNAc-UA linkage in HS. In this series of oligosaccharides the number of sulfates does not proportionately increase with oligosaccharide length, again indicating that the extension of the UA-HNAc disaccharide is into the NA domain, and thus the endoenzyme specificity is for the NA domain.

The absence of any oligosaccharides larger than a pentasaccharide containing only UA and HN suggests that the NA/NS domain of HS is more resistant to heparanase activity than the NA domains. Presumably, the larger NS regions are to be found in the high molecular weight structures eluting at $V_0$ from the Bio-Gel P4 column. The structures observed, appear to arise primarily from the action of heparanase in NA domains of HS, these regions of low sulfation are separated by short (up to three) regions of sulfated UA-HN disaccharide repeats (NS domains). The reducing terminus of each oligosaccharide is then trimmed back by the action of exoenzymes to the first IdoA2S residue where, as a result of the deficient enzyme, exodegradation is halted. A similar scheme involving an endo-N-acetylglucoasminidase activity is also proposed to account for the HS derived oligosaccharides in Table 2 series 4 (FIG. 70).

The study of stored oligosaccharides from patients with a defective exodigestion of glycosaminoglycan chains (MPS patients) provides a unique, global insight into the process of endohydrolysis of glycosaminoglycans in the endosomal/lysosomal network. In urine from an MPS II patient we have observed a significant proportion of low molecular weight oligosaccharides (40% of uronic acid in hexadecasaccharide or smaller), indicating that the action of these endoglycosidases provides a significant contribution to the total degradation of GAG in the lysosome. Characterisation of the resulting oligosaccharides has provided us with new insight into the endoenzymes involved and their substrate specificities. In addition to the hyaluronidase and heparanase we have provided evidence for the action of an endo-glucuronidase activity on DS and an endo-N-acetylglucosaminidase activity on HS. We have also provided evidence that the majority of HS digestion occurs in the low sulfation (NA) regions. Further detailed characterisation of the stored substrates in MPS II and other MPS types will increase our understanding of these enzymes and their role in GAG turnover.

This invention comprises general and specific compositions for LSD diagnostics, including multiplex bead technology. Although species specific antibodies have been used as illustrative examples, other types of antibodies that bind LSD target proteins are not considered to deviate from the spirit and scope of the claimed invention.

REFERENCES CITED

The following references, to the extent that they provide exemplary procedural or other details supplementary to those set forth herein, are specifically incorporated herein by reference.

U.S. PATENT DOCUMENTS

U.S. Pat. No. 6,449,562 ("the '562 Patent") entitled "Multiplexed Analysis of Clinical Specimens Apparatus and Method," having Chandler et al. listed as inventors was issued on Sep. 10, 2002.

U.S. Pat. No. 6,524,793 ("the '793 Patent") entitled "Multiplexed Analysis of Clinical Specimens Apparatus and Method," having Chandler et al. listed as inventors, was issued on Feb. 25, 2003.

U.S. patent application Ser. No. 09/956,857 ("the '857 Application") entitled "Multiple Reporter Read-out for Bioassays" was published on Mar. 20, 2003.

PCT Application AU03/00731 entitled "identification of Oligosaccharides and their Use in the Diagnosis and Evaluation of Mucopolysaccharidoses and Other Related Disorders," having Hopwood et al., listed as inventors, filed on Jun. 13, 2003

Other Publications

Carlsson, S. R., M. Fukuda, Structure of human lysosomal membrane glycoprotein 1, Assignment of disulfide bonds and visualization of its domain arrangement., *J. Biol. Chem.* 264:20526-20531 (1989).

Fransen, J. A., L. A. Ginsel, P. H. Cambier, J. Klumperman, R. P. Oude Elferink, J. M. Tager, Immunocytochemical demonstration of the lysosomal enzyme alpha-glucosidase in the brush border of human intestinal epithelial cells, *Eur J Cell Biol* 47:72-80 (1988).

Harlow, E., D. Lane, *Antibodies, A laboratory manual*, Cold Spring Harbor Laboratory (1988).

Hua, C. T. et al., Evaluation of the lysosome-associated membrane protein LAMP-2 as a marker for lysosomal storage disorders, *Clin. Chem.* 44(10): 2094-2102 (1988).

Isaac E L, Karageorgous L E, Brooks D A, Hopwood J J and Meikle P J. Experimental Cell Research 2000, 254: 204-209].

Isbrandt, D., G. Arlt, D. A. Brooks, J. J. Hopwood, K. von Figura, and C. Peters, Mucopolysaccharidosis VI (Maroteaux-Lamy syndrome): Six unique arylsulfatase B gene alleles causing variable disease phenotypes, *Am J Hum Genet* 54(3): 454-63 (1994).

Meikle et al., Prevalence of lysosomal storage disorders, *JAMA* 281: 249-254 (1999).

Neufeld, E. F. and J. Muenzer, The mucopolysaccharidoses, *The Metabolic & Molecular Basis of Inherited Disease, 7th* Edition., pp. 2465-2494 (1995).

Umapathysivam, K., J. J. Hopwood, P. J. Meikle, Determination of acid alpha-glucosidase activity in blood spots as a diagnosis for Pompe Disease, *Clin. Chem.* 47(8): 1378-1383 (2001).

Qi and Grabowski [Qi T L and Grabowski G A J Biol Chem 1994, 269: 16746-16753.

Zola, H., D. Brooks, Techniques for the Production and Characterization of Monoclonal Hybridoma Antibodies, *Monoclonal Hybridoma Antibodies: Techniques and Applications* (1982).

Kramer, K. L., and Yost, H. J. (2003) *Annu Rev Genet* 37, 461-484

Trowbridge, J. M., and Gallo, R. L. (2002) *Glycobiology* 12, 117R-125R

Lindahl, U., Kusche-Gullberg, M., and Kjellen, L. (1998) *J Biol Chem* 273, 24979-24982

Lyon, M., and Gallagher, J. T. (1998) *Matrix Biol* 17, 485-493

Maccarana, M., Sakura, Y., Tawada, A., Yoshida, K., and Lindahl, U. (1996) *J Biol Chem* 271, 17804-17810

Prydz, K., and Dalen, K. T. (2000) *J Cell Sci* 113 Pt 2, 193-205

Kreil, G. (1995) *Protein Sci* 4, 1666-1669

Lokeshwar, V. B., Rubinowicz, D., Schroeder, G. L., Forgacs, E., Minna, J. D., Block, N. L., Nadji, M., and Lokeshwar, B. L. (2001) *J Biol Chem* 276, 11922-11932

Bame, K. J. (2001) *Glycobiology* 11, 91R-98R

Hulett, M. D., Freeman, C., Hamdorf, B. J., Baker, R. T., Harris, M. J., and Parish, C. R. (1999) *Nat Med* 5, 803-809

Vlodavsky, I., and Friedmann, Y. (2001) *J Clin Invest* 108, 341-347

Dempsey, L. A., Brunn, G. J., and Platt, J. L. (2000) *Trends Biochem Sci* 25, 349-351

Gingis-Velitski, S., Zetser, A., Kaplan, V., Ben-Zaken, O., Cohen, E., Levy-Adam, F., Bashenko, Y., Flugelman, M. Y., Vlodavsky, I., and Ilan, N. (2004) *J Biol Chem*

Morimoto-Tomita, M., Uchimura, K., Werb, Z., Hemmerich, S., and Rosen, S. D. (2002) *J Biol Chem* 277, 49175-49185

Neufeld, E. F., and Meunzer, J. (2001) in *The Molecular Basis of Inherited Disease* (Scriver, C. R., Beaudet, A. L., Sly, W. S., and Valle, D., eds), pp. 3421-3452, McGraw-Hill, N.Y.

Unger, E. G., Durrant, J., Anson, D. S., and Hopwood, J. J. (1994) *Biochem J* 304 (Pt 1), 43-49

Bielicki, J., Hopwood, J. J., Wilson, P. J., and Anson, D. S. (1993) *Biochem J* 289 (Pt 1), 241-246

Blumenkrantz, N., and Asboe-Hansen, G. (1973) *Anal Biochem* 54, 484-489

Ramsay, S. L., Meikle, P. J., and Hopwood, J. J. (2003) *Mol Genet Metab* 78, 193-204

Fuller, M., Meikle, P. J., and Hopwood, J. J. (2004) *Glycobiology* 14, 443-450

Knudson, W., Gundlach, M. W., Schmid, T. M., and Conrad, H. E. (1984) *Biochemistry* 23, 368-375

Marchetti, D., Liu, S., Spohn, W. C., and Carson, D. D. (1997) *J Biol Chem* 272, 15891-15897

Pikas, D. S., Li, J. P., Vlodavsky, I., and Lindahl, U. (1998) *J Biol Chem* 273, 18770-18777

Bame, K. J., and Robson, K. (1997) *J Biol Chem* 272, 2245-2251

Bame, K. J., Venkatesan, I., Stelling, H. D., and Tumova, S. (2000) *Glycobiology* 10, 715-726

Podyma-Inoue, K. A., Yokote, H., Sakaguchi, K., Ikuta, M., and Yanagishita, M. (2002) *J Biol Chem* 277, 32459-32465

Okada, Y., Yamada, S., Toyoshima, M., Dong, J., Nakajima, M., and Sugahara, K. (2002) *J Biol Chem* 277, 42488-42495

Toyoshima, M., and Nakajima, M. (1999) *J Biol Chem* 274, 24153-24160

What is claimed is:

1. A diagnostic composition comprising:
a purified capture antibody capable of binding a target antigen; and
a microsphere having the purified capture antibody conjugated to the microsphere;
wherein,
the target antigen are: saposin (SeqID No. 1), LAMP-1 (SeqID No. 2), α-iduronidase (SeqID No. 3), α-glucosidase (SeqID No. 4), β-glucosidase (SeqID No. 5), 2-sulphatase (SeqID No. 6), 4-sulphatase (SeqID No. 7), α-galactosidase (SeqID No. 8), sphingomyelinase (SeqID No. 9), 3-sulphatase (SeqID No. 10), and sulphamidase; and
wherein, the microsphere comprises at least a first fluorophore and a second fluorophore.

2. The diagnostic composition of claim 1, further comprising a purified detection antibody, wherein the purified detection antibody is capable of binding the target antigen, and the purified detection antibody is conjugated to a detection label.

3. The diagnostic composition of claim 2, wherein the detection label is phycoerythrin, or Biotin.

4. The diagnostic composition of claim 1, wherein the first fluorophore is spectrally distinct from the second fluorophore.

5. The diagnostic composition of claim 1, wherein the microsphere has a diameter of about 5 μm.

6. A diagnostic composition comprising:
a first microsphere conjugated to a first purified capture antibody that selectively binds to an epitope of saposin (SeqID No. 1);
a second microsphere conjugated to a second purified capture antibody that selectively binds to an epitope of LAMP-1 (SeqID No. 2);
a third microsphere conjugated to a third purified capture antibody that selectively binds to an epitope of α-iduronidase (SeqID No. 3);
a fourth microsphere conjugated to a fourth purified capture antibody that selectively binds to an epitope of α-glucosidase (SeqID No. 4);
a fifth microsphere conjugated to a first purified capture antibody that selectively binds to an epitope of β-glucosidase (SeqID No. 5);
a sixth microsphere conjugated to a second purified capture antibody that selectively binds to an epitope of 2-sulphatase (SeqID No. 6);
a seventh microsphere conjugated to a third purified capture antibody that selectively binds to an epitope of 4-sulphatase (SeqID No. 7);
an eighth microsphere conjugated to a fourth purified capture antibody that selectively binds to an epitope of α-galactosidase (SeqID No. 8);
a ninth microsphere conjugated to a third purified capture antibody that selectively binds to an epitope of sphingomyelinase (SeqID No. 9); and
a tenth microsphere conjugated to a fourth purified capture antibody that selectively binds to an epitope of 3-sulphatase (SeqID No. 10);
wherein, the first through tenth microspheres contain a specific ratio of fluorophores and are spectrally distinct from each other; and
wherein β-galactosidase or galactocerebrosidase, heparan-N-sulphatase, α-N-acetylglucosaminidase, and galactose-6-sulphatase are not present.

7. The diagnostic composition of claim 6, further comprising:
a first purified detection antibody conjugated to a fluorescent detection label and that selectively binds to an epitope of saposin (SeqID No. 1);
a second purified detection antibody conjugated to a fluorescent detection label and that selectively binds to an epitope of LAMP-1 (SeqID No. 2);
a third purified detection antibody conjugated to a fluorescent detection label and that selectively binds to an epitope of α-iduronidase (SeqID No. 3);
a fourth purified detection antibody conjugated to a fluorescent detection label and that selectively binds to an epitope of α-glucosidase (SeqID No. 4);
a fifth purified detection antibody conjugated to a fluorescent detection label and that selectively binds to an epitope of β-glucosidase (SeqID No. 5);
a sixth purified detection antibody conjugated to a fluorescent detection label and that selectively binds to an epitope of 2-sulphatase (SeqID No. 6);
a seventh purified detection antibody conjugated to a fluorescent detection label and that selectively binds to an epitope of 4-sulphatase (SeqID No. 7);
an eighth purified detection antibody conjugated to a fluorescent detection label and that selectively binds to an epitope of α-galactosidase (SeqID No. 8);
a ninth purified detection antibody conjugated to a fluorescent detection label and that selectively binds to an epitope of sphingomyelinase (SeqID No. 9);
a tenth purified detection antibody conjugated to a fluorescent detection label and that selectively binds to an epitope of 3-sulphatase (SeqID No. 10) and
wherein β-galactosidase or galactocerebrosidase, heparan-N-sulphatase, α-N-acetylglucosaminidase, and galactose-6-sulphatase are not present.

* * * * *

UNITED STATES PATENT AND TRADEMARK OFFICE
CERTIFICATE OF CORRECTION

PATENT NO. : 7,615,224 B2  Page 1 of 1
APPLICATION NO. : 11/291621
DATED : November 10, 2009
INVENTOR(S) : Meikle et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 243 days.

Signed and Sealed this

Nineteenth Day of October, 2010

David J. Kappos
*Director of the United States Patent and Trademark Office*